(12) United States Patent
Bertoni

(10) Patent No.: US 9,968,620 B2
(45) Date of Patent: May 15, 2018

(54) METHODS OF TREATING LYMPHOMA USING THIENOTRIAZOLODIAZEPINE COMPOUNDS

(71) Applicant: ONCOETHIX GmbH, Lucerne (CH)

(72) Inventor: Francesco Bertoni, Bellinzona (CH)

(73) Assignee: ONCOETHIX GMBH, Lucerne (CH)

( * ) Notice: Subject to any disclaimer, the term of this patent is extended or adjusted under 35 U.S.C. 154(b) by 0 days. days.

(21) Appl. No.: 15/504,722

(22) PCT Filed: Aug. 19, 2015

(86) PCT No.: PCT/EP2015/069092
§ 371 (c)(1),
(2) Date: Feb. 17, 2017

(87) PCT Pub. No.: WO2016/026912
PCT Pub. Date: Feb. 25, 2016

(65) Prior Publication Data
US 2017/0273988 A1 Sep. 28, 2017

Related U.S. Application Data

(60) Provisional application No. 62/086,609, filed on Dec. 2, 2014, provisional application No. 62/039,072, filed on Aug. 19, 2014.

(51) Int. Cl.

| | |
|---|---|
| A61K 31/551 | (2006.01) |
| C07D 487/12 | (2006.01) |
| C07D 495/14 | (2006.01) |
| A61K 45/06 | (2006.01) |
| A61K 31/203 | (2006.01) |
| A61K 31/4184 | (2006.01) |
| A61K 31/436 | (2006.01) |
| A61K 31/454 | (2006.01) |
| A61K 31/519 | (2006.01) |
| A61K 31/706 | (2006.01) |
| A61K 38/07 | (2006.01) |

(52) U.S. Cl.
CPC .......... *A61K 31/551* (2013.01); *A61K 31/203* (2013.01); *A61K 31/4184* (2013.01); *A61K 31/436* (2013.01); *A61K 31/454* (2013.01); *A61K 31/519* (2013.01); *A61K 31/706* (2013.01); *A61K 38/07* (2013.01); *A61K 45/06* (2013.01)

(58) Field of Classification Search
CPC ... A61K 31/551; C07D 487/12; C07D 495/14
USPC .......................................... 514/220; 540/560
See application file for complete search history.

(56) References Cited

U.S. PATENT DOCUMENTS

| | | |
|---|---|---|
| 2010/0286127 A1 | 11/2010 | Miyoshi et al. |
| 2016/0158246 A1* | 6/2016 | Bertoni ................ A61K 9/1635 514/220 |
| 2017/0095484 A1* | 4/2017 | Noel .................... A61K 45/06 |

FOREIGN PATENT DOCUMENTS

| | | |
|---|---|---|
| EP | 1297836 A1 | 4/2003 |
| WO | 2014001356 A1 | 1/2014 |
| WO | 2015018520 A1 | 2/2015 |
| WO | 2015018521 A1 | 2/2015 |

* cited by examiner

*Primary Examiner* — Brenda L Coleman
(74) *Attorney, Agent, or Firm* — Catherine D. Fitch; Richard S. Parr

(57) ABSTRACT

A method of treating lymphoma in a mammal comprises the step of: administering to a patient a pharmaceutical acceptable amount of a compound being a thienotriazolodiazepine compound of the Formula (1) wherein $R^1$ is alkyl having a carbon number of 1-4, $R^2$ is a hydrogen atom; a halogen atom; or alkyl having a carbon number of 1-4 optionally substituted by a halogen atom or a hydroxyl group, $R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—$CO$—$(CH_2)_q$—$R^8$ wherein R is a hydrogen atom or alkyl having a carbon number of 1-4, n is an integer of 0-2, and $R^8$ is phenyl or pyridyl optionally substituted by a halogen atom, and $R^4$ is —$(CH_2)_a$—$CO$—$NH$—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, or a pharmaceutically acceptable salt thereof or a hydrate or solvate thereof. The lymphoma to be treated is diffuse large B-cell lymphom (DLBCL) specifically selected from activated B-cell DLBCL (ABC-DLBCL) and germinal B-cell DLBCL (GBC-DLBCL).

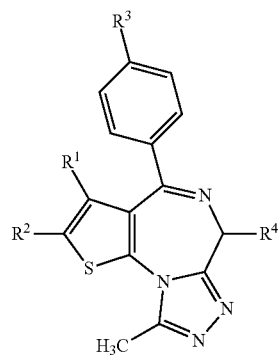

(1)

3 Claims, 20 Drawing Sheets

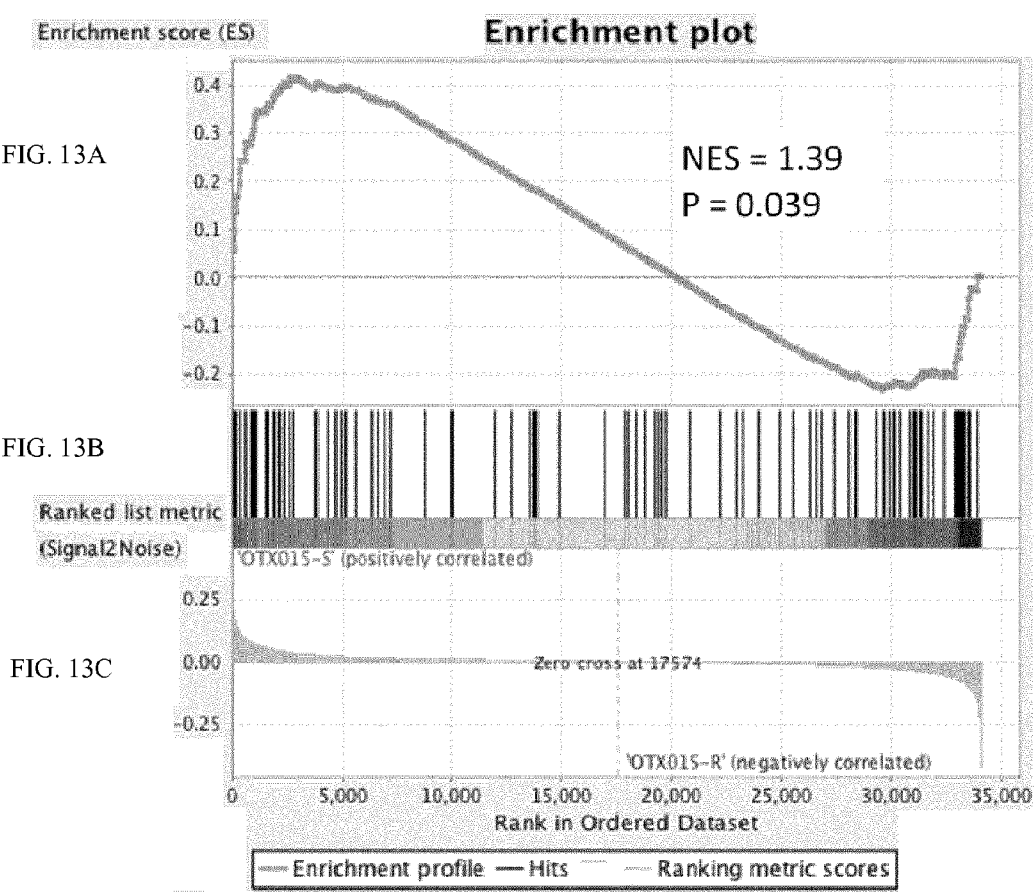

METHODS OF TREATING LYMPHOMA USING THIENOTRIAZOLODIAZEPINE COMPOUNDS

This application is a National Stage application of PCT/EP2015/069092, filed Aug. 19, 2015, which claims the benefit of U.S. Provisional Application Ser. No. 62/039,072, filed Aug. 19, 2014, and 62/086,609, filed Dec. 2, 2014, all of which is incorporated herein by reference in its entirety.

FIELD OF INVENTION

The present disclosure describes methods of treating lymphoma using thienotriazolodiazepine compounds which have improved solubility and bioavailability and may be provided in the form of solid dispersions. In particular, the present disclosure describes methods of treating diffuse large B-cell lymphoma (DLBCL) using thienotriazolodiazepine compounds which have improved solubility and bioavailability and may be provided in the form of solid dispersions.

BACKGROUND OF THE INVENTION

Diffuse large B-cell lymphoma (DLBCL) is the most common lymphoma, accounting for 30%-40% of all cases. Despite a major improvement in the cure rate, a large number of DLBCL patients lack therapeutic options. Aberrant changes in histone modifications, DNA methylation and expression levels of non-coding RNA, including microRNA (miRNA), contribute to DLBCL pathogenesis and represent potential therapeutic targets. Compound (1-1) targets bromodomain and extra terminal (BET) proteins, which are epigenetic readers contributing to gene transcription. It has shown preclinical activity in hematologic and solid tumor models and promising early results in an ongoing oncology phase I study. However, so far, there is no data regarding the genome-wide effects of BET Bromodomain inhibition on miRNAs regulation.

The compound of Formula (1), described herein below, has been shown to inhibit the binding of acetylated histone H4 to the tandem bromodomain (BRD)-containing family of transcriptional regulators known as the BET (bromodomains and extraterminal) proteins, which include BRD2, BRD3, and BRD4. See U.S. Patent Application Publication No. 2010/0286127 A1, which is incorporated herein by reference in its entirety. The BET proteins have emerged as major epigenetic regulators of proliferation and differentiation and also have been associated with predisposition to dyslipidemia or improper regulation of adipogenesis, elevated inflammatory profile and risk for cardiovascular disease and type 2 diabetes, and increased susceptibility to autoimmune diseases such as rheumatoid arthritis and systemic lupus erythematosus as reported by Denis, G. V. "Bromodomain coactivators in cancer, obesity, type 2 diabetes, and inflammation," *Discov Med* 2010; 10:489-499, which is incorporated herein by reference in its entirety. Accordingly, the compound of formula (1) may be useful for treatment of various cancers, cardiovascular disease, type 2 diabetes, and autoimmune disorders such as rheumatoid arthritis and systemic lupus erythematosus.

BRIEF SUMMARY OF THE INVENTION

In some embodiments, the present disclosure provides for methods of treating lymphoma using the compositions described herein. In some embodiments, the present disclosure provides for methods of treating diffuse large B-cell lymphoma (e.g. DLBCL of an activated B-cell (ABC) subtype or DLBCL of germinal center B-cell like (GCB) subtype) using the compositions described herein.

In some embodiments, the present disclosure provides for methods of treating lymphoma in a mammal comprising: administering to a patient in need a pharmaceutically acceptable amount of a composition comprising any of the compositions described in Sections III, IV, V and VI described herein. In some embodiments, the present disclosure provides for methods of treating DLBCL (e.g. DLBCL of an activated B-cell (ABC) subtype ("ABC-DLBCL") or DLBCL of germinal center B-cell like (GCB) ("GCB-DLBCL") subtype) in a mammal comprising: administering to a patient in need a pharmaceutically acceptable amount of a composition comprising any of the compositions described in Sections III, IV, V and VI described herein.

In some embodiments, the present disclosure provides for a compound of Formula (1), in particular of Formula (1A) for use in treating lymphoma. In some embodiments, the present disclosure provides for a compound of Formula (1), in particular of Formula (1A) for use in treating DLBCL (e.g. ABC-DLBCL or GBC-DLBCL)

In some embodiments, the present disclosure provides for a solid dispersion according to any of the compositions described in Sections III, IV, V and VI described herein for use in treating lymphoma. In some embodiments, the present disclosure provides for a solid dispersion according to any of the compositions described in Sections III, IV, V and VI described herein for use in treating DLBCL (e.g., ABC-DLBCL or GBC-DLBCL), In some embodiments, the present disclosure provides for methods of treating DLBCL (e.g., ABC-DLBCL or GBC-DLBCL) using thienotriazolodiazepine compound of the Formula (1)

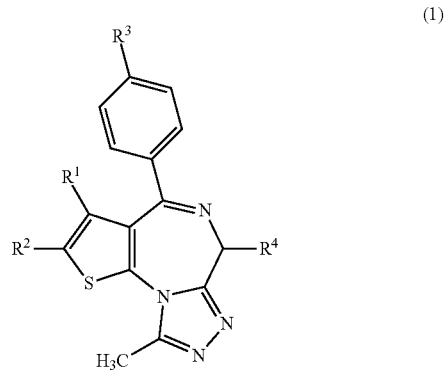

(1)

wherein
$R^1$ is alkyl having a carbon number of 1-4,
$R^2$ is a hydrogen atom; a halogen atom; or alkyl having a carbon number of 1-4 optionally substituted by a halogen atom or a hydroxyl group,
$R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and $R^4$ is —$(CH_2)_a$—CO—NH—R wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, or a pharmaceutically acceptable salt thereof or a hydrate or solvate thereof. In some embodiments the DLBCL is selected from the group consisting of activated B-cell DLBCL (ABC-DLBCL) and germinal B-cell DLBCL (GBC-DLBCL).

In some such embodiments, the cells of the DLBCL exhibit decreased levels of micro RNA selected from the group consisting of miR-92a-1-5p, miR-21-3p or combinations thereof upon exposure to the thienotriazolodiazepine compound of the Formula (1).

In some other such embodiments, the cells of the DLBCL exhibit increased levels of micro RNA miR-96-5p upon exposure to the thienotriazolodiazepine compound of the Formula (1).

In some embodiments, Formula (1) is selected from Formula (1A):

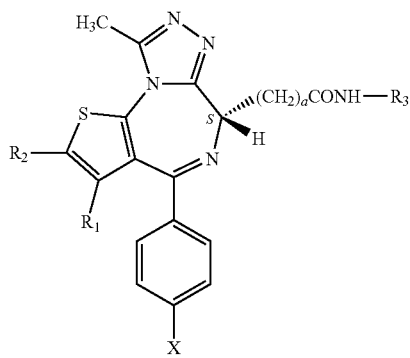

wherein X is a halogen, $R^1$ is $C_1$-$C_4$ alkyl, $R^2$ is $C_1$-$C_4$ alkyl, a is an integer of 1-4, $R^3$ is $C_1$-$C_4$ alkyl, $C_1$-$C_4$ hydroxyalkyl, $C_1$-$C_4$ alkoxy, phenyl optionally having substituent(s) as defined for $R^9$ in Formula (1), or heteroaryl optionally having substituent(s) as defined for $R^9$ in Formula (1), a pharmaceutically acceptable salt thereof or a hydrate thereof.

In one such embodiment, the thienotriazolodiazepine compound is formulated as a solid dispersion comprising an amorphous thienotriazolodiazepine compound and a pharmaceutically acceptable polymer.

In one embodiment, Formula (1) is selected from the group consisting of: (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof; (ii) methyl (S)-{4-(3'-cyanobiphenyl-4-yl)-2,3,9-trimethyl-6H-thieno[3,2-f][1,2,4]triazolo[4,3-a][1,4]diazepin-6-yl}acetate, (iii) methyl (S)-{2,3,9-trimethyl-4-(4-phenylaminophenyl)-6-thieno[3,2-f][1,2,4]triazolo[4,3-a][1,4]diazepin-6-yl}acetate; and (iv) methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate.

In one embodiment, the thienotriazolodiazepine compound represented by Formula (1) is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide dihydrate.

In one embodiment, the thienotriazolodiazepine compound represented by Formula (1) is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide.

In some embodiments the present disclosure provides for methods of treating lymphoma comprising administering a thienotriazolodiazepine compound of the Formula (1), and more particularly of the Formula (1A), in combination with one or more other therapeutic agents. In one embodiment, the thienotriazolodiazepine compound of the Formula (1) and the therapeutic agent are administered concomitant. In one embodiment, the thienotriazolodiazepine compound of the Formula (1) and the chemotherapy drug are administered sequentially.

In some embodiments the present disclosure provides for methods of treating DLBCL comprising administering a thienotriazolodiazepine compound of the Formula (1), and more particularly of the Formula (1A), in combination with one or more therapeutic agents selected from the group consisting of m-TOR inhibitors BTK inhibitors, DNA methyltransferase inhibitors, immunomodulatory agents, DNA alkylating agents (e.g. nitrogen mustards, nitrosureas, alkyl sulfonates, triazines, and ethylenimines), histone deacetylase inhibitors (also known as HDAC inhibitors or HDIs), all-trans retinoic acid (also known as ATRA), doxorubicin, and esters, derivatives, prodrugs, salts, and complexes thereof. In some embodiments the DLBCL is selected from the group consisting of activated B-cell DLBCL (ABC-DLBCL) and germinal B-cell DLBCL (GBC-DLBCL)

In some embodiments the method further comprises administering to the patient an mTOR inhibitor. In one such embodiment the mTOR inhibitor is selected from the group consisting of rapamycin, temsirolimus, ridaforolimus, everolimus, and esters, derivatives, prodrugs, salts, and complexes thereof. In one such embodiment the mTOR inhibitor is everolimus. The thienotriazolodiazepine compound and the mTOR inhibitor can be administered simultaneously or sequentially. In some embodiments such combination of thienotriazolodiazepine compound and mTOR inhibitor produces a synergistic effect.

In some embodiments the method further comprises administering to the patient a BTK inhibitor. In one such embodiment the BTK inhibitor is ibrutinib, or an ester, derivative, prodrug, salt, or complex thereof. In one such embodiment the BTK inhibitor is ibrutinib. The thienotriazolodiazepine compound and the BTK inhibitor can be administered simultaneously or sequentially. In some embodiments such combination of thienotriazolodiazepine compound and BTK inhibitor produces a synergistic effect.

In some embodiments the method further comprises administering to the patient a DNA methyltransferase inhibitor. In one such embodiment the DNA methyltransferase is selected from the group consisting of azacitidine, decitabine, and esters, derivatives, prodrugs, salts, and complexes thereof. In one such embodiment the DNA methyltransferase inhibitor is decitabine. In one such embodiment the DNA methyltransferase inhibitor is azacitidine. The thienotriazolodiazepine compound and the DNA methyltransferase inhibitor can be administered simultaneously or sequentially. In some embodiments such combination of thienotriazolodiazepine compound and DNA methyltransferase inhibitor produces a synergistic effect.

In some embodiments the method further comprises administering to the patient an immunomodulator. In one such embodiment the immunomodulator is selected from the group consisting of thalidomide, lenalidomide, pomalidomide, and esters, derivatives, prodrugs, salts, and complexes thereof. In one such embodiment the immunomodulator is lenalidomide. The thienotriazolodiazepine compound and the immunomodulator can be administered simultaneously or sequentially. In some embodiments such combination of thienotriazolodiazepine compound and immunomodulator produces a synergistic effect.

In some embodiments the method further comprises administering to the patient DNA alkylating agent. In one such embodiment the DNA alkylating agent is selected from the group consisting of nitrogen mustards, nitrosureas, alkylsulfonates, triazines, and ethylenimines. In one such embodiment the nitrogen mustard is selected from the group consisting of bendamustine, methchlorethamine, chlorambucil, cyclophosphamide, ifosfaminde, melphalan, and esters, derivatives, prodrugs, salts, and complexes thereof. In one such embodiment the DNA alkylating agent is bendamustine. The thienotriazolodiazepine compound and the DNA alkylating agent can be administered simultaneously or sequentially. In some embodiments such combination of thienotriazolodiazepine compound and the DNA alkylating agent produces a synergistic effect.

In some embodiments the method further comprises administering to the patient a histone deacetylase inhibitor. In one such embodiment the histone deacetylase inhibitor is selected from the group consisting of romidepsin, vorinostat, entinostat, panobinostat, and esters, derivatives, prodrugs, salts, and complexes thereof. The thienotriazolodiazepine compound and the histone deacetylase inhibitor can be administered simultaneously or sequentially. In some embodiments such combination of thienotriazolodiazepine compound and histone deacetylase inhibitor produces a synergistic effect.

In some embodiments the method further comprises administering to the patient all-trans retinoic acid (also known as ATRA). The thienotriazolodiazepine compound and all-trans retinoic acid can be administered simultaneously or sequentially. In some embodiments such combination of thienotriazolodiazepine compound and all-trans retinoic acid produces a synergistic effect.

In one embodiment, the thienotriazolodiazepine compound of the Formula (1) is formed as a solid dispersion. In one embodiment, the solid dispersion comprises an amorphous thienotriazolodiazepine compound of Formula (1) or a pharmaceutically acceptable salt thereof or a hydrate thereof; and a pharmaceutically acceptable polymer. In one embodiment, the solid dispersion exhibits an X-ray powder diffraction pattern substantially free of diffraction lines associated with crystalline thienotriazolodiazepine compound of Formula (1). In one embodiment, the pharmaceutically acceptable polymer is hydroxypropylmethylcellulose acetate succinate having a thienotriazolodiazepine compound to hydroxypropylmethylcellulose acetate succinate (HPMCAS) weight ratio of 1:3 to 1:1. In one embodiment, the solid dispersion exhibits a single glass transition temperature (Tg) inflection point ranging from about 130° C. to about 140° C.

In one embodiment, a solid dispersion comprises an amorphous thienotriazolodiazepine compound of (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide dihydrate or a pharmaceutically acceptable salt thereof or a hydrate thereof; and a pharmaceutically acceptable polymer. In one embodiment, the solid dispersion exhibits an X-ray powder diffraction pattern substantially free of diffraction lines associated with crystalline thienotriazolodiazepine compound of (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide dihydrate. In one embodiment, the pharmaceutically acceptable polymer is hydroxypropylmethylcellulose acetate succinate having a thienotriazolodiazepine compound to hydroxypropylmethylcellulose acetate succinate (HPMCAS) weight ratio of 1:3 to 1:1. In one embodiment, the solid dispersion exhibits a single glass transition temperature (Tg) inflection point ranging from about 130° C. to about 140° C.

It should be understood that any embodiment of the compounds according to Formula (1) described herein may be used in any embodiment of a pharmaceutical composition described herein, unless indicated otherwise. Moreover, any compound or pharmaceutical composition described herein as embodiment of the invention may be used as a medicament, in particular for treating lymphoma (in particular DLBCL, e.g. ABC-DLBCL or GBC-DLBCL) as described in embodiments herein, unless indicated otherwise.

BRIEF DESCRIPTION OF THE DRAWINGS

The foregoing summary, as well as the following detailed description of embodiments of the pharmaceutical compositions including thienotriazolodiazepine formulations and methods of the present invention, will be better understood when read in conjunction with the appended drawings of exemplary embodiments. It should be understood, however, that the invention is not limited to the precise arrangements and instrumentalities shown.

In the drawings:

FIGS. 13A-13C illustrate how compound (1-1) affects the expression of hsa-miR-96-5p, has-miR-21-3p and hsa-miR-92a-5p, respectively. Box plots show the expression of miR-96-5p in DMSO and compound (1-1)-treated Dohh2 after 8 h (FIG. 13A), miR-21-3p in DMSO and treated Dohh2 after 4 h (FIG. 13B), and miR-92a-5p in DMSO and treated SU-DHL2 after 8 h (FIG. 13C);

DETAILED DESCRIPTION OF THE INVENTION

Figure 1A:
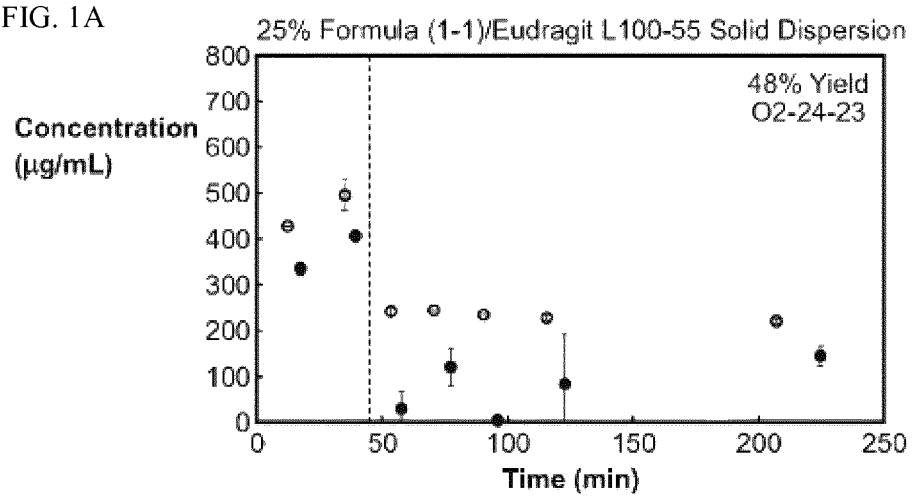
FIG. 1A illustrates dissolution profile of a comparator formulation comprising a solid dispersion comprising 25% compound (1-1) and Eudragit L100-55.
Figure 1B:
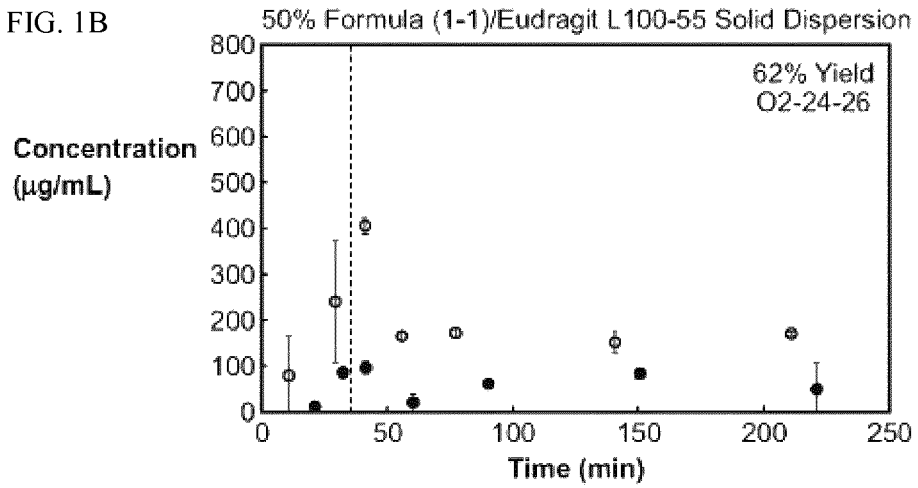
FIG. 1B illustrates dissolution profile of a comparator formulation comprising a solid dispersion comprising 50% compound (1-1) and Eudragit L100-55.
Figure 1C:
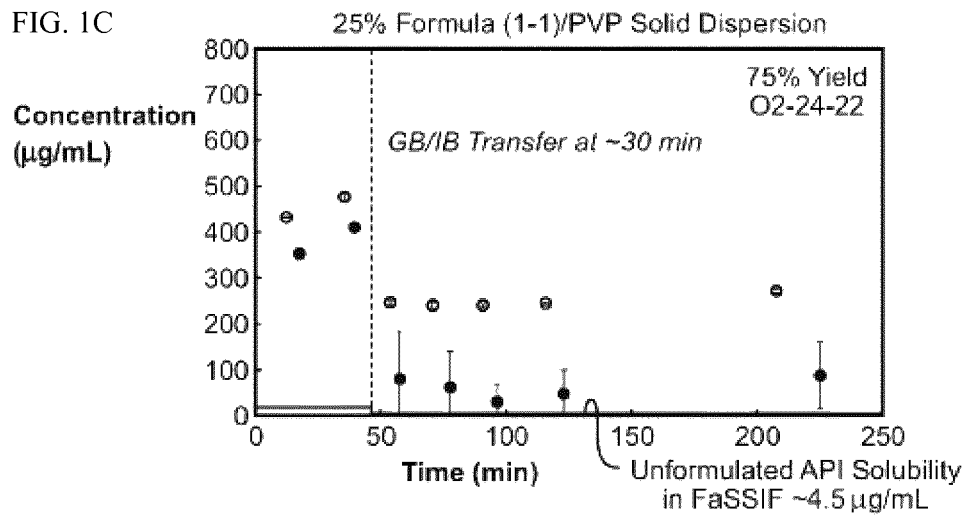
FIG. 1C illustrates dissolution profile of an exemplary formulation comprising a solid dispersion comprising 25% compound (1-1) and polyvinylpyrrolidone (PVP)
Figure 1D:
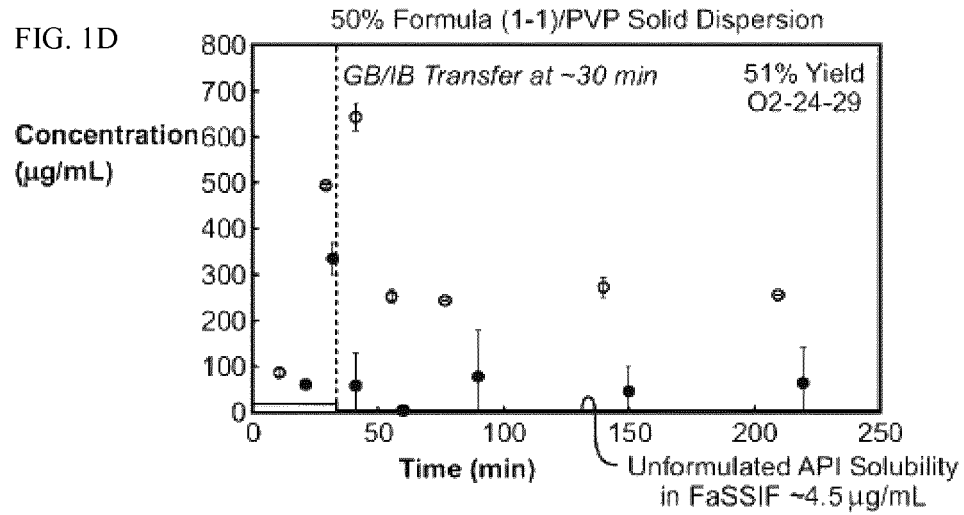
FIG. 1D illustrates dissolution profile of an exemplary formulation comprising a solid dispersion comprising 50% compound (1-1) and PVP.
Figure 1E:
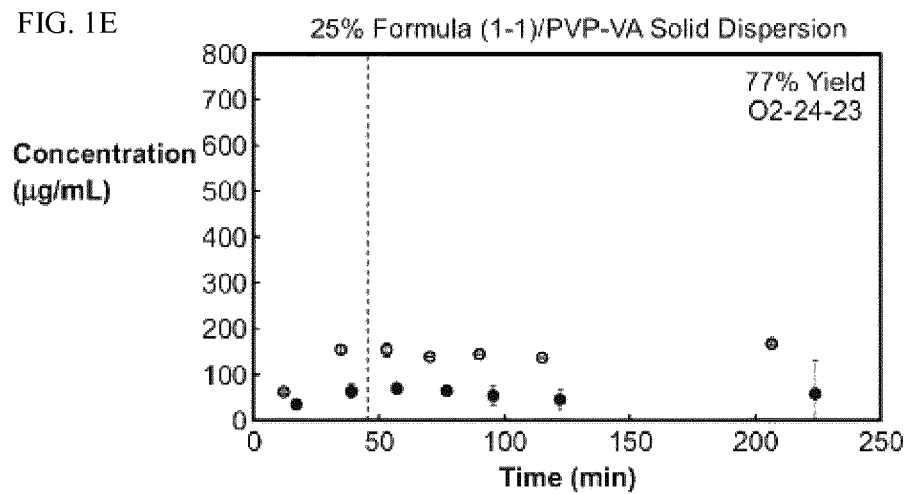
FIG. 1E illustrates dissolution profile of an exemplary formulation comprising a solid dispersion comprising 25% compound (1-1) and PVP-vinyl acetate (PVP-VA)
Figure 1F:
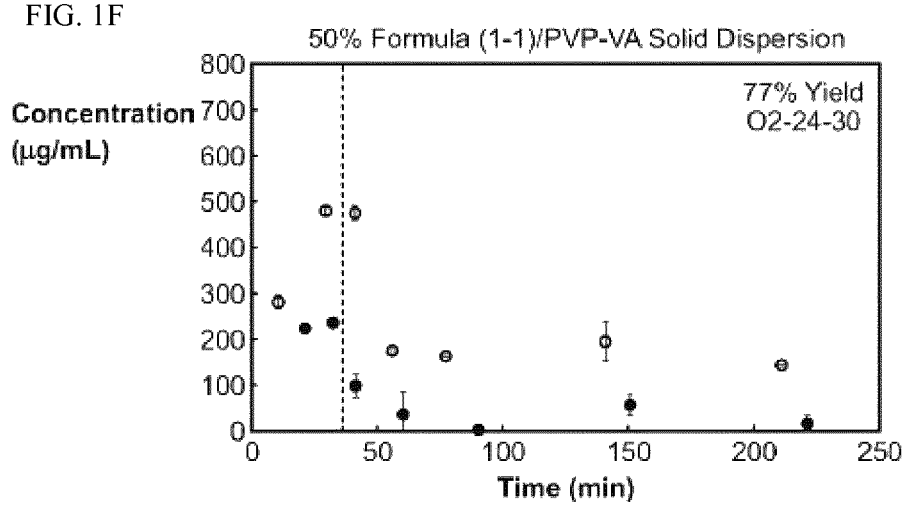
FIG. 1F illustrates dissolution profile of an exemplary formulation comprising a solid dispersion comprising 50% compound (1-1) and PVP-VA.
Figure 1G:
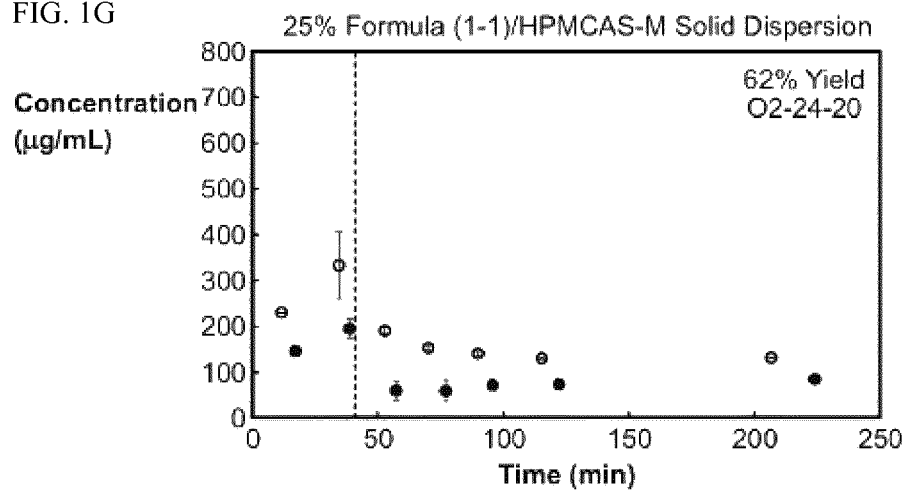
FIG. 1G illustrates dissolution profile of an exemplary formulation comprising a solid dispersion comprising 25% compound (1-1) and hypromellose acetate succinate (HPMCAS-M)
Figure 1H:
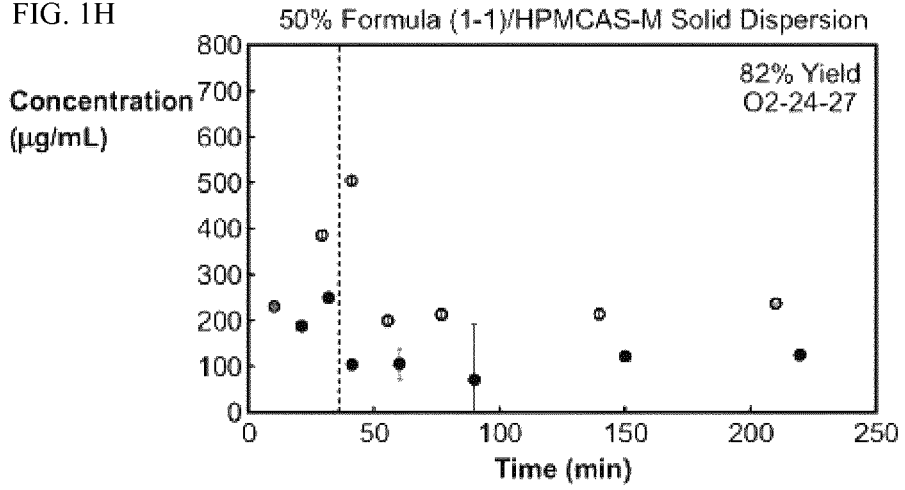
FIG. 1H illustrates dissolution profile of an exemplary formulation comprising a solid dispersion comprising 50% compound (1-1) and HPMCAS-M.
Figure 1I:
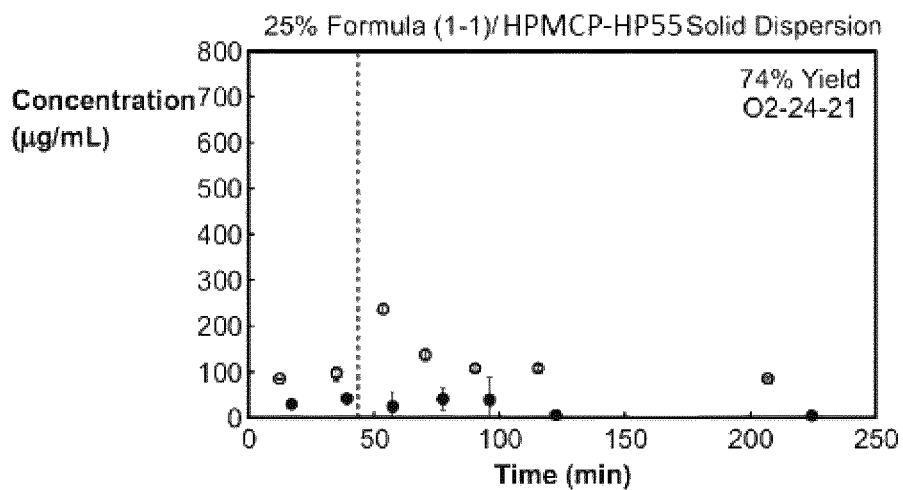
FIG. 1I illustrates dissolution profile of an exemplary formulation comprising a solid dispersion comprising 25% compound (1-1) and hypromellose phthalate (HPMCP-HP55)
Figure 1J:
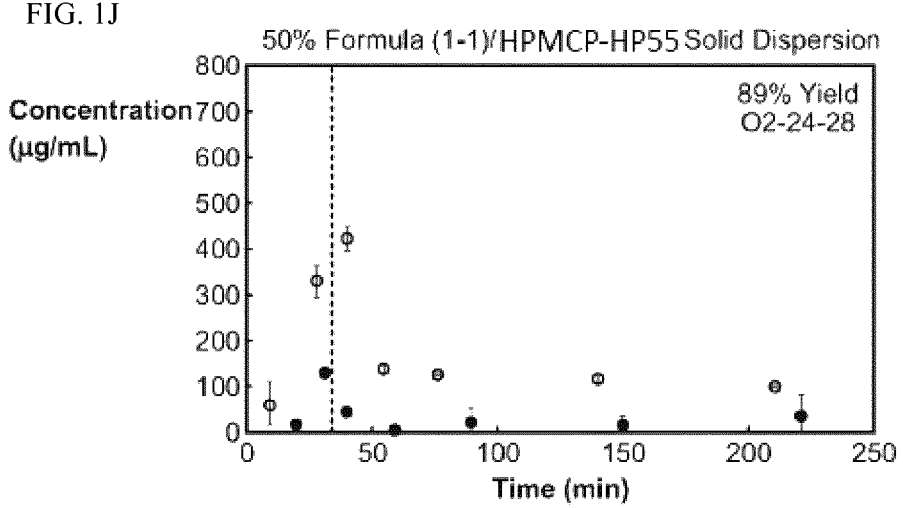
FIG. 1J illustrates dissolution profile of an exemplary formulation comprising a solid dispersion comprising 50% compound (1-1) and HPMCP-HP55.

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entireties.

I. Definitions

The term "alkyl group" as used herein refers to a saturated straight or branched hydrocarbon.

The term "substituted alkyl group" refers to an alkyl moiety having one or more substituents replacing a hydrogen or one or more carbons of the hydrocarbon backbone.

The term "alkenyl group" whether used alone or as part of a substituent group, for example, "$C_{1-4}$alkenyl(aryl)," refers to a partially unsaturated branched or straight chain monovalent hydrocarbon radical having at least one carbon-carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl(2-propenyl), butenyl and the like. Examples include $C_{2-8}$alkenyl or $C_{2-4}$alkenyl groups.

The term "$C_{(j-k)}$" (where j and k are integers referring to a designated number of carbon atoms) refers to an alkyl, alkenyl, alkynyl, alkoxy or cycloalkyl radical or to the alkyl portion of a radical in which alkyl appears as the prefix root containing from j to k carbon atoms inclusive. For example, $C_{(1-4)}$ denotes a radical containing 1, 2, 3 or 4 carbon atoms.

The terms "halo" or "halogen" as used herein refer to F, Cl, Br, or I.

The term "pharmaceutically acceptable salts" is art-recognized and refers to the relatively non-toxic, inorganic and organic acid addition salts, or inorganic or organic base addition salts of compounds, including, for example, those contained in compositions of the present invention.

The term "solid dispersion" as used herein refers to a group of solid products consisting of at least two different components, generally a hydrophilic carrier and a hydrophobic drug (active ingredient).

The term "chiral" is art-recognized and refers to molecules That have the property of non-superimposability of the mirror image partner, while the term "achiral" refers to molecules which are superimposable on their mirror image partner. A "prochiral molecule" is a molecule that has the potential to be converted to a chiral molecule in a particular process.

The symbol " ═══ " is used to denote a bond that may be a single, a double or a triple bond.

The term "enantiomer" as it used herein, and structural formulas depicting an enantiomer are meant to include the "pure" enantiomer free from its optical isomer as well as mixtures of the enantiomer and its optical isomer in which the enantiomer is present in an enantiomeric excess, e.g., at least 10%, 25%, 50%, 75%, 90%, 95%, 98%, or 99% enantiomeric excess.

The term "stereoisomers" when used herein consist of all geometric isomers, enantiomers or diastereomers. The present invention encompasses various stereoisomers of these compounds and mixtures thereof. Conformational isomers and rotamers of disclosed compounds are also contemplated.

The term "stereoselective synthesis" as it is used herein denotes a chemical or enzymatic reaction in which a single reactant forms an unequal mixture of stereoisomers during the creation of a new stereocenter or during the transformation of a pre-existing one, and are well known in the art. Stereoselective syntheses encompass both enantioselective and diastereoselective transformations. For examples, see Carreira, E. M. and Kvaerno, L., *Classics in Stereoselective Synthesis*, Wiley-VCH: Weinheim, 2009.

The term "spray drying" refers to processes which involve the atomization of the feed suspension or solution into small droplets and rapidly removing solvent from the mixture in a processor chamber where there is a strong driving force for the evaporation (e.g., hot dry gas or partial vacuum or combinations thereof).

The term "therapeutically effective amount" as used herein refers to any amount of a thienotriazolodiazepine of the present invention or any other pharmaceutically active agent which, as compared to a corresponding a patient who has not received such an amount of the thienotriazolodiazepine or the other pharmaceutically active agent, results in improved treatment, healing, prevention, or amelioration of a disease, disorder, or side effect, or a decrease in the rate of advancement of a disease or disorder.

The term "about" means+/−10%. In one embodiment, it means+/−5%.

Throughout this application and in the claims that follow, unless the context requires otherwise, the word "comprise", or variations such as "comprises" or "comprising", should be understood to imply the inclusion of a stated integer step or group of integers or steps but not the exclusion of any other integer or step or group of integers or steps. Moreover, the word "comprise" should be understood to imply "consist of".

It has now been found that thienotriazolodiazepine compound of Formula (1), described herein below, can be formulated as a solid dispersion with a pharmaceutically acceptable polymers, to provide an oral formulation that provides high absorption of the pharmaceutical ingredient into the circulation from the gastrointestinal tract. In one embodiment, the pharmaceutically acceptable polymer is hypromellose acetate succinate (also called hydroxypropylmethylcellulose acetate succinate or HPMCAS). In one embodiment, the pharmaceutically acceptable polymer is polyvinylpyrrolidone (PVP).

In some embodiments, the hydroxypropylmethyl cellulose acetate succinates (HPMCAS), may include M grade having 9% acetyl/11% succinoyl (e.g., HPMCAS having a mean particle size of 5 μm (i.e., HPMCAS-MF, fine powder grade) or having a mean particle size of 1 mm (i.e., HPMCAS-MG, granular grade)), H grade having 12% acetyl/6% succinoyl (e.g., HPMCAS having a mean particle size of 5 μm (i.e., HPMCAS-HF, fine powder grade) or having a mean particle size of 1 mm (i.e., HPMCAS-HG, granular grade)), and L grade having 8% acetyl/15% succinoyl (e.g., HPMCAS having a mean particle size of 5 μm (i.e., HPMCAS-LF, fine powder grade) or having a mean particle size of 1 mm (i.e., HPMCAS-LG, granular grade).

In some embodiments, the polyvinyl pyrrolidones may have molecular weights of about 2,500 (KOLLIDON®12 PF, weight-average molecular weight between 2,000 to 3,000), about 9,000 (KOLLIDON® 17 PF, weight-average molecular weight between 7,000 to 11,000), about 25,000 (KOLLIDON® 25, weight-average molecular weight between 28,000 to 34,000), about 50,000 (KOLLIDON® 30, weight-average molecular weight between 44,000 to 54,000), or about 1,250,000 (KOLLIDON® 90 or KOLLIDON® 90F, weight-average molecular weight between 1,000,000 to 1,500,000).

II. Methods of Treatment

In some embodiments, the present disclosure provides for methods of treating lymphoma using the compositions described herein. In some embodiments, the present disclosure provides for methods of treating diffuse large B-cell lymphoma (DLBCL) (e.g. DLBCL of an activated B-cell (ABC) subtype ("ABC-DLBCL"), or DLBCL of germinal center B-cell like (GCB) ("GCB-DLBCL") subtype) using the composition described herein.

In some embodiments, the present disclosure provides for methods of treating lymphoma in a mammal comprising: administering to a patient in need a pharmaceutically acceptable amount of a composition comprising a solid dispersion according to any of the compositions described in Sections III, IV, V and VI described herein. In some embodiments, the present disclosure provides for methods of treating DLBCL (e.g. ABC-DLBCL or GBC-DLBCL) in a mammal comprising: administering to a patient in need a pharmaceutically acceptable amount of a composition comprising a solid dispersion according to any of the compositions described in Sections III, IV, V and VI described herein. In some embodiments the DLBCL is selected from the group consisting of activated B-cell DLBCL (ABC-DLBCL) and germinal B-cell DLBCL (GBC-DLBCL).

In some embodiments, the present disclosure provides for methods of treating lymphoma in a mammal comprising: administering to a patient in need a pharmaceutically acceptable amount of a composition comprising a pharmaceutical formulation according to any of the compositions described in Sections III, IV, V and VI described herein. In some embodiments, the present disclosure provides for methods of treating DLBCL (e.g. ABC-DLBCL or GBC-DLBCL) in a mammal comprising: administering to a patient in need a pharmaceutically acceptable amount of a composition comprising a pharmaceutical formulation according to any of the compositions described in Sections III, IV, V and VI described herein. In some embodiments the DLBCL is selected from the group consisting of activated B-cell DLBCL (ABC-DLBCL) and germinal B-cell DLBCL (GBC-DLBCL).

In some embodiments, the present disclosure provides for a compound of Formula (1), in particular of Formula (1A), for use in treating lymphoma. In some embodiments, the present disclosure provides for a compound of Formula (1), in particular of Formula (1A), for use in treating DLBCL (e.g. ABC-DLBCL or GCB-DLBCL).

In some embodiments, the present disclosure provides for a solid dispersion according to any of the compositions described in Sections III, IV, V and VI described herein for use in treating lymphoma. In some embodiments, the present disclosure provides for a solid dispersion according to any of the compositions described in Sections III, IV, V and VI described herein for use in treating DLBCL (e.g. ABC-DLBCL or GCB-DLBCL).

In some embodiments, methods of treating lymphoma, including DLBCL (e.g. ABC-DLBCL or GBC-DLBCL) use thienotriazolodiazepine compound of the Formula (1)

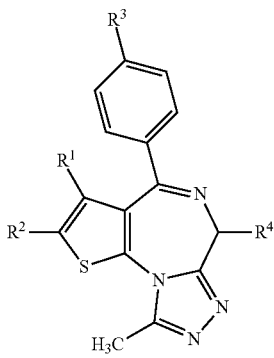

wherein
$R^1$ is alkyl having a carbon number of 1-4,
$R^2$ is a hydrogen atom; a halogen atom; or alkyl having a carbon number of 1-4 optionally substituted by a halogen atom or a hydroxyl group,
$R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and
$R^4$ is —$(CH_2)_a$—CO—NH—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4,
including any salts, isomers, enantiomers, racemates, hydrates, solvates, metabolites, and polymorphs thereof. In some embodiments, the DLBCL is selected from the group consisting of activated B-cell DLBCL (ABC-DLBCL) and germinal B-cell DLBCL (GBC-DLBCL)

In some embodiments, Formula (1) is selected from Formula (1A):

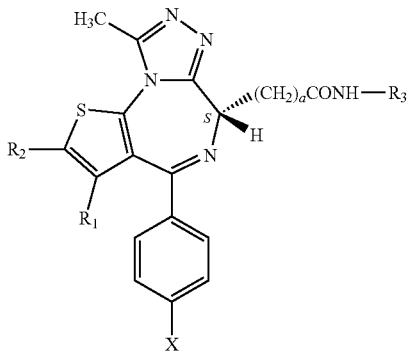

wherein X is a halogen, $R^1$ is $C_1$-$C_4$ alkyl, $R^2$ is $C_1$-$C_4$ alkyl, a is an integer of 1-4, $R^3$ is $C_1$-$C_4$ alkyl, $C_1$-$C_4$ hydroxyalkyl, $C_1$-$C_4$ alkoxy, phenyl optionally having substituent(s) as defined for $R^9$ in Formula (1), or heteroaryl optionally having substituent(s) as defined for $R^9$ in Formula (1), a pharmaceutically acceptable salt thereof or a hydrate thereof.

In one such embodiment, the thienotriazolodiazepine compound is formulated as a solid dispersion comprising an amorphous thienotriazolodiazepine compound and a pharmaceutically acceptable polymer.

In some embodiments the lymphoma is Hodgkin lymphoma or non-Hodgkin lymphoma. In some embodiments the lymphoma is selected from the group consisting of diffuse large B-cell lymphoma (DLBCL), mantle cell lymphoma, multiple myeloma, splenic marginal zone lymphoma, and prolymphocytic leukemia. In some embodiments the DLBCL is DLBCL of an activated B-cell (ABC) subtype ("ABC-DLBCL"), or germinal center B-cell like diffuse large B-cell lymphoma (GCB) ("GCB-DLBCL").

In one embodiment of the method of treatment of the present invention, administering to a patient in need of such treatment a pharmaceutically acceptable amount of a composition in accordance with the present invention causes upregulation (over expression) of histones in lymphoma cells. In one embodiment of the method of treatment of the present invention, administering to a patient in need of such treatment a pharmaceutically acceptable amount of a composition in accordance with the present invention causes upregulation (over expression) of histones in DLBCL (e.g. ABC-DLBCL or GBC-DLBCL) cells.

In one embodiment of the method of treatment of the present invention, administering to a patient in need of such treatment a pharmaceutically acceptable amount of a composition in accordance with the present invention activates at least one of MYC target genes in lymphoma cells. In one embodiment of the method of treatment of the present invention, administering to a patient in need of such treatment a pharmaceutically acceptable amount of a composition in accordance with the present invention activates at least one of MYC target genes in DLBCL (e.g. ABC-DLBCL or GBC-DLBCL) cells.

In one embodiment of the method of treatment of the present invention, administering to a patient in need of such treatment a pharmaceutically acceptable amount of a composition in accordance with the present invention downregulates MYC gene in lymphoma cells. In one embodiment of the method of treatment of the present invention, administering to a patient in need of such treatment a pharmaceutically acceptable amount of a composition in accordance with the present invention downregulates MYC gene in DLBCL (e.g. ABC-DLBCL or GBC-DLBCL) cells.

In one embodiment of the method of treatment of the present invention, administering to a patient in need of such treatment a pharmaceutically acceptable amount of a composition in accordance with the present invention downregulates at least one member of the NFKB, TLR and JAK/STAT pathways in lymphoma cells. In one embodiment of the method of treatment of the present invention, administering to a patient in need of such treatment a pharmaceutically acceptable amount of a composition in accordance with the present invention downregulates at least one member of the NFKB, TLR and JAK/STAT pathways in DLBCL (e.g. ABC-DLBCL or GBC-DLBCL) cells. In an embodiment, members of the NFKB, TLR, and JAK/STAT pathways are selected from the group consisting of MYD88, IRAK1, TLR6, IL6, STAT3, and TNFRSF17.

In one embodiment of the method of treatment of the present invention, administering to a patient in need of such treatment a pharmaceutically acceptable amount of a composition in accordance with the present invention downregulates at least one NFKB target gene in lymphoma cells. In one embodiment of the method of treatment of the present invention, administering to a patient in need of such treatment a pharmaceutically acceptable amount of a composition in accordance with the present invention downregulates at least one NFKB target gene in DLBCL (e.g. ABC-DLBCL or GBC-DLBCL) cells.

In one embodiment of the method of treatment of the present invention, administering to a patient in need of such treatment a pharmaceutically acceptable amount of a composition in accordance with the present invention downregulates at least one of NFKB target genes selected from the group consisting of iRF4, TNFAIP3 and BIRC3, in lymphoma cells. In one embodiment of the method of treatment of the present invention, administering to a patient in need of such treatment a pharmaceutically acceptable amount of a composition in accordance with the present invention downregulates at least one NFKB target gene selected from the group consisting of iRF4, TNFAIP3 and BIRC3, in DLBCL (e.g. ABC-DLBCL or GBC-DLBCL) cells.

The present disclosure also provides for a method of treating lymphoma in a mammal comprising: obtaining cancer cells from a patient; determining a gene expression profile for the cancer cells; administering to the patient a pharmaceutically acceptable amount of a composition comprising a thienotriazolodiazepine compound of Formula (1), wherein the gene expression profile of the patient's cancer cells is positive for at least one gene associated with sensitivity to the thienotriazolodiazepine compound of the Formula (1). In particular, in an embodiment of the invention Formula (1) may be Formula (1A). The lymphoma may be DLBCL (e.g. ABC-DLBCL or GBC-DLBCL). The at least one gene may be selected from the group consisting of members of the NFKB, TLR and JAK/STAT pathways. Members of the NFKB, TLR, and JAK/STAT pathways may be selected from the group consisting of MYD88, IRAK1, TLR6, IL6, STAT3, and TNFRSF17.

In some embodiments, the present invention provides a method of treating diffuse large B-cell lymphoma (DLBCL) of an activated B-cell (ABC) subtype or DLBCL of germinal center B cell-like (GCB) subtype in a mammalian subject, wherein the method comprises the step of: (i) administering a thienotriazolodiazepine compound or a pharmaceutically acceptable salt, hydrate, or solvate thereof to a mammalian subject in an amount that reduces (downregulates) expression of an oncomir (also oncomiR) selected from the group consisting of miR-92a-1-5p, miR-21-3p, and a combination thereof. In some embodiments of the method of treating diffuse large B-cell lymphoma (DLBCL) of an activated B-cell (ABC) subtype or DLBCL of germinal center B cell-like (GCB) subtype, the administered thienotriazolodiazepine compound or a pharmaceutically acceptable salt, hydrate, or solvate thereof further increases (downregulates) expression of the tumor suppressor miR-96-5p.

In some embodiments, the present invention provides a method of treating diffuse large B-cell lymphoma (DLBCL) of an activated B-cell (ABC) subtype or DLBCL of germinal center B cell-like (GCB) subtype in a mammalian subject, wherein the method comprises the step of: (i) administering a thienotriazolodiazepine compound or a pharmaceutically acceptable salt, hydrate, or solvate thereof to a mammalian subject in an amount that increases (upregulates) expression of the tumor suppressor miR-96-5p. In some embodiments of the method of treating diffuse large B-cell lymphoma (DLBCL) of an activated B-cell (ABC) subtype or DLBCL of germinal center B cell-like (GCB) subtype, the administered thienotriazolodiazepine compound or a pharmaceutically acceptable salt, hydrate, or solvate thereof further reduces (downregulates) expression of an oncomir (also oncomiR) selected from the group consisting of miR-92a-1-5p, miR-21-3p, and a combination thereof.

In some embodiments, the present invention provides a method of treating diffuse large B-cell lymphoma (DLBCL) of an activated B-cell (ABC) subtype or DLBCL of germinal center B cell-like (GCB) subtype in a mammalian subject, wherein the cells of the DLBCL exhibit decreased levels of micro RNA selected from the group consisting of miR-92a-1-5p, miR-21-3p or combinations thereof upon exposure to the thienotriazolodiazepine compound of the Formula (1).

In some embodiments, the present invention provides a method of treating diffuse large B-cell lymphoma (DLBCL) of an activated B-cell (ABC) subtype or DLBCL of germinal center B cell-like (GCB) subtype in a mammalian subject, wherein the cells of the DLBCL exhibit increased levels of micro RNA miR-96-5p upon exposure to the thienotriazolodiazepine compound of the Formula (1).

A mammalian subject as used herein can be any mammal. In one embodiment, the mammalian subject includes, but is not limited to, a human; a non-human primate; a rodent such as a mouse, rat, or guinea pig; a domesticated pet such as a cat or dog; a horse, cow, pig, sheep, goat, or rabbit. In one embodiment, the mammalian subject includes, but is not limited to, a bird such as a duck, goose, chicken, or turkey. In one embodiment, the mammalian subject is a human. In one embodiment, the mammalian subject can be either gender and can be any age.

In some embodiments the present disclosure provides for methods of treating lymphoma comprising administering a thienotriazolodiazepine compound of the Formula (1) in combination with another therapeutic agent. In some embodiments the other therapeutic agent is a drug selected from the group consisting of m-TOR inhibitors BTK inhibitors, DNA methyltransferase inhibitors, immunomodulatory agents, DNA alkylating agents (e.g. nitrogen mustards, nitrosureas, alkyl sulfonates, triazines, and ethylenimines), histone deacetylase inhibitors (also known as HDAC inhibitors or HDIs), all-trans retinoic acid (also known as ATRA), doxorubicin, and esters, derivatives, prodrugs, salts, and complexes thereof. In some embodiments the present disclosure provides for methods of treating DLBCL (e.g., ABC-DLBCL or GBC-DLBCL) comprising administering a thienotriazolodiazepine compound of the Formula (1) in combination with another therapeutic agent. In some embodiments the other therapeutic agent is a drug selected from the group consisting of m-TOR inhibitors, BTK inhibitors, DNA methyltransferase inhibitors, immunomodulatory agents, DNA alkylating agents (e.g. nitrogen mustards, nitrosureas, alkyl sulfonates, triazines, and ethylenimines), histone deacetylase inhibitors (also known as HDAC inhibitors or HDIs), all-trans retinoic acid (also known as ATRA), doxorubicin, and esters, derivatives, prodrugs, salts, and complexes thereof.

In some embodiments the present disclosure provides for methods of treating lymphoma comprising administering a thienotriazolodiazepine compound of the Formula (1A) in combination with another therapeutic agent. In some embodiments the other therapeutic agent is a drug selected from the group consisting of m-TOR inhibitors, BTK inhibitors, DNA methyltransferase inhibitors, immunomodulatory agents, DNA alkylating agents (e.g. nitrogen mustards, nitrosureas, alkyl sulfonates, triazines, and ethylenimines), histone deacetylase inhibitors (also known as HDAC inhibitors or HDIs), all-trans retinoic acid (also known as ATRA), doxorubicin, and esters, derivatives, prodrugs, salts, and complexes thereof. In some embodiments the present disclosure provides for methods of treating DLBCL (e.g., ABC-DLBCL or GBC-DLBCL) comprising administering a thienotriazolodiazepine compound of the Formula (1A) in combination with another therapeutic agent. In some embodiments the other therapeutic agent is a drug selected from the group consisting of m-TOR inhibitors BTK inhibitors, DNA methyltransferase inhibitors, immunomodulatory agents, DNA alkylating agents (e.g. nitrogen mustards, nitrosureas, alkyl sulfonates, triazines, and ethylenimines), histone deacetylase inhibitors (also known as HDAC inhibitors or HDIs), all-trans retinoic acid (also known as ATRA), doxorubicin, and esters, derivatives, prodrugs, salts, and complexes thereof.

In another embodiment, the compound of compound (1-1) or the pharmaceutically acceptable salt thereof is administered with another therapeutic agent, wherein the other therapeutic agent is selected from the group consisting of everolimus, ibrutinib, decitabine, lenalidomide, all-trans retinoic acid, romidepsin, bendamustine, and doxorubicin. In another embodiment, the compound of compound (1-1) or the pharmaceutically acceptable salt thereof is administered with another therapeutic agent, wherein the other therapeutic agent is everolimus. In another embodiment, the compound of compound (1-1) or the pharmaceutically acceptable salt thereof is administered with another therapeutic agent, wherein the other therapeutic agent is ibrutinib. In another embodiment, the compound of compound (1-1) or the pharmaceutically acceptable salt thereof is administered with another therapeutic agent, wherein the other therapeutic agent is decitabine. In another embodiment, the compound of compound (1-1) or the pharmaceutically acceptable salt thereof is administered with another therapeutic agent, wherein the other therapeutic agent is lenalidomide. In another embodiment, the compound of compound (1-1) or the pharmaceutically acceptable salt thereof is administered with another therapeutic agent, wherein the other therapeutic agent is all-trans retinoic acid. In another embodiment, the compound of compound (1-1) or the pharmaceutically acceptable salt thereof is administered with another therapeutic agent, wherein the other therapeutic agent is romidepsin. In another embodiment, the compound of compound (1-1) or the pharmaceutically acceptable salt thereof is administered with another therapeutic agent, wherein the other therapeutic agent is bendamustine. In another embodiment, the compound of compound (1-1) or the pharmaceutically acceptable salt thereof is administered with another therapeutic agent, wherein the other therapeutic agent is doxorubicin.

In some embodiments the method further comprises administering to the patient an mTOR inhibitor. In one such embodiment the mTOR inhibitor is selected from the group consisting of rapamycin, temsirolimus, ridaforolimus, everolimus, and esters, derivatives, prodrugs, salts, and complexes thereof. In one such embodiment the mTOR inhibitor is everolimus. The thienotriazolodiazepine compound and the mTOR inhibitor can be administered simultaneously or sequentially. In some embodiments the thienotriazolodiazepine compound is administered before the mTOR inhibitor, while in other embodiments the thienotriazolodiazepine compound is administered after the mTOR inhibitor. In some embodiments such combination of thienotriazolodiazepine compound and mTOR inhibitor produces a synergistic effect.

Example mammalian target of rapamycin (mTOR) inhibitors for use in combination with the thienotriazolodiazepine of Formula (1) in the methods of the present invention include, but are not limited to, the mTOR inhibitors listed in the below Table A.

TABLE A

Exemplary mTOR inhibitor compounds which may be used in combination with thienotriazolodiazepine of Formula (1):

| No. | Inhibitor Name | Description | Literature Citations |
|---|---|---|---|
| 1 | BEZ235 (NVP-BEZ235) | BEZ235 (NVP-BEZ235) is a dual ATP-competitive PI3K and mTOR inhibitor of p110α, p110γ, p110δ and p110β with IC50 of 4 nM, 5 nM, 7 nM and 75 nM, respectively, and also inhibits ATR with IC50 of 21 nM. | Nature, 2012, 487(7408):505-9; Blood, 2011, 118(14), 3911-3921; Cancer Res, 2011, 71(15), 5067-5074. |
| 2 | Everolimus (RAD001) | Everolimus (RAD001) is an mTOR inhibitor of FKBP12 with IC50 of 1.6-2.4 nM. | Cell, 2012, 149(3):656-70;; Cancer Cell, 2012, 21(2), 155-167; Clin Cancer Res, 2013, 19(3):598-609. |
| 3 | Rapamycin (Sirolimus, AY22989, NSC226080) | Rapamycin (Sirolimus, AY-22989, WY-090217) is a specific mTOR inhibitor with IC50 of ~0.1 nM. | Cancer Cell, 2011, 19(6), 792-804;; Cancer Res, 2013, ;Cell Res, 2012, 22(6): 1003-21. |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 4 | AZD8055 | AZD8055 is a novel ATP-competitive inhibitor of mTOR with IC50 of 0.8 nM. | Autophagy, 2012, Am J Transplant, 2013, ;Biochem Pharmacol, 2012, 83(9), 1183-1194 |
| 5 | PI-103<br>3-[4-(4-Morpholinylpyrido[3',2':4,5]f-uro[3,2-d]pyrimidin-2-yl] phenol | PI-103 is a potent, ATP-competitive PI3K inhibitor of DNA-PK, p110α, mTORC1, PI3KC2β, p110δ, mTORC2, p110β, and p110γ with IC50 of 2 nM, 8 nM, 20 nM, 26 nM, 48 nM, 83 nM, 88 nM and 150 nM, respectively. | Leukemia, 2013, 27(3):650-60; Leukemia, 2012, 26(5):927-33; Biochem Pharmacol, 2012, 83(9), 1183-1194. |
| 6 | Temsirolimus (CCI-779, NSC-683864) | Temsirolimus (CCI-779, Torisel) is a specific mTOR inhibitor with IC50 of 1.76 μM. | Autophagy, 2011, 7(2), 176-187; Tuberc Respir Dis (Seoul), 2012, 72(4), 343-351; PLoS One, 2013, 8(5):e62104. |
| 7 | Ku-0063794<br>rel-5-[2-[(2R,6S)-2,6-dimethyl-4-mo-rpholinyl]-4-(4-morpholinyl)pyrido[2,3-d]pyrimidin-7-yl]-2-methoxybenzenemethanol | KU-0063794 is a potent and highly specific mTOR inhibitor for both mTORC1 and mTORC2 with IC50 ~10 nM. | Cell Stem Cell, 2012, 10(2):210-7; Circ Res, 2010, 107(10), 1265-1274; J Immunol, 2013, 190(7), 3246-55. |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 8 | GDC-0349 | GDC-0349, is a potent and selective ATP-competitive inhibitor of mTOR with Ki of 3.8 nM. | |
| 9 | Torin 2<br>9-(6-Amino-3-pyridinyl)-1-[3-(trifl-uoromethyl)phenyl]-benzo[h]-1,6-naphthyridin-2(1H)-one | Torin 2 is a highly potent and selective mTOR inhibitor with IC50 of 0.25 nM, and also exhibits potent cellular activity against ATM/ATR/DNA-PK with EC50 of 28 nM, 35 nM and 118 nM, respectively. | |
| 10 | INK 128 (MLN-0128) | INK 128 is a potent and selective mTOR inhibitor with IC50 of 1 nM. | |
| 11 | AZD2014 | AZD2014 is a novel dual mTORC1 and mTORC2 inhibitor with potential antineoplastic activity. | |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 12 | NVP-BGT226(BGT226) | NVP-BGT226 is a novel dual PI3K/mTOR inhibitor with IC50 of 1 nM. | |
| 13 | PF-04691502 | PF-04691502 is an ATP-competitive, selective inhibitor of PI3K(α/β/δ/γ)/mTOR with Ki of 1.8 nM/ 2.1 nM/1.6 nM/ 1.9 nM and 16 nM, also inhibits Akt phosphorylation on T308/S473 with IC50 of 7.5 nM/3.8 nM. | |
| 14 | CH5132799 | CH5132799 exhibits a strong inhibitory activity especially against PI3Kα with IC50 of 14 nM and also inhibits mTOR with IC50 of 1.6 μM. | |
| 15 | GDC-0980 (RG7422) | GDC-0980 (RG7422) is a potent, selective inhibitor of PI3Kα, PI3Kβ, PI3Kδ and PBKγ with IC50 of 5 nM, 27 nM, 7 nM, and 14 nM, and also a mTOR inhibitor with Ki of 17 nM. | |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 16 | Torin 1<br><br>1-[4-[4-(1-Oxopropyl)-1-piperazinyl-]-3-(trifluoromethyl)phenyl]-9-(3-quinolinyl)-benz-o[h]-1,6-naphthyridin-2(1H)-one | Torin1 is a potent inhibitor of mTOR with IC50 of 2-10 nM. | |
| 17 | WAY-600 | WAY-600 is a potent, ATP-competitive and selective inhibitor of mTOR with IC50 of 9 nM. | |
| 18 | WYE-125132(WYE-132) | WYE-125132 is a highly potent, ATP-competitive and specific mTOR inhibitor with IC50 of 0.19 nM. | |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 19 | WYE-687 | WYE-687 is an ATP-competitive and selective inhibitor of mTOR with IC50 of 7 nM. | |
| 20 | GSK2126458(GSK458) | GSK2126458 is a highly selective and potent inhibitor of p110α, p110β, p110γ, p110δ, mTORC1 and mTORC2 with Ki of 0.019 nM, 0.13 nM, 0.024 nM, 0.06 nM, 0.18 nM and 0.3 nM, respectively. | |
| 21 | PF-05212384 (PKI-587) | PKI-587 is a highly potent dual inhibitor of PI3Kα, PI3Kγ and mTOR with IC50 of 0.4 nM, 5.4 nM and 1.6 nM, respectively. | |
| 22 | PP-121<br>1-Cyclopentyl-3-(1H-pyrrolo[2,3-b]p-yridin-5-yl)-1H-pyrazolo[3,4-d]pyrimidin-4-amine | PP-121 is a multi-target inhibitor of PDGFR, Hck, mTOR, VEGFR2, Src and Abl with IC50 of 2 nM, 8 nM, 10 nM, 12 nM, 14 nM and 18 nM, respectively, and also inhibits DNA-PK with IC50 of 60 nM. | |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 23 | OSI-027(ASP4786) | OSI-027 is a selective and potent dual inhibitor of mTORC1 and mTORC2 with IC50 of 22 nM and 65 nM, respectively. | Exp Eye Res, 2013, 113C, 9-18 |
| 24 | Palomid 529(P529) | Palomid 529 inhibits both the mTORC1 and mTORC2 complexes, reduces phosphorylation of pAktS473, pGSK3βS9, and pS6 but neither pMAPK nor pAktT308. Phase 1. | |
| 25 | PP242<br>2-[4-Amino-1-(1-methylethyl)-1H-pyr-azolo[3,4-d]pyrimidin-3-yl]-1H-indol-5-ol | PP242 is a selective mTOR inhibitor with IC50 of 8 nM. | Autophagy, 2012, 8(6), 903-914 |
| 26 | XL765(SAR245409) | XL765 is a dual inhibitor of mTOR/PI3k for mTOR, p110α, p110β, p110γ, p110δ, with IC50 of 157 nM, 39 nM, 113 nM, 9 nM and 43 nM, respectively. | Endocrinology, 2013, 154(3):1247-59 |

TABLE A-continued

Exemplary mTOR inhibitor compounds which may be used in combination with thienotriazolodiazepine of Formula (1):

| No. | Inhibitor Name | | Description | Literature Citations |
|---|---|---|---|---|
| 27 | GSK1059615<br>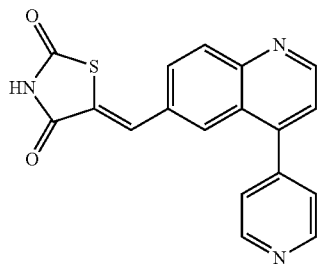 [SMILES: O=C1NC(=O)/C(=C/c2ccc3nccc(-c4ccncc4)c3c2)S1]<br>5-[[4-(4-Pyridinyl)-6-quinolinyl]me-thylene]-2,4-thiazolidenedione | | GSK1059615 is a novel and dual inhibitor of PI3Kα, PI3Kβ, PI3Kδ, PI3Kγ and mTOR with IC50 of 0.4 nM, 0.6 nM, 2 nM, 5 nM and 12 nM, respectively. | Nature, 2012, 486(7404), 532-536 |
| 28 | WYE-354<br>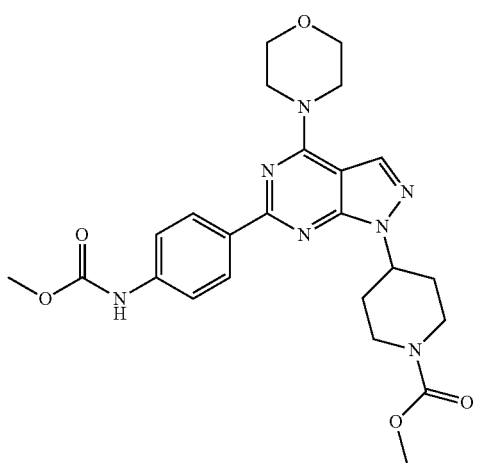 [SMILES: COC(=O)Nc1ccc(-c2nc(N3CCOCC3)c3cnn(C4CCN(C(=O)OC)CC4)c3n2)cc1] | | WYE-354 is a potent, specific and ATP-compctitive inhibitor of mTOR with IC50 of 5 nM. | Mol Cancer Res, 2012, 10(6), 821-833. |
| 29 | Deforolimus (Ridaforolimus, MK-8669)<br>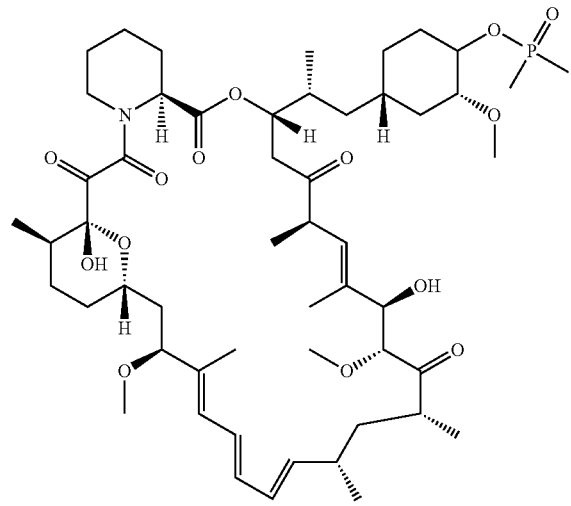 | | Deforolimus (Ridaforolimus; AP23573; MK-8669; 42-(Dimethylphosphinate) rapamycin; Ridaforolimus) is a selective mTOR inhibitor with IC50 of 0.2 nM. | Mol Genet Meta, 2010, 100(4), 309-315. |

In some embodiments the method further comprises administering to the patient a BTK inhibitor. In one such embodiment the BTK inhibitor is selected from the group consisting of ibrutinib, and esters, derivatives, prodrugs, salts, and complexes thereof. The thienotriazolodiazepine compound and the BTK inhibitor can be administered simultaneously or sequentially. In some embodiments the thienotriazolodiazepine compound is administered before the BTK inhibitor, while in other embodiments the thienotriazolodiazepine compound is administered after the BTK inhibitor. In some embodiments such combination of thienotriazolodiazepine compound and BTK inhibitor produces a synergistic effect.

Example BTK inhibitor drugs for use in combinations with the thienotriazolodiazepine compounds of Formula (1) in the methods of the present invention include the BTK inhibitors listed in the below Table B.

TABLE B

| Inhibitor Name | Inhibitor Information | Literature Citations |
| --- | --- | --- |
| PCI-32765 (Ibrutinib) | PCI-32765 (Ibrutinib) is a potent and highly selective Btk inhibitor with IC50 of 0.5 nM. | Cancer Cell, 2012, 22(5): 656-67. Blood, 2012, 120(19), 3978-3985; Cell Signal, 2013, 25(1):106-12. |
| GDC-0834 | GDC-0834 is a novel potent and selective BTK inhibitor with IC50 of 5.9 nM. | J. Hematol. Oncol. 2013 Aug. 19; 6:59; |
| RN-486 | | J. Hematol. Oncol. 2013 Aug. 19; 6:59; |

TABLE B-continued

| Inhibitor Name | Inhibitor Information | Literature Citations |
|---|---|---|
| CGI-560 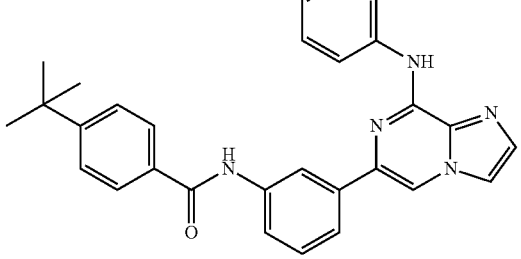 | | J. Hematol. Oncol. 2013 Aug. 19; 6:59; |
| CGI-1746 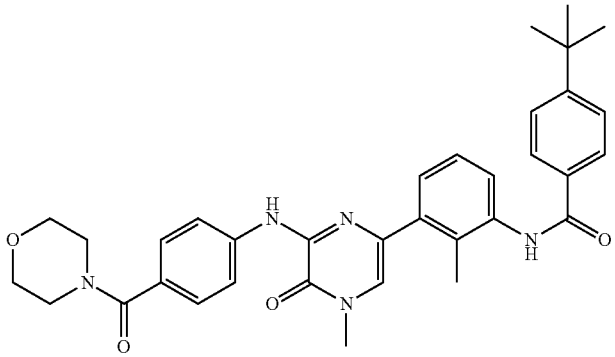 | | J. Hematol. Oncol. 2013 Aug. 19; 6:59; |
| LFM-A13 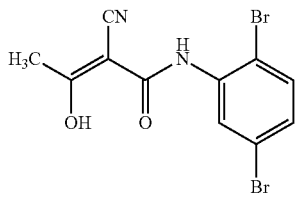 | Bruton's tyrosine kinase (BTK) inhibitor IC50 = 2.5 μM. IC50's for JAK-1, JAK-2, JAK-3, SYK, HCK, EGFR kinase, IR kinase all >300 μM | J. Hematol. Oncol. 2013 Aug. 19; 6:59; |
| Terreic acid 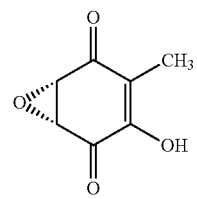 (1R,6S)-3-Hydroxy-4-methyl-7-oxabicyclo[4.1.0]hept-3-ene-2,5-dione | Selective inhibitor of Bruton's tyrosine kinase (BTK). Inhibits the catalytic activity of BTK as well as the interaction between BTK and PKCβII, in intact cells and in cell-free systems, without affecting the activity of PKC. Terreic acid has little or no effect on the activities of Lyn, Syk, PKa, casein kinase I, ERK1, ERK2 and p38 kinase. A useful tool in studying the role of BTK in cellular signaling. | |

TABLE B-continued

| Inhibitor Name | Inhibitor Information | Literature Citations |
|---|---|---|
| CC-292 | | J. Pharmacol. Exp. Ther. 2013 August; 346(2): 219-228; Leukemia 2014 Mar. 7 (epub); J. Hematol. Oncol. 2013 Aug. 19; 6:59; |
| CNX-774 | | J. Hematol. Oncol. 2013 Aug. 19; 6:59; |
| Dasatinib | | N Eng J Med; 2006 Jun. 15; 354(24): 2531-41 |
| QL47 | | ACS Chem Biol; 2013 Mar. 17 |

In some embodiments the method further comprises administering to the patient a DNA methyltransferase inhibitor. In one such embodiment the DNA methyltransferase inhibitor is selected from the group consisting of azacitidine, decitabine, and esters, derivatives, prodrugs, salts, and complexes thereof. In one such embodiment the DNA methyltransferase inhibitor is decitabine. The thienotriazolodiazepine compound and the DNA methyltransferase inhibitor can be administered simultaneously or sequentially. In some embodiments the thienotriazolodiazepine compound is administered before the DNA methyltransferase inhibitor, while in other embodiments the thienotriazolodiazepine compound is administered after the DNA methyltransferase inhibitor. In some embodiments such combination of thienotriazolodiazepine compound and DNA methyltransferase inhibitor produces a synergistic effect.

Example DNA methyltransferase inhibitors for use in combinations with the thienotriazolodiazepine compounds of Formula (1) in the methods of the present invention include the compounds listed in the below Table C.

TABLE C
| Inhibitor Name | Inhibitor Information | Literature Citations |
|---|---|---|
| decitabine (5-aza-2'-deoxycytidine) 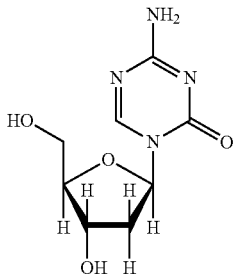 | | J Natl Cancer Inst 2005; 97:1498-1506 |
| 5-azacytidine 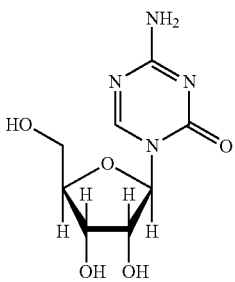 | | Experientia 1964; 20:202-3; Cell 1980; 20:85-93; J Natl Cancer Inst 2005;97:1498-1506 |
| zebularin 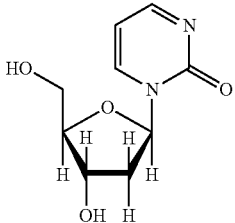 | | J Natl Cancer Inst 2005;97:1498-1506 |
| RG108 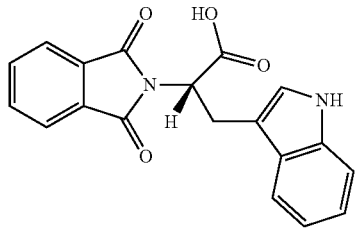 | | J Natl Cancer Inst 2005;97:1498-1506 |

TABLE C-continued

| Inhibitor Name | Inhibitor Information | Literature Citations |
|---|---|---|
| epigallocatechin-3-gallate (EGCG) | *[structure]* | J Natl Cancer Inst 2005;97:1498-1506 |
| procaine | *[structure]* | J Natl Cancer Inst 2005;97:1498-1506 |

In some embodiments the method further comprises administering to the patient an immunomodulatory agent. In some embodiments, the immunomodulator (also referred herein as an "immunomodulatory agent") can be selected from the group consisting of thalidomide, lenalidomide, pomalidomide, and esters, derivatives, prodrugs, salts, and complexes thereof. In one such embodiment the immunomodulatory agent is lenalidomide. The thienotriazolodiazepine compound and the immunomodulatory agent can be administered simultaneously or sequentially. In some embodiments the thienotriazolodiazepine compound is administered before the immunomodulatory agent while in other embodiments the thienotriazolodiazepine compound is administered after the immunomodulatory agent. In some embodiments such combination of thienotriazolodiazepine compound and immunomodulatory agent produces a synergistic effect.

Suitable immunomodulatory agents for use in combinations with the thienotriazolodiazepine compounds of Formula (1) in the methods of the present invention include the immunomodulatory agents listed in the below Table D.

TABLE D

| No. | Immunomodulatory Agent Name | Structure |
|---|---|---|
| 1 | thalidomide (Inmunoprin, Talidex, Talizer, Thalomid) | *[structure]* |
| 2 | lenalidomide (CC-5013, Revlimid) | *[structure]* |
| 3 | pomalidomide (CC-4047, Pomalyst) | *[structure]* |

In some embodiments, the DNA alkylating agent can be selected from the group consisting of nitrogen mustards, nitrosureas, alkylsulfonates, triazines, and ethylenimines. In one such embodiment the nitrogen mustard is selected from the group consisting of bendamustine, methchlorethamine, chlorambucil, cyclophosphamide, ifosfamide, melphalan, and esters, derivatives, prodrugs, salts, and complexes thereof. In one such embodiment the nitrogen mustard is selected from the group consisting of bendamustine, methchlorethamine, chlorambucil, cyclophosphamide, ifosfamide, melphalan, and esters, derivatives, prodrugs, salts, and complexes thereof. In one such embodiment the DNA alkylating agent is bendamustine. In some embodiments the nitrosurea is selected from the group consisting of streptozocin, carmustine, lomustine, and esters, derivatives, prodrugs, salts, and complexes thereof. In some embodiments the alkyl sulfonate is busulfan or an ester, derivative, prodrug, salt, or complex thereof. In some embodiments the triazine is selected from the group consisting of dacarbazine, temozolomide, and esters, derivatives, prodrugs, salts, and complexes thereof. In some embodiments the ethylenimine is selected from the group consisting of thiotepa, altretamine, and esters, derivatives, prodrugs, salts, and complexes thereof. The thienotriazolodiazepine compound and the DNA alkylating agent can be administered simultaneously or sequentially. In some embodiments the thienotriazolodiazepine compound is administered before the DNA alkylating agent, while in other embodiments the thienotriazolodiazepine compound is administered after the DNA alkylating agent. In some embodiments such combination of thienotriazolodiazepine compound and the DNA alkylating agent produces a synergistic effect.

Suitable DNA alkylating agents for use in combinations with the thienotriazolodiazepine compounds of Formula (1) in the methods of the present invention include the immunomodulatory agents listed in the below Table E.

TABLE E

| No. | DNA alkylating agent | Structure |
|---|---|---|
| 1 | bendamustine (also known as TREAKISYM ®, RIBOMUSTIN ®, LEVACT ®, TREANDA ®; SDX-105, or 4-[5-[Bis(2-chloroethyl)amino]-1-methylbenzimidazol-2-yl]butanoic acid) | 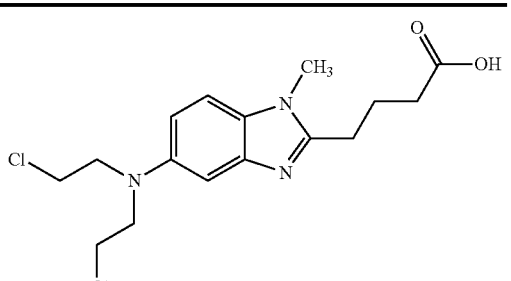 |
| 2 | methchlorethamine (nitrogen mustard, chlormethine, mustine, HN2, Embichin, or Bis(2-chloroethyl)methylamine) | 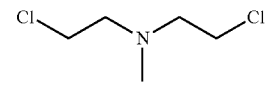 |
| 3 | chlorambucil (LEUKERAN ®, 4-[bis(2-chlorethyl)amino]benzenebutanoic acid) | 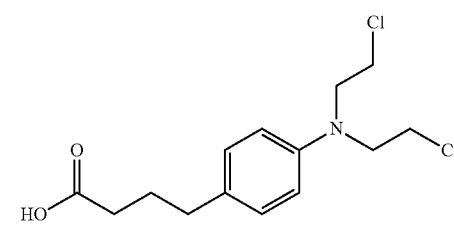 [SMILES: O=C(O)CCCc1ccc(N(CCCl)CCCl)cc1] |
| 4 | cyclophosphamide (also known as CYTOXAN ®, ENDOXAN ®, NEOSAR ®, PROCYTOX ®, REVIMMUNE ®, CYCLOBLASTIN ®, cytophosphane, CP, and (RS)-N,N-bis(2-chloroethyl)-1,3,2-oxazaphosphinan-2-amine 2-oxide) | 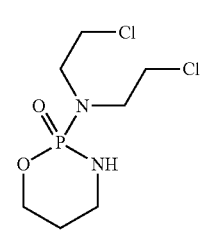 [SMILES: O=P1(N(CCCl)CCCl)NCCCO1] |
| 5 | ifosfamide (also known as IFEX ® or N-3-bis(2-chloroethyl)-1,3,2-oxazaphosphinan-2-amide-2-oxide) | 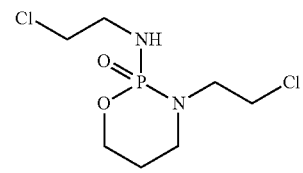 [SMILES: O=P1(NCCCl)OCCCN1CCCl] |
| 6 | melphalan (also known as ALKERAN ®, L-Phenylalanine Mustard, L-PAM, or 4-[bis(chloroethyl)amino]phenylalanine) | 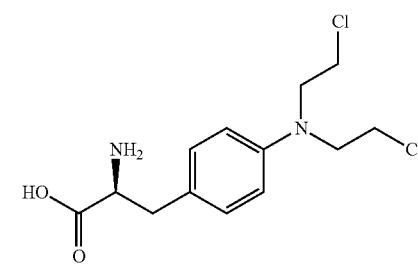 [SMILES: N[C@@H](Cc1ccc(N(CCCl)CCCl)cc1)C(=O)O] |

TABLE E-continued

| No. | DNA alkylating agent | Structure |
|---|---|---|
| 7 | streptozocin (also known as STZ, Zanosar ®, or 2-Deoxy-2-({[methyl(nitroso)amino]carbonyl} amino)-β-D-glucopyranose) | 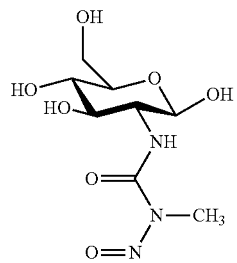 |
| 8 | carmustine (also known as bis-chloroethylnitrosourea, BCNU, BiCNU, 1,3-Bis(2-chloroethyl)-1-nitrosourea, or N,N'-Bis(2-chloroethyl)-N-nitroso-urea) | 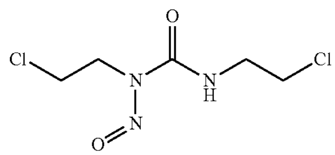 [SMILES: O=NN(CCCl)C(=O)NCCCl] |
| 9 | lomustine (also known as CCNU; CeeNU, or N-(2-chloroethyl)-N'-cyclohexyl-N-nitrosourea) | 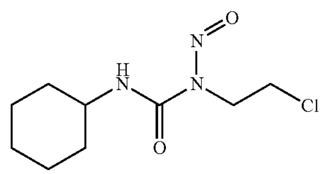 [SMILES: O=NN(CCCl)C(=O)NC1CCCCC1] |
| 10 | dacarbazine (also known as DTIC, DTIC-Dome; DIC, Imidazole Carboxamide, or 5-(3,3-Dimethyl-1-triazenyl)imidazole-4-carboxamide) | 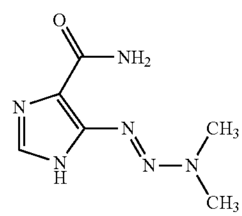 |
| 11 | temozolomide (also known as Temodal, Temcad, TEMODAR ®, or 4-methyl-5-oxo-2,3,4,6,8-pentazabicyclo[4.3.0]nona-2,7,9-triene-9-carboxamide) | 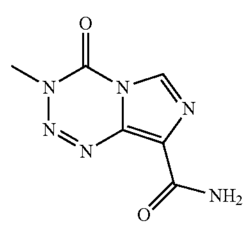 |
| 12 | thiotepa (also known as N,N'N''-triethylenethiophosphoramide or 1,1',1''-phosphorothioyltriaziridine) | 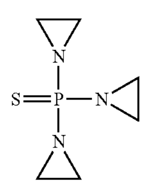 [SMILES: S=P(N1CC1)(N1CC1)N1CC1] |
| 13 | altretamine (also known as hexamethylmelamine, hexalen, or N2,N2,N4,N4,N6,N6-hexamethyl-1,3,5-triazine-2,4,6-triamine) | 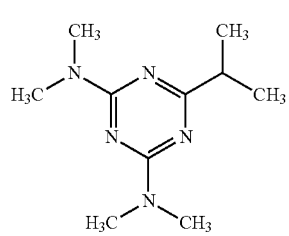 |

In some embodiments the method further comprises administering to the patient a histone deacetylase inhibitor. In some embodiments, the histone deacetylase inhibitor (also referred herein as an "HDAC inhibitor" or "HDI") can be selected from the group consisting of romidepsin, vorinostat, entinostat, panobinostat, and esters, derivatives, prodrugs, salts, and complexes thereof. In one such embodiment the HDAC inhibitor is romidepsin. The thienotriazolodiazepine compound and the HDAC inhibitor can be administered simultaneously or sequentially. In some embodiments the thienotriazolodiazepine compound is administered before the HDAC inhibitor while in other embodiments the thienotriazolodiazepine compound is administered after the HDAC inhibitor. In some embodiments such combination of thienotriazolodiazepine compound and the HDAC inhibitor produces a synergistic effect.

Suitable HDAC inhibitors for use in combinations with the thienotriazolodiazepine compounds of Formula (1) in the methods of the present invention include the immunomodulatory HDAC inhibitors listed in the below Table F.

TABLE F

| Inhibitor Name | Inhibitor Information | Literature Citations |
|---|---|---|
| Vorinostat (SAHA, MK0683) | Vorinostat (suberoylanilide hydroxamic acid, SAHA, Zolinza) is an HDAC inhibitor with IC50 of ~10 nM. | Nature, 2011, 471(7337):235-9; Nat Biotechnol, 2011, 29(3), 255-265; J Exp Med, 2012, 209(1):35-50. |
| Entinostat (MS-275, SNDX-275) | MS-275 is an HDAC inhibitor of HDAC1 and HDAC3 with IC50 of 0.51 µM and 1.7 µM, respectively. | Nat Biotechnol, 2011, 29(3), 255-265; Proc Natl Acad Sci USA, 2011, 108(49):19629-34; Circ Res, 2012, 110(5):739-48. |
| Panobinostat (LBH589, NVP-LBH589) | LBH589 (Panobinostat) is a novel broad-spectrum HDAC inhibitor with IC50 of 5 nM and 20 nM in MOLT-4 and Reh cells, respectively. | Nat Biotechnol, 2011, 29(3), 255-265; Blood, 2012, 119(6):1450-8; Acta Neuropathol, 2011, 122(5):637-50 |
| Trichostatin A (TSA) | Trichostatin A (TSA) is an HDAC inhibitor with IC50 of ~1.8 nM. | Plant J, 2013, 74(5), 815-828; Epigenetics, 2012, 7(10), 1161-1172. |
| Mocetinostat (MGCD0103, MG0103) 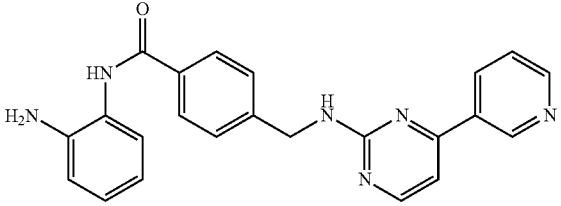 | MGCD0103 (Mocetinostat) is a potent HDAC inhbitor for HDAC1, HDAC2 and HDAC3 with IC50 of 0.15 µM, 0.29 µM and 1.66 µM, respectively. | Nat Struct Mol Biol, 2013, 20(3):317-25; Circ Res, 2012, 110(5):739-48; Oncogene, 2011, 30(27), 3062-3072. |
| Belinostat (PXD101) | Belinostat (PXD101) is a novel HDAC inhibitor with IC50 of 27 nM in HeLa cell extracts. | Nat Biotechnol, 2011, 29(3), 255-265; Breast Cancer Res Treat, 2011, 131(3), 777-789; PLoS One, 2011, 6(2), e17138. |
| MC1568 | MC1568 is a selective HDAC inhibitor with IC50 of 200 nM. | Proc Natl Acad Sci USA, 2012, 109(34):E228493; Oncogene, 2013,; J Biol Chem, 2011, 286(27), 23842-23851. |

TABLE F-continued

| Inhibitor Name | Inhibitor Information | Literature Citations |
|---|---|---|
| LAQ824 (NVP-LAQ824, Dacinostat) 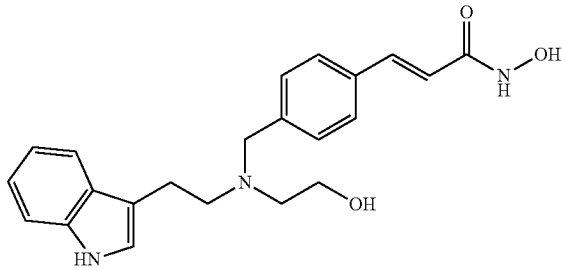 | LAQ824 (NVP-LAQ824) is a novel HDAC inhibitor with IC50 of 32 nM. | Nat Biotechnol, 2011, 29(3), 255-265; Diabetologia, 2012, 55(9):2421-31; Mol Pain, 2010, 6, 51. |
| ITF2357 (Givinostat) | ITF2357 (Givinostat) is a potent inhibitor of HDAC with IC50 of 7.5-16 nM. | J Neurosci, 2013, 33(17), 7535-7547. |
| Tubastatin A HCl 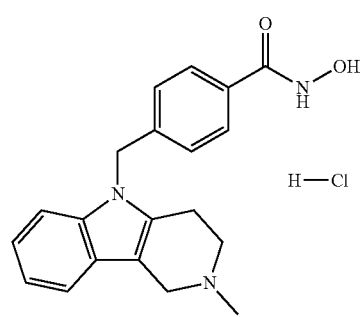 | Tubastatin A is a potent HDAC6 inhibitor with IC50 of 15 nM. | |
| CUDC-101 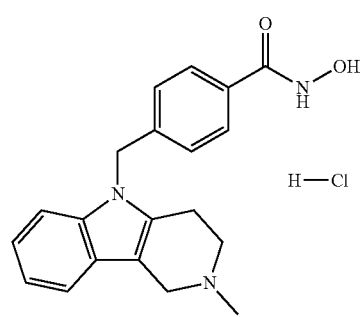 | CUDC-101 is a potent multi-target inhibitor targeting HDAC, EGFR and HER2 with IC50 of 4.4 nM, 2.4 nM, and 15.7 nM, respectively. | |
| SB939 (Pracinostat) 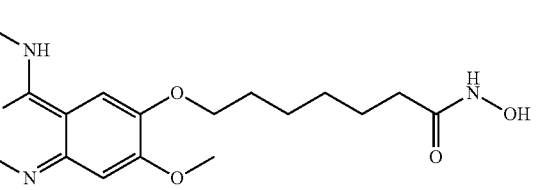 (E)-3-(2-butyl-1-(2-(diethylamino)ethyl)-1H-benzo[d]imidazol-5-yl)-N-hydroxyacrylamide | SB939 is a potent HDA inhibitor with IC50 of 40-140 nM. | Antimicrob Agents Chemother, 2012, 56(7), 3849-3856 |

TABLE F-continued

| Inhibitor Name | Inhibitor Information | Literature Citations |
|---|---|---|
| Droxinostat 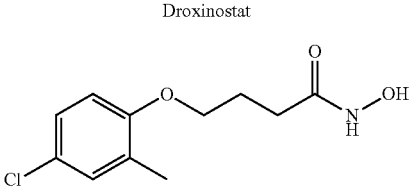 4-(4-Chloro-2-methylphenoxy)-N-hydroxybutanamide | Droxinostat (CMH, 5809354) is a selective inhibitor of HDAC3, HDAC6 and HDAC8 with IC50 of 16.9 μM, 2.47 μM and 1.46 μM, respectively. | Nat Struct Mol Biol, 2013, 20(3):317-25 |
| JNJ-26481585 (Quisinostat) 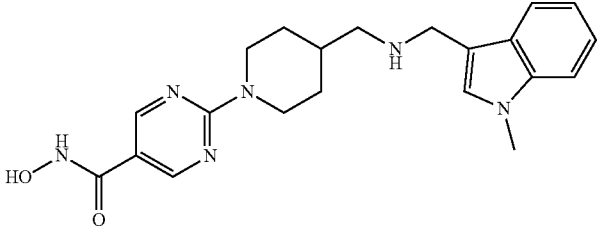 N-hydroxy-2-(4-((((1-methyl-1H-indol-3-yl)methyl)amino)methyl)piperidin-1-yl)pyrimidine-5-carboxamide | JNJ-26481585 (Quisinostat) is an HDAC inhibitor for HDAC1, HDAC2, HDAC4, HDAC10 and HDAC11 with IC50 of 0.11 nM, 0.33 nM, 0.64 nM, 0.46 nM and 0.37 nM, respectively. | |
| PCI-24781(CRA-024781) | PCI-24781 (CRA-024781) is a novel broad spectrum HDAC inhibitor targeting HDAC1, HDAC2, HDAC3, HDAC6, HDAC8 and HDAC10 with Ki or 7 nM, 19 nM, 8.2 nM, 17 nM, 280 nM, 24 nM, respectively. | PLoS One, 2013, 8(5), e65369; Nat Biotechnol, 2011 29(3), 255-265. |
| Romidepsin (FK228, depsipeptide) 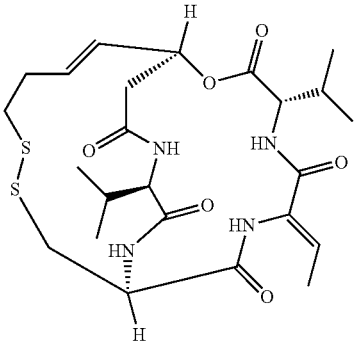 | Romidepsin (FK228, FR901228, depsipeptide, NSC 630176) is a potent HDAC1 and HDAC2 inhibitor with IC50 of 36 nM and 47 nM, respectively. (1S,4S,7Z,10S,16E,21R)-7-ethylidene-4,21-bis(1methylethyl)-2-oxa-12,13-dithia-5,8,20,23-tetraazabicyclo[8.7.6]tricos-16ene-3,6,9,22-pentone | J Neurosci, 2013, 33(17):7535-7547; Br J Haematol, 2013. |
| AR-42 (OSU-HDAC42) 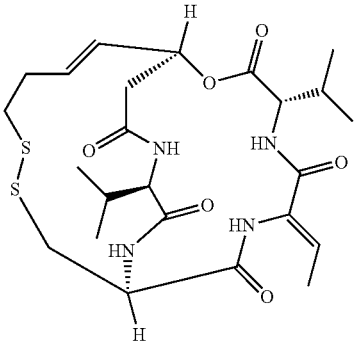 (S)-N-hydroxy-4-(3-methyl-2-phenylbutanamido)benzamide | AR-42 (HDAC-42, OSU-HDAC42) is a pan-HDAC inhibitor with IC50 30 nM. | |

TABLE F-continued

| Inhibitor Name | Inhibitor Information | Literature Citations |
|---|---|---|
| Valproic acid sodium salt (Sodium valproate) | Valproic acid sodium salt (Sodium valproate) is a HDAC inhibitor with IC50 of 0.4 mM and also inhibits GABA-transaminase or succinic semialdehyde dehydrogenase. | J Neurosci, 2013, 33(17), 7535-7547. |
| PCI-34051 | PCI-34051 is a potent and specific HDAC8 inhibitor with IC50 of 10 nM | |
| CI994 (Tacedinaline) 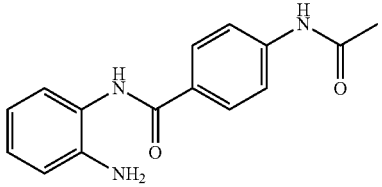 | CI994 (Tacedinaline) is an anti-cancer drug which inhibits HDAC1 with IC50 of 0.57 µM. | |
| M344 | M344 is a potent HDAC inhibitor with IC50 of 100 nM. | |
| PI3K/HDAC Inhibitor I | PI3K/HDAC Inhibitor I is a dual PI3K and HDAC inhibitor for PI3Kα, HDAC1, HDAC2, HDAC3 and HDAC10 with IC50 of 19 nM, 1.7 nM, 5 nM, 1.8 nM and 2.8 nM, respectively. | |
| Rocilinostat (ACY-1215) 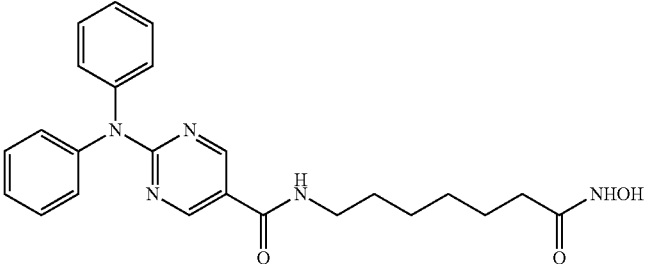 | Rocilinostat (ACY-1215) is a selective HDAC6 inhibitor with IC50 of 5 nM. | |
| Apicidin (OSI-2040) 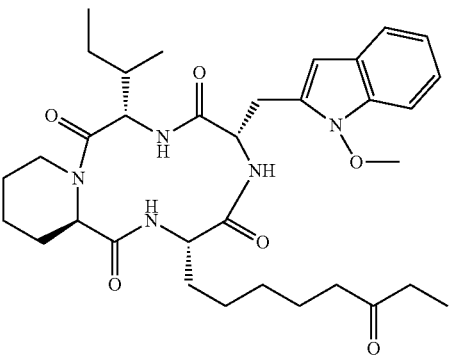 | Apicidin is a potent HDAC inhibitor with IC50 of 0.7 nM. (3S,6S,15aR)-9-((R)-sec-butyl)-6-((1-methoxy-1H-indol-2-yl)methyl)-3-(6-oxooctyl)decahydro-1H-pyrido[1,2-a][1,4,7,10]tetraaza-cyclododecine-1,4,7,10(12H)-tetraone | |
| Scriptaid | Scriptaid is an inhibitor of HDAC. | |

TABLE F-continued

| Inhibitor Name | Inhibitor Information | Literature Citations |
|---|---|---|
| Tubastatin A 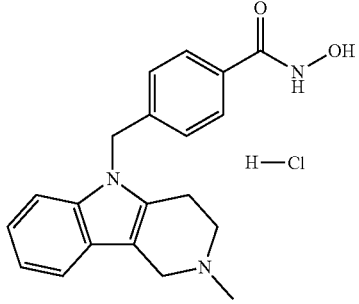 N-hydroxy-4-((2-methyl-3,4-dihydro-1H-pyrido[4,3-b]indol-5(2H)-yl)methyl)benzamide hydrochloride | Tubastatin A is a potent and selective inhibitor of HDAC6 with IC50 of 15 nM. | J Biol Chem, 2013, 288(20), 14400-7. |
| Sodium Phenylbutyrate 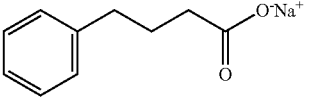 | Sodium Phenylbutyrate is a transcriptional regulators that act by altering chromatin structure via the modulation of HDAC activity. | |
| Resminostat (RAS2410) 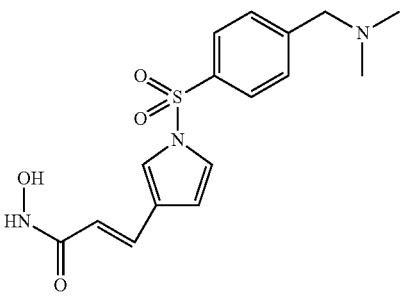 | (E)-3-(1-((4-((dimethylamino)methyl)phenyl)sulfonyl)-1H-pyrrol-3-yl)-N-hydroxyacrylamide | |

In some embodiments the method further comprises administering to the patient all-trans retinoic acid (also referred to as ATRA or tertinoin). The thienotriazolodiazepine compound and the all-trans retinoic acid can be administered simultaneously or sequentially. In some embodiments the thienotriazolodiazepine compound is administered before the all-trans retinoic acid while in other embodiments the thienotriazolodiazepine compound is administered after the all-trans retinoic acid. In some embodiments such combination of thienotriazolodiazepine compound and the all-trans retinoic acid produces a synergistic effect. Alternative names and the chemical structure of all-trans retinoic acid are provided in the below Table G.

TABLE G

| Name | Structure |
|---|---|
| all-trans retinoic acid (also known as ATRA, tretinoin, or 2E,4E,6E,8E)-3,7-dimethyl-9-(2,6,6-trimethylcyclohexen-1-yl)nona-2,4,6,8-tetraenoic acid) | 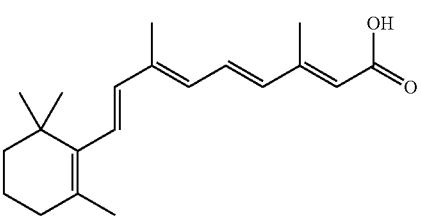 [SMILES: CC1=C(/C=C/C(C)=C/C=C/C(C)=C/C(=O)O)C(C)(C)CCC1] |

In some embodiments the method further comprises administering to the patient doxorubicin. The thienotriazolodiazepine compound and the doxorubicin can be administered simultaneously or sequentially. In some embodiments the thienotriazolodiazepine compound is administered before the doxorubicin while in other embodiments the thienotriazolodiazepine compound is administered after the doxorubicin. In some embodiments such combination of thienotriazolodiazepine compound and the doxorubicin produces a synergistic effect. Alternative names and the chemical structure of doxorubicin are provided in the below Table H.

TABLE H

| Name | Structure |
|---|---|
| doxorubicin (also known as hydroxydaunorubicin, hydroxydaunomycin, ADRIAMYCIN ®, or (7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione) | 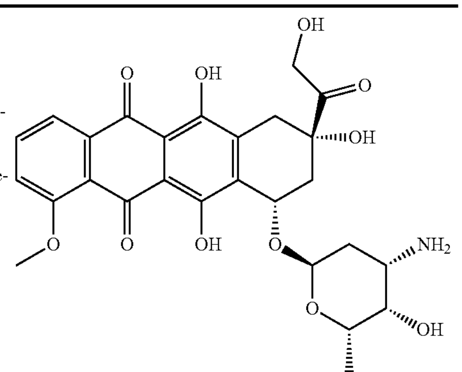 |

In one embodiment, the thienotriazolodiazepine compound of the Formula (1) is formed as a solid dispersion. In one embodiment, the solid dispersion comprises an amorphous thienotriazolodiazepine compound of the Formula (1) and a pharmaceutically acceptable polymer.

In the present invention, "treatment" or "treat" refers to an act or the action of administration of the active ingredient of the present invention to a person diagnosed by a doctor to have lymphoma (including DLBCL, e.g. ABC-DLBCL or GBC-DLBCL) or be at risk of developing lymphoma (including DLBCL, e.g. ABC-DLBCL or GBC-DLBCL) (patient), which aims, for example, to alleviate lymphoma (including DLBCL, e.g. ABC-DLBCL or GBC-DLBCL) or symptom, prevent the onset of lymphoma (including DLBCL, e.g. ABC-DLBCL or GBC-DLBCL) or symptom, or restore the state before onset of the lymphoma (including DLBCL, e.g. ABC-DLBCL or GBC-DLBCL).

III. Thienotriazolodiazepine Compounds

In one embodiment, the thienotriazolodiazepine compounds, used in the formulations of the present invention, are represented by Formula (1):

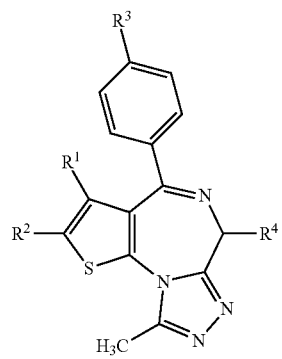

(1)

wherein $R^1$ is alkyl having a carbon number of 1-4, $R^2$ is a hydrogen atom; a halogen atom; or alkyl having a carbon number of 1-4 optionally substituted by a halogen atom or a hydroxyl group, $R^3$ is a halogen atom; phenyl optionally substituted by a halogen atom, alkyl having a carbon number of 1-4, alkoxy having a carbon number of 1-4 or cyano; $-NR^5-(CH_2)_m-R^6$ wherein $R^5$ is a hydrogen atom or alkyl having a carbon number of 1-4, m is an integer of 0-4, and $R^6$ is phenyl or pyridyl optionally substituted by a halogen atom; or $-NR^7-CO-(CH_2)_n-R^8$ wherein $R^7$ is a hydrogen atom or alkyl having a carbon number of 1-4, n is an integer of 0-2, and $R^8$ is phenyl or pyridyl optionally substituted by a halogen atom, and $R^4$ is $-(CH_2)_a-CO-NH-R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or $-(CH_2)_b-COOR^{10}$ wherein b is an integer of 1-4, and $R^{10}$ is alkyl having a carbon number of 1-4, including any salts, isomers, enantiomers, racemates, hydrates, solvates, metabolites, and polymorphs thereof.

In one embodiment, a suitable alkyl group includes linear or branched alkyl radicals including from 1 carbon atom up to 4 carbon atoms. In one embodiment, a suitable alkyl group includes linear or branched alkyl radicals including from 1 carbon atom up to 3 carbon atoms. In one embodiment, a suitable alkyl group includes linear or branched alkyl radicals include from 1 carbon atom up to 2 carbon atoms. In one embodiment, exemplary alkyl radicals include, but are not limited to, methyl, ethyl, propyl, isopropyl, n-butyl, isobutyl, sec-butyl, tert-butyl. In one embodiment, exemplary alkyl groups include, but are not limited to, methyl, ethyl, propyl, isopropyl, 2-methyl-1-propyl, and 2-methyl-2-propyl.

In some embodiments, the present invention provides pharmaceutically acceptable salts, solvates, including hydrates, and isotopically-labeled forms of the thienotriazolodiazepine compounds described herein. In one embodiment, pharmaceutically acceptable salts of the thienotriazolodiazepine compounds include acid addition salts formed with inorganic acids. In one embodiment, pharmaceutically acceptable inorganic acid addition salts of the thienotriazolodiazepine include salts of hydrochloric, hydrobromic, hydroiodic, phosphoric, metaphosphoric, nitric and sulfuric acids. In one embodiment, pharmaceutically acceptable salts of the thienotriazolodiazepine compounds include acid addition salts formed with organic acids. In one embodiment, pharmaceutically acceptable organic acid addition salts of the thienotriazolodiazepine include salts of tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and 4-methyl benzenesulfonic acids.

The present invention provides pharmaceutically acceptable isotopically-labeled forms of the thienotriazodiazepine compounds, described herein, wherein one or more atoms are replaced by atoms having the same atomic number, but an atomic mass or mass number different from the atomic mass or mass number usually found in nature. Examples of isotopes suitable for inclusion in the thienotriazolodiazepine compounds include isotopes of hydrogen, e.g., $^{2}H$ and $^{3}H$, carbon, e.g., $^{11}C$, $^{13}C$ and $^{14}C$, chlorine, e.g., $^{36}Cl$, fluorine, e.g., $^{18}F$, iodine, e.g., $^{123}I$ and $^{125}I$, nitrogen, e.g., $^{13}N$ and $^{15}N$, oxygen, e.g., $^{15}O$, $^{17}O$ and $^{18}O$, and sulfur, e.g., $^{35}S$. Isotopically-labeled forms of the thienotriazolodiazepine compounds generally can be prepared by conventional techniques known to those skilled in the art.

Certain isotopically-labeled forms of the compound of Formula (1), for example those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. Substitution with heavier isotopes such as deuterium ($^{2}H$) may afford certain therapeutic advantages that result from greater metabolic stability, for example increased in vivo half-life or reduced dosage requirements, and hence may be preferred in some circumstances. Substitution with positron emitting isotopes, such as $^{11}C$, $^{18}F$, $^{15}O$, and $^{13}N$ can be used in Positron Emission Tomography (PET) studies for examining substrate receptor occupancy.

In some embodiments, the thienotriazolodiazepine compounds disclosed herein can exist in solvated as well as unsolvated forms with pharmaceutically acceptable solvents. It will be understood by those skilled-in the art that a solvate is a complex of variable stoichiometry formed by a solute (in this case, the thienotriazolodiazepine compounds described herein) and a solvent. It is preferred that such solvents not interfere with the biological activity of the solute (the thienotriazolodiazepine compounds). Examples of suitable solvents for solvate formation include, but are not limited to, water, methanol, dimethyl sulfoxide, ethanol and acetic acid. Suitably the solvent used is a pharmaceutically acceptable solvent. Suitably the solvent used is water. In one embodiment, pharmaceutically acceptable solvates of the thienotriazolodiazepine compounds, described herein, include ethanol solvate, a isopropanol solvate, a dioxolane solvate, a tetrahydrofuran solvate, a dimethyl sulfoxide solvate, tert-butanol solvate, 2-butanol solvate, dioxolane solvate, 1,3-Dimethyl-3,4,5,6-tetrahydro-2(1H)-pyrimidinone ("DMPU") solvate, 1,3-dimethylimidazolidinone ("DMI") solvate, and 1,3-dimethylimidazolidinone ("DMP") solvate, or mixtures thereof.

In some embodiments, the thienotriazolodiazepine compounds, described herein, may contain one or more chiral centers and/or double bonds and, therefore, may exist as geometric isomers, enantiomers or diastereomers. The enantiomer and diastereomers of the thienotriazolodiazepine compounds may be designated in accordance with the Cahn-Ingold-Prelog convention, which assigns an "R" or "S" descriptor to each stereocenter (also sometimes referred to as a chiral center) and an E or Z descriptor to each carbon-carbon double bond (to designate geometric isomers) so that the configuration of the entire molecule can be specified uniquely by including the descriptors in its systematic name.

In some embodiments, the thienotriazolodiazepine compounds, described herein, may exist as a racemic mixture, or racemate, which includes equal amounts of left- and right-handed enantiomers of a chiral molecule. Such a racemic mixture may be denoted by the prefix (±)- or dl-, indicating an equal (1:1) mixture of dextro and levo isomers. Also, the prefix rac- (or racem-) or the symbols RS and SR may be used to designate the racemic mixture.

Geometric isomers, resulting from the arrangement of substituents around a carbon-carbon double bond or arrangement of substituents around a cycloalkyl or heterocyclic ring, can also exist in the compounds of the present invention. In some embodiments, the symbol ≡≡≡ may be used to denote a bond that may be a single, double or triple bond. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of a plane of a ring are designated "cis/trans" or "Z/E."

In some embodiments, thienotriazolodiazepine compounds disclosed herein may exist in single or multiple crystalline forms or polymorphs. In one embodiment, a thienotriazolodiazepine compound disclosed herein comprises an amorphous form thereof. In one embodiment, a thienotriazolodiazepine compound disclosed herein comprises a single polymorph thereof. In another embodiment, a thienotriazolodiazepine compound disclosed herein comprises a mixture of polymorphs thereof. In another embodiment, the compound is in a crystalline form.

In some embodiments, thienotriazolodiazepine compounds disclosed herein may exist as a single enantiomers or in enatiomerically enriched forms. In one embodiment, a thienotriazolodiazepine compound disclosed herein exists in an enantiomeric excess of more than 80%. In one embodiment, a thienotriazolodiazepine compound disclosed herein exists in an enantiomeric excess of more than 90%. In one embodiment, a thienotriazolodiazepine compound disclosed herein exists in an enantiomeric excess of more than 98%. In one embodiment, a thienotriazolodiazepine compound disclosed herein exists in an enantiomeric excess of more than 99%. In some embodiments, a thienotriazolodiazepine compound disclosed herein exists in an enantiomeric excess selected from the group consisting of at least 10%, at least 25%, at least 50%, at least 75%, at least 90%, at least 95%, at least 98%, at least and at least 99% enantiomeric excess.

For a pair of enantiomers, enantiomeric excess (ee) of enantiomer E1 in relation to enantiomer E2 can be calculated using the following equation eq. (1):

$$\% \text{ enantiomeric excess of } E1 = \frac{(E1 - E2) \times 100\%}{(E1 + E2)} \qquad \text{eq. (1)}$$

Relative amounts of E1 and E2 can be determined by chiral high performance liquid chromatography (HPLC), nuclear magnetic resonance (NMR) or any other suitable methods. In some embodiments, purity of an enantiomeric compound may refer to the amount of the enantiomers E1 and E2, relative to the amount of other materials, which may notably include byproducts and/or unreacted reactants or reagents.

In some embodiments, thienotriazolodiazepine compounds of Formula (1) include, but are not limited to, the thienotriazolodiazepine compounds (1-1) to (1-18), which are listed in the following Table I.

Compound (1-1) of Table I may be referred to herein as OTX-015, OTX015, or Y803.

TABLE I

Exemplary compounds which may be used in the formulations described herein:

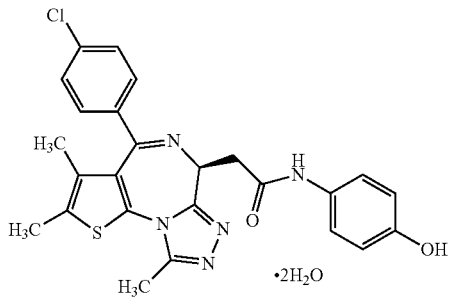 [SMILES: Cc1sc2c(c1C)C(c1ccc(Cl)cc1)=N[C@@H](CC(=O)Nc1ccc(O)cc1)c1nnc(C)n1-2]

(1-1)

TABLE I-continued

Exemplary compounds which may be used in the formulations described herein:

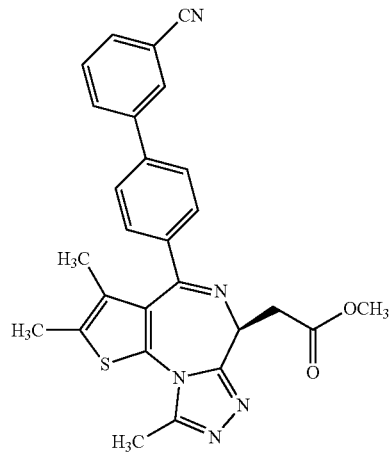 [SMILES: COC(=O)C[C@@H]1N=C(c2ccc(-c3cccc(C#N)c3)cc2)c2c(sc(C)c2C)-n2c(C)nnc21]

(1-2)

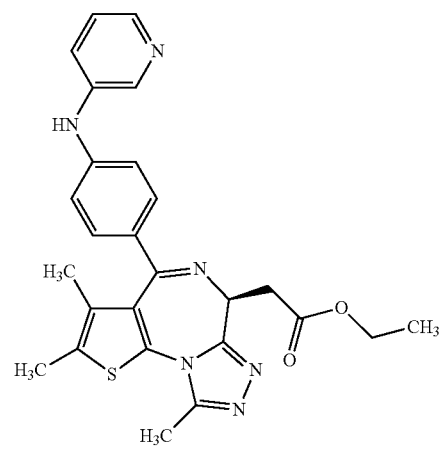 [SMILES: CCOC(=O)C[C@@H]1N=C(c2ccc(Nc3cccnc3)cc2)c2c(sc(C)c2C)-n2c(C)nnc21]

(1-3)

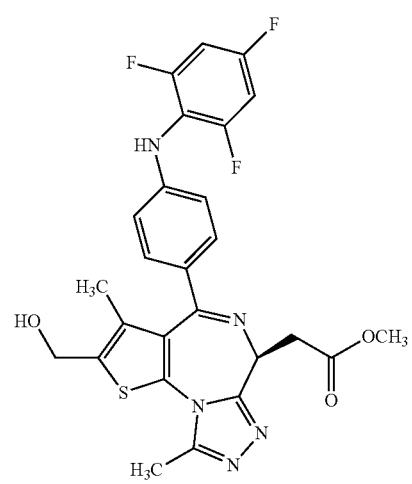 [SMILES: COC(=O)C[C@@H]1N=C(c2ccc(Nc3c(F)cc(F)cc3F)cc2)c2c(sc(CO)c2C)-n2c(C)nnc21]

(1-4)

TABLE I-continued
Exemplary compounds which may be used in the formulations described herein:
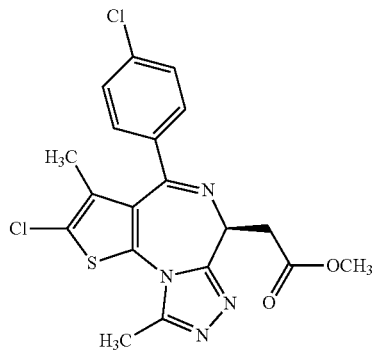 [SMILES: COC(=O)C[C@@H]1N=C(c2ccc(Cl)cc2)c2c(sc(Cl)c2C)-n2c(C)nnc21]
(1-5)
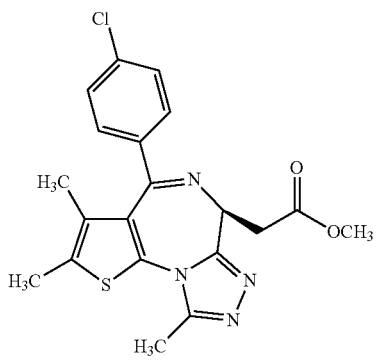 [SMILES: COC(=O)C[C@@H]1N=C(c2ccc(Cl)cc2)c2c(sc(C)c2C)-n2c(C)nnc21]
(1-6)
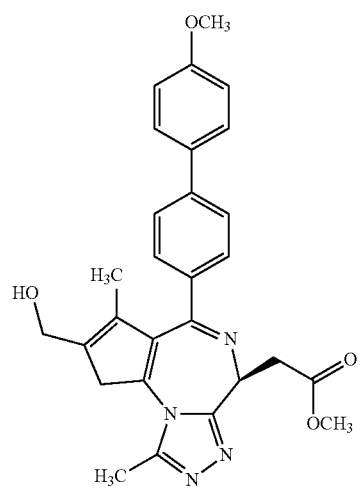 [SMILES: COC(=O)C[C@@H]1N=C(c2ccc(-c3ccc(OC)cc3)cc2)C2=C(CC(CO)=C2C)n2c(C)nnc21]
(1-7)
TABLE I-continued
Exemplary compounds which may be used in the formulations described herein:
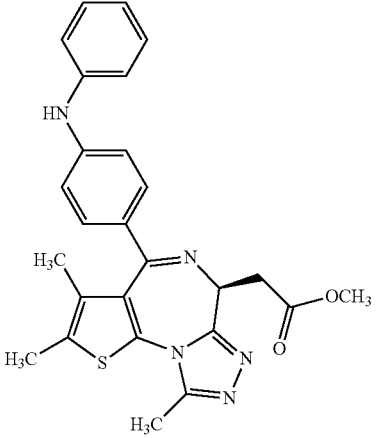 [SMILES: COC(=O)C[C@@H]1N=C(c2ccc(Nc3ccccc3)cc2)c2c(sc(C)c2C)-n2c(C)nnc21]
(1-8)
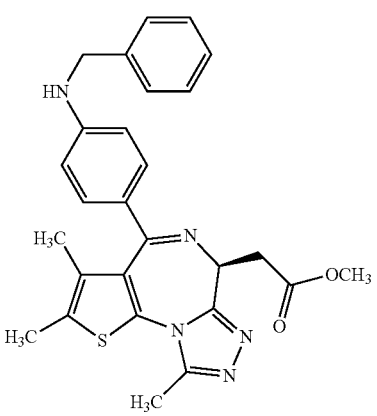 [SMILES: COC(=O)C[C@@H]1N=C(c2ccc(NCc3ccccc3)cc2)c2c(sc(C)c2C)-n2c(C)nnc21]
(1-9)
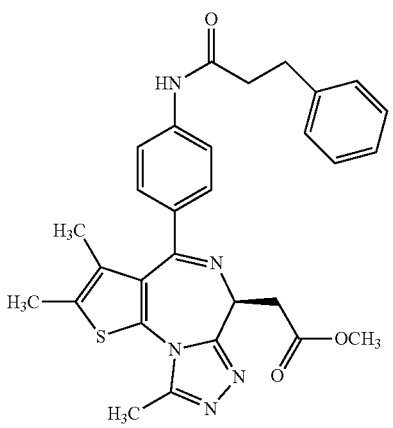 [SMILES: COC(=O)C[C@@H]1N=C(c2ccc(NC(=O)CCc3ccccc3)cc2)c2c(sc(C)c2C)-n2c(C)nnc21]
(1-10)

TABLE I-continued
Exemplary compounds which may be used in the formulations described herein:
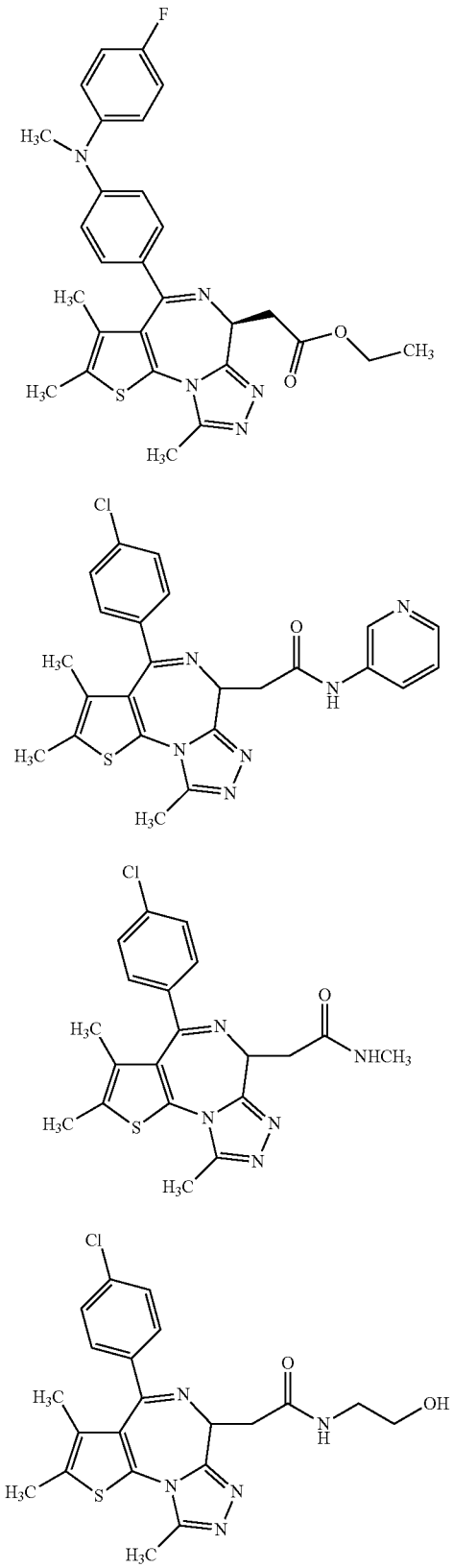
(1-11)
(1-12)
(1-13)
(1-14)
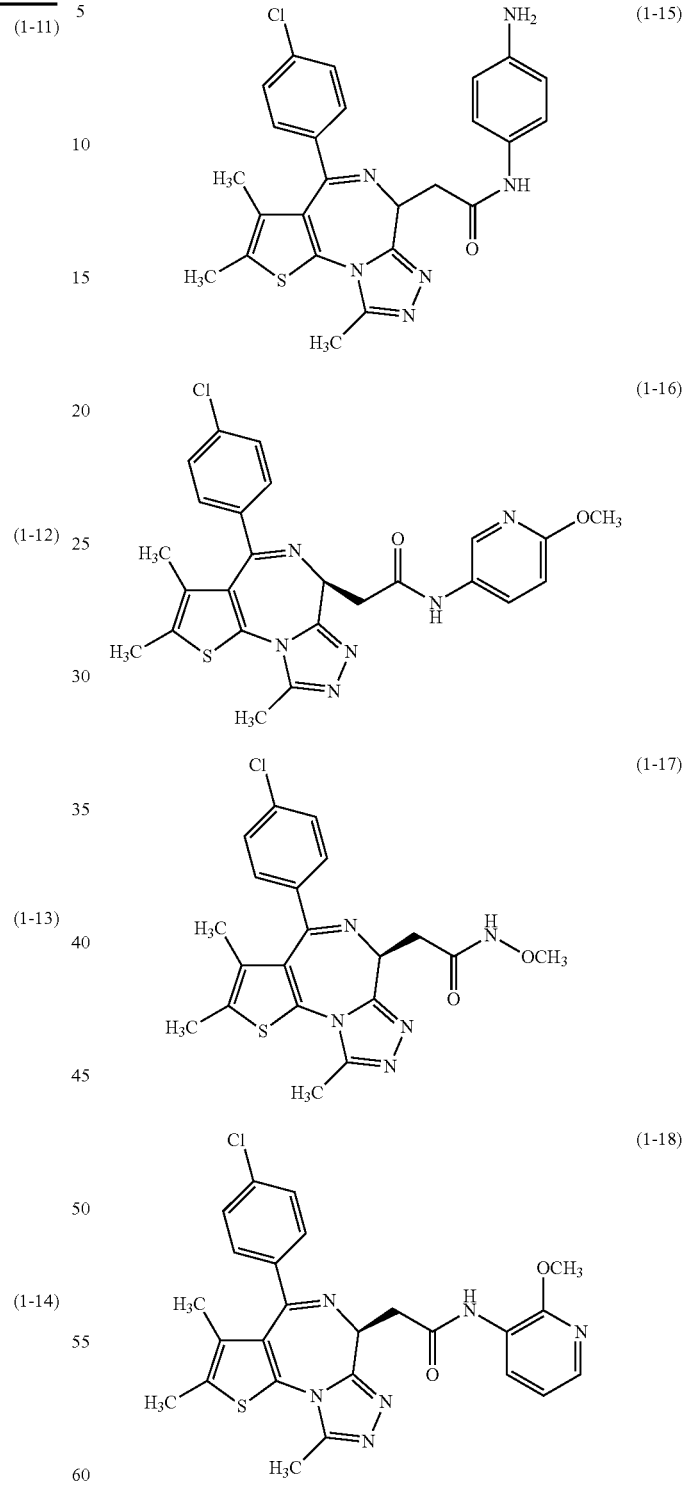
(1-15)
(1-16)
(1-17)
(1-18)
In some embodiments, thienotriazolodiazepine compounds of Formula (1) include (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]triazolo[4,3-a][1, 4]diazepin-6-yl}acetate, (iii) methyl (S){2,3,9-trimethyl-4-(4-phenylaminophenyl)-6H-thieno[3,2-f][1,2,4]triazolo[4,3-a][1,4]diazepin-6-yl}acetate; and (iv) methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate.

In some embodiments, thienotriazolodiazepine compounds of Formula (1) include (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide.

In some embodiments, thienotriazolodiazepine compounds of Formula (1) include (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide dihydrate.

IV. Formulations

The compound of Formula (1) presents highly specific difficulties in relation to administration generally and the preparation of galenic compositions in particular, including the particular problems of drug bioavailability and variability in inter- and intra-patient dose response, necessitating development of a non-conventional dosage form with respect to the practically water-insoluble properties of the compound.

Previously, it had been found that the compound of Formula (1) could be formulated as a solid dispersion with the carrier ethyl acrylate-methyl methacrylate-trimethylammonioethyl methacrylate chloride copolymer (Eudragit RS, manufactured by Rohm) to provide an oral formulation that preferentially released the pharmaceutical ingredient in the lower intestine for treatment of inflammatory bowel diseases such as ulcerative colitis and Crohn's disease (US Patent Application 20090012064 A1, published Jan. 8, 2009). It was found, through various experiments, including animal tests, that in inflammatory bowel diseases drug release in a lesion and a direct action thereof on the inflammatory lesion were more important than the absorption of the drug into circulation from the gastrointestinal tract.

It has now been unexpectedly found that thienotriazolodiazepine compounds, according to Formula (1), pharmaceutically acceptable salts, solvates, including hydrates, racemates, enantiomers isomers, and isotopically-labeled forms thereof, can be formulated as a solid dispersion with pharmaceutically acceptable polymers to provide an oral formulation that provides high absorption of the pharmaceutical ingredient into the circulation from the gastrointestinal tract for treatment of diseases other than inflammatory bowel diseases. Studies in both dogs and humans have confirmed high oral bioavailability of these solid dispersions compared with the Eudragit solid dispersion formulation previously developed for the treatment of inflammatory bowel disease.

Solid dispersions are a strategy to improve the oral bioavailability of poorly water soluble drugs.

The term "solid dispersion" as used herein refers to a group of solid products including at least two different components, generally a hydrophilic carrier and a hydrophobic drug, the thienotriazolodiazepine compounds, according to Formula (1). Based on the drug's molecular arrangement within the dispersion, six different types of solid dispersions can be distinguished. Commonly, solid dispersions are classified as simple eutectic mixtures, solid solutions, glass solution and suspension, and amorphous precipitations in a crystalline carrier. Moreover, certain combinations can be encountered, for example, in the same sample some molecules may be present in clusters while some are molecularly dispersed.

In one embodiment, the thienotriazolodiazepine compounds, according to Formula (1) can be dispersed molecularly, in amorphous particles (clusters). In another embodiment, the thienotriazolodiazepine compounds, according to Formula (1) can be dispersed as crystalline particles. In one embodiment, the carrier can be crystalline. In another embodiment, the carrier can be amorphous.

In one embodiment, the present invention provides a pharmaceutical composition comprising a solid dispersion of a thienotriazolodiazepine compound, in accordance with Formula (1), or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is hypromellose acetate succinate (also called hydroxypropylmethylcellulose acetate succinate or HPMCAS). In one embodiment, the dispersion has a thienotriazolodiazepine compound to hydroxypropylmethylcellulose acetate succinate (HPMCAS) weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, the present invention provides a pharmaceutical composition comprising a solid dispersion of a thienotriazolodiazepine compound of Formula (1) or a pharmaceutically acceptable salt, a solvate, including a hydrate, a racemate, an enantiomer, an isomer, or an isotopically-labeled form thereof in a pharmaceutically acceptable polymer. In one embodiment, the pharmaceutically acceptable polymer is polyvinylpyrrolidone (also called povidone or PVP). In one embodiment, the dispersion has a thienotriazolodiazepine compound to PVP weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to about 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to about 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1.

In one embodiment, a pharmaceutical composition of the present invention comprises a solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1.

In some embodiments, a pharmaceutical composition comprising a solid dispersion is prepared by spray drying.

In one embodiment, a pharmaceutical composition of the present invention comprises a spray dried solid dispersion of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of compound (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of compound (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In some such embodiments, the solid dispersion was exposed to a relative humidity of 75% at 40° C. for at least one month. In other such embodiments, the single Tg occurs at about 135° C. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1.

In one embodiment, a pharmaceutical composition of the present invention comprises a spray dried solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1.

In one preferred embodiment, the present invention provides a pharmaceutical composition comprising a solid dispersion of 2-[(6S)-4-(4-chlorophenyl)-2,3,9-trimethyl-6H-thienol[3,2-f]-[1,2,4]triazolo[4,3-a][1,4]diazepin-6-yl]-N-(4-hydroxyphenyl)acetamide dihydrate, compound (1-1):

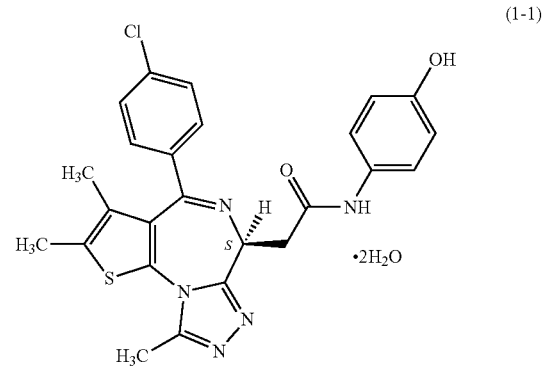

or a pharmaceutically acceptable salt, a solvate, including a hydrate, a racemate, an enantiomer, an isomer, or an isotopically-labeled form and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In another embodiment, the pharmaceutical composition comprises a solid dispersion compound (1-1) or a pharmaceutically acceptable salt, a solvate, including a hydrate, a racemate, an enantiomer, an isomer, or an isotopically-labeled form; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of an amorphous form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of an amorphous form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 175° C. to 185° C. In other such embodiments, the single Tg occurs at about 189° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of a crystalline form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, the solid dispersion is spray dried.

In one embodiment, a pharmaceutical composition of the present invention comprises a solid dispersion of a crystalline form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, the solid dispersion is spray dried.

The solid dispersions of the invention, described herein, exhibit especially advantageous properties when administered orally. Examples of advantageous properties of the solid dispersions include, but are not limited to, consistent and high level of bioavailability when administered in standard bioavailability trials in animals or humans. The solid dispersions of the invention can include a solid dispersion comprising thienotriazolodiazepine compound of Formula (1) and a polymer and additives. In some embodiments, the solid dispersions can achieve absorption of the thienotriazolodiazepine compound of Formula (1) into the bloodstream that cannot be obtained by merely admixing the thienotriazolodiazepine compound of Formula (1) with additives since the thienotriazolodiazepine compound of Formula (1) drug has negligible solubility in water and most aqueous media. The bioavailability, of thienotriazolodiazepine compound of Formula (1) or of thienotriazolodiazepine compound (1-1) may be measured using a variety of in vitro and/or in vivo studies. The in vivo studies may be performed, for example, using rats, dogs or humans.

The bioavailability may be measured by the area under the curve (AUC) value obtained by plotting a serum or plasma concentration, of the thienotriazolodiazepine compound of Formula (1) or thienotriazolodiazepine compound (1-1), along the ordinate (Y-axis) against time along the abscissa (X-axis). The AUC value of the thienotriazolodiazepine compound of Formula (1) or thienotriazolodiazepine compound (1-1) from the solid dispersion, is then compared to the AUC value of an equivalent concentration of crystalline thienotriazolodiazepine compound of Formula (1) or crystalline thienotriazolodiazepine compound (1-1) without polymer. In some embodiments, the solid dispersion provides an area under the curve (AUC) value, when administered orally to a dog, that is selected from: at least 0.4 times, 0.5 times, 0.6 times, 0.8 times, 1.0 times, a corresponding AUC value provided by a control composition administered intravenously to a dog, wherein the control composition comprises an equivalent quantity of a crystalline thienotriazolodiazepine compound of Formula (1).

The bioavailability may be measured by in vitro tests simulating the pH values of a gastric environment and an intestine environment. The measurements may be made by suspending a solid dispersion of the thienotriazolodiazepine compound of Formula (1) or thienotriazolodiazepine compound (1-1), in an aqueous in vitro test medium having a pH between 1.0 to 2.0, and the pH is then adjusted to a pH between 5.0 and 7.0, in a control in vitro test medium. The concentration of the amorphous thienotriazolodiazepine compound of Formula (1) or amorphous thienotriazolodiazepine compound (1-1) may be measured at any time during the first two hours following the pH adjustment. In some embodiments, the solid dispersion provides a concentration, of the amorphous thienotriazolodiazepine compound of Formula (1) or amorphous thienotriazolodiazepine compound (1-1), in an aqueous in vitro test medium at pH between 5.0 to 7.0 that is selected from: at least 5-fold greater, at least 6 fold greater, at least 7 fold greater, at least 8 fold greater, at least 9 fold greater or at least 10 fold greater, compared to a concentration of a crystalline thienotriazolodiazepine compound of Formula (1) or crystalline thienotriazolodiazepine compound (1-1), without polymer.

In other embodiments, the concentration of the amorphous thienotriazolodiazepine compound of Formula (1) or amorphous thienotriazolodiazepine compound (1-1), from the solid dispersion placed in an aqueous in vitro test medium having a pH of 1.0 to 2.0, is: at least 40%, at least 50%, at least 60%, at least 70%; at least 80%, higher than a concentration of a crystalline thienotriazolodiazepine compound of Formula (1) without polymer. In some such embodiments, the polymer of the solid dispersion is HPMCAS. In some such embodiments, the polymer of the solid dispersion is PVP.

In other embodiments, a concentration of the amorphous thienotriazolodiazepine compound of Formula (1) or amorphous thienotriazolodiazepine compound (1-1), from the solid dispersion, is: at least 40%, at least 50%, at least 60%, at least 70%; at least 80%, higher compared to a concentration of thienotriazolodiazepine compound of Formula (1), from a solid dispersion of thienotriazolodiazepine compound of the Formula (1) and a pharmaceutically acceptable polymer selected from the group consisting of: hypromellose phthalate and ethyl acrylate-methyl methacrylate-trimethylammonioethyl methacrylate chloride copolymer, wherein each solid dispersion was placed in an aqueous in vitro test medium having a pH of 1.0 to 2.0. In some such embodiments, the polymer of the solid dispersion is HPMCAS. In some such embodiments, the polymer of the solid dispersion is PVP.

In some embodiments, the solid dispersions, described herein, exhibit stability against recrystallization of the thienotriazolodiazepine compound of the Formula (1) or the thienotriazolodiazepine compound (1-1) when exposed to humidity and temperature over time. In one embodiment, the concentration of the amorphous thienotriazolodiazepine compound of the Formula (1) or the thienotriazolodiazepine compound (1-1) which remains amorphous is selected from: at least 90%, at least 91%, at least 92%, at least 93%, at least 94%, at least 95%, at least 96%, at least 97%, at least 98% and at least 99%.

V. Dosage Forms

Suitable dosage forms that can be used with the solid dispersions of the present invention include, but are not limited to, capsules, tablets, mini-tablets, beads, beadlets, pellets, granules, granulates, and powder. Suitable dosage forms may be coated, for example using an enteric coating. Suitable coatings may comprise but are not limited to cellulose acetate phthalate, hydroxypropylmethylcellulose (HPMC), hydroxypropylmethylcellulose phthalate, a polymethylacrylic acid copolymer, or hydroxypropylmethylcellulose acetate succinate (HPMCAS). In some embodiments, certain combinations can be encountered, for example, in the same sample some molecules of the thienotriazolodiazepine of the present invention may be present in clusters while some are molecularly dispersed with a carrier.

In some embodiments, the solid dispersions of the invention may be formulated as tablets, caplets, or capsules. In one some embodiments, the solid dispersions of the invention may be formulated as mini-tablets or pour-into-mouth granules, or oral powders for constitution. In some embodiments, the solid dispersions of the invention are dispersed in a suitable diluent in combination with other excipients (e.g., re-crystallization/precipitation inhibiting polymers, taste-masking components, etc.) to give a ready-to-use suspension formulation. In some embodiments, the solid dispersions of the invention may be formulated for pediatric treatment.

In one embodiment, the pharmaceutical composition of the present invention is formulated for oral administration. In one embodiment, the pharmaceutical composition comprises a solid dispersion, according to the various embodiments described herein, comprising a thienotriazolodiazepine compound of Formula (1) or a pharmaceutically acceptable salt, a solvate, including a hydrate, a racemate, an enantiomer, an isomer, or an isotopically-labeled form thereof; and a polymer carrier. In one embodiment, the pharmaceutical composition further includes one or more additives such as disintegrants, lubricants, glidants, binders, and fillers.

Examples of suitable pharmaceutically acceptable lubricants and pharmaceutically acceptable glidants for use with the pharmaceutical composition include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose, glyceryl behenate, stearic acid, hydrogenated castor oil, glyceryl monostearate, and sodium stearyl fumarate.

Examples of suitable pharmaceutically acceptable binders for use with the pharmaceutical composition include, but are not limited to starches; celluloses and derivatives thereof, e.g., microcrystalline cellulose (e.g., AVICEL PH from FMC), hydroxypropyl cellulose, hydroxyethyl cellulose, and hydroxypropylmethylcellulose (HPMC, e.g., METHOCEL from Dow Chemical); sucrose, dextrose, corn syrup; polysaccharides; and gelatin.

Examples of suitable pharmaceutically acceptable fillers and pharmaceutically acceptable diluents for use with the pharmaceutical composition include, but are not limited to, confectioner's sugar, compressible sugar, dextrates, dextrin, dextrose, lactose, mannitol, microcrystalline cellulose (MCC), powdered cellulose, sorbitol, sucrose, and talc.

In some embodiments, excipients may serve more than one function in the pharmaceutical composition. For example, fillers or binders may also be disintegrants, glidants, anti-adherents, lubricants, sweeteners and the like.

In some embodiments, the pharmaceutical compositions of the present invention may further include additives or ingredients, such as antioxidants (e.g., ascorbyl palmitate, butylated hydroxylanisole (BHA), butylated hydroxytoluene (BHT), α-tocopherols, propyl gallate, and fumaric acid), antimicrobial agents, enzyme inhibitors, stabilizers (e.g., malonic acid), and/or preserving agents.

Generally, the pharmaceutical compositions of the present invention may be formulated into any suitable solid dosage form. In some embodiments, the solid dispersions of the invention are compounded in unit dosage form, e.g., as a capsule, or tablet, or a multi-particulate system such as granules or granulates or a powder, for administration.

In one embodiment, a pharmaceutical compositions includes a solid dispersion of a thienotriazolodiazepine compound of Formula (1), according to the various embodiments of solid dispersions described herein, and hydroxypropylmethylcellulose acetate succinate (HPMCAS), wherein the thienotriazolodiazepine compound is amorphous in the solid dispersion and has a thienotriazolodiazepine compound to hydroxypropylmethylcellulose acetate succinate (HPMCAS), weight ratio of 1:3 to 1:1; 45-50 wt. % of lactose monohydrate; 35-40 wt. % of microcrystalline cellulose; 4-6 wt. % of croscarmellose sodium; 0.8-1.5 wt. % of colloidal silicon dioxide; and 0.8-1.5 wt. % of magnesium stearate.

VI. Dosage

In one embodiment, the present invention provides a pharmaceutical composition that maybe formulated into any suitable solid dosage form. In one embodiment, a pharmaceutical composition in accordance with the present invention comprises one or more of the various embodiments of the thienotriazolodiazepine of Formula (1) as described herein in a dosage amount ranging from about 10 mg to about 100 mg. In one embodiment, the pharmaceutical composition of the present invention includes one or more of the various embodiments of the thienotriazolodiazepine of Formula (1) as described herein in a dosage amount selected from the group consisting of from about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, and about 10 mg to about 20 mg. In one embodiment, the pharmaceutical composition of the present invention includes one or more of the various embodiments of the thienotriazolodiazepine of Formula (1) as described herein in a dosage amount selected from the group consisting of about 10 mg, about 50 mg, about 75 mg, about 100 mg.

In one embodiment, the pharmaceutical composition of the present invention includes administering to a subject in need thereof one or more of the various embodiments of the thienotriazolodiazepine of Formula (I) as described herein in a dosage amount selected from the group consisting of about 1 mg, about 2 mg, about 2.5 mg, about 3 mg, about 4 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, and about 150 mg, and in a dosage form selected from the group consisting of once weekly, once daily every sixth day, once daily every fifth day, once daily every fourth day, once daily every third day, once daily every other day, once daily, twice daily, three times daily, four times daily, and five times daily. In another embodiment, any of the foregoing dosage amounts or dosage forms is decreased periodically or increased periodically. In one embodiment, the pharmaceutical composition of the present invention includes administering to a subject in need thereof a thienotriazolodiazepine selected from the group consisting of compounds (1-1), (1-2), (1-3), (1-4), (1-5), (1-6), (1-7), (1-8), (1-9), (1-10), (1-11), (1-12), (1-13), (1-14), (1-15), (1-16), (1-17), and (1-18), in a dosage amount selected from the group consisting of about 1 mg, about 2 mg, about 2.5 mg, about 3 mg, about 4 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, and about 150 mg, and in a dosage form selected from the group consisting of once weekly, once daily every sixth day, once daily every fifth day, once daily every fourth day, once daily every third day, once daily every other day, once daily, twice daily, three times daily, four times daily, and five times daily. In another embodiment, any of the foregoing dosage amounts or dosage forms is decreased periodically or increased periodically.

Such unit dosage forms are suitable for administration 1 to 5 times daily depending on the particular purpose of therapy, the phase of therapy, and the like. In one embodiment, the dosage form may be administered to a subject in need thereof at least once daily for at least two successive days. In one embodiment, the dosage form may be administered to a subject in need thereof at least once daily on alternative days. In one embodiment, the dosage form may be administered to a subject in need thereof at least weekly and divided into equal and/or unequal doses. In one embodiment, the dosage form may be administered to a subject in need thereof weekly, given either on three alternate days and/or 6 times per week. In one embodiment, the dosage form may be administered to a subject in need thereof in divided doses on alternate days, every third day, every fourth day, every fifth day, every sixth day and/or weekly. In one embodiment, the dosage form may be administered to a subject in need thereof two or more equally or unequally divided doses per month.

The dosage form used, e.g., in a capsule, tablet, mini-tablet, beads, beadlets, pellets, granules, granulates, or powder may be coated, for example using an enteric coating. Suitable coatings may comprise but are not limited to cellulose acetate phthalate, hydroxypropylmethylcellulose (HPMC), hydroxypropylmethylcellulose phthalate, a polymethylacrylic acid copolymer, or hydroxypropylmethylcellulose acetate succinate (HPMCAS).

VII. Process

The thienotriazolodiazepine compounds disclosed herein can exist as free base or as acid addition salt. They can be obtained according to the procedures described in US Patent Application Publication No. 2010/0286127, incorporated by reference in its entirety herein, or in the present application. Individual enantiomers and diastereomers of the thienotriazolodiazepine compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent.

If desired, a particular enantiomer of the thienotriazolodiazepine compounds disclosed herein may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers, thus formed by fractional crystallization or chromatographic means well known in the art, and subsequent recovery of the pure enantiomers. Various methods well known in the art may be used to prepare the thienotriazolodiazepine compounds of Formula (1) with an enantiomeric excess of generally more than about 80%. Advantageously, preferred enantiomeric excess is of more than 80%, preferably of more than 90%, more preferably of more than 95%, and most preferably of 99% and more.

The solid dispersions of the present invention can be prepared by a number of methods, including by melting and solvent evaporation. The solid dispersions of the present invention can also be prepared according to the procedures described in: Chiou W L, Riegelman S: "Pharmaceutical applications of solid dispersion systems", *J Pharm. Sci.* 1971; 60:1281-1302; Serajuddin ATM: "Solid dispersion of poorly water-soluble drugs: early promises, subsequent problems, and recent breakthroughs", *J. Pharm. Sci.* 1999; 88:1058-1066; Leuner C, Dressman J: "Improving drug solubility for oral delivery using solid dispersions", *Eur. J. Pharm. Biopharm.* 2000; 50:47-60; and Vasconcelos T, Sarmento B, Costa P: "Solid dispersions as strategy to improve oral bioavailability of poor water soluble drugs", *Drug Discovery Today* 2007; 12:1068-1075, all of which are incorporated herein by reference in their entireties.

In one embodiment, solid dispersions of the present invention are prepared by a melting process. In one embodiment, the melting process comprises melting one or more of the various embodiments of the thienotriazolodiazepine of Formula (1) within a carrier. In one embodiment, the melting process includes cooling a melted compound of the present invention and a carrier. In one embodiment, the melting process comprises pulverization of the melted compound and the carrier. In one embodiment, a melted compound of the present invention and a carrier are pulverized following the cooling step.

In some embodiments in which the thienotriazolodiazepine of Formula (1) or a pharmaceutically acceptable salt, a solvate, including a hydrate, a racemate, an enantiomer, an isomer, or an isotopically-labeled form thereof and the carrier are incompatible, a surfactant may be added during the melting step to prevent formation of two liquid phases or a suspension in the heated mixture. In some embodiments, one or more of the various embodiments of the thienotriazolodiazepine of Formula (1) is suspended in a previously melted carrier, instead of using both drug and carrier in the melted state, thereby reducing the process temperature. In one embodiment, melted drug and carrier mixture is cooled an ice bath agitation. In one embodiment, melted drug and carrier mixture is cooled and solidified by spray cooling (alternatively spray congealing).

In one embodiment, melted drug and carrier mixture is cooled and solidified by forming the melt into particles by spraying the melt into a cooling chamber through which ambient or cooled, low temperature air is passing. In one embodiment, melted drug and carrier mixture is cooled and solidified by atomization and re-solidification of the molten dispersion in a suitable fluid bed processor. In one embodiment, melted drug and carrier mixture is cooled and solidified by melt-granulation in a heatable high-shear mixer.

In some embodiments, hot-stage extrusion or melt agglomeration may be used to avoid melting limitations of the drug. Hot-stage extrusion consists of the extrusion, at high rotational speed, of the drug and carrier, previously mixed, at melting temperature for a short period of time; the resulting product is collected after cooling at room temperature and milled.

In one embodiment, one or more of the various embodiments of the thienotriazolodiazepine of Formula (1) is processed at a reduced processing temperature to avoid degradation of any thermally labile compound. In one embodiment, the reduced processing temperature is achieved by associating a hot-stage extrusion with a temporary plasticizer such as carbon dioxide. In one embodiment, melt agglomeration is used in the preparation of solid dispersions in accordance with the present invention in conventional high shear mixers or in a rotary processors. In one embodiment, the solid dispersion in accordance with the present invention is prepared by adding a molten carrier containing a thienotriazolodiazepine compound in accordance with the present invention to a heated excipient. In one embodiment, the solid dispersion in accordance with the present invention is prepared by adding by adding a molten carrier to a heated mixture of the thienotriazolodiazepine in accordance with the present invention and one or more excipients. In one embodiment, the solid dispersion in accordance with the present invention is prepared by heating a mixture of a thienotriazolodiazepine compound in accordance with the present invention, a carrier and one or more excipients to a temperature within or above the melting range of the carrier.

In some embodiments, a one or more of the various embodiments for the formulation of the thienotriazolodiazepine, according to Formula (1), is prepared by a solvent evaporation method. In one embodiment, the solvent evaporation method comprises solubilization of a thienotriazolodiazepine compound, according to Formula (1), and carrier in a volatile solvent that is subsequently evaporated. In one embodiment, the volatile solvent may one or more excipients. In one embodiment, the one or more excipients include, but are not limited to anti-sticking agents, inert fillers, surfactants wetting agents, pH modifiers and additives. In one embodiment, the excipients may dissolved or in suspended or swollen state in the volatile solvent.

In one embodiment, preparation of solid dispersions in accordance with the present invention includes drying one or more excipients suspended in a volatile solvent. In one embodiment, the drying includes vacuum drying, slow evaporation of the volatile solvent at low temperature, use of a rotary evaporator, spray-drying, spray granulation, freeze-drying, or use of supercritical fluids.

In one embodiment, spray drying preparation of a formulation for the thienotriazolodiazepine composition, according to Formula (1), is used which involves atomization of a suspension or a solution of the composition into small droplets, followed by rapid removal solvent from the formulation. In one embodiment, preparation of a formulation in accordance with the present invention involves spray granulation in which a solution or a suspension of the composition in a solvent is sprayed onto a suitable chemically and/or physically inert filler, such as lactose or mannitol. In one embodiment, spray granulation of the solution or the suspension of the composition is achieved via two-way or three-way nozzles.

In some embodiments, preparation of solid dispersions in accordance with the present invention includes use of supercritical fluids. The term "supercritical fluids" refers to substances existing as a single fluid phase above their critical temperature and critical pressure. In one embodiment, preparation of a formulation, in accordance with the present invention, includes use a supercritical carbon dioxide fluid. In one embodiment, preparation of a formulation, in accordance with the present invention, using the supercritical fluid technique comprises dissolving a thienotriazolodiazepine compound, according to Formula (1), and carrier in a common solvent that is introduced into a particle formation vessel through a nozzle, simultaneously with carbon dioxide; and spraying the solution to allow the solvent be rapidly extracted by the supercritical fluid, thereby resulting in the precipitation of solid dispersion particles on the walls of the vessel.

In some embodiments, preparation of solid dispersions in accordance with the present invention includes use of a co-precipitation method. In one embodiment, a non-solvent is added dropwise to a thienotriazolodiazepine composition, according to Formula (1), and a carrier solution, under constant stirring. In one embodiment, the thienotriazolodiazepine composition, according to Formula (1), and the carrier are co-precipitated to form microparticles during the addition of the non-solvent. In one embodiment, the resulting microparticles are filtered and dried to provide the desired solid dispersion.

The proportion of compound of Formula (1) and polymeric carrier(s) to be mixed is not particularly limited, as long as it can improve the bioavailability of the compound of Formula (1) and varies depending on the kind of polymer.

The invention is illustrated in the following non-limiting examples.

VIII. Examples

Example 1: In Vitro Screening of Solid Dispersions of Compound (1-1)

Ten solid dispersions were prepared using compound (1-1) and one of five polymers, including hypromellose acetate succinate (HPMCAS-M), hypromellose phthalate (HPMCP-HP55), polyvinylpyrrolidone (PVP), PVP-vinyl acetate (PVP-VA), and Eudragit L100-55, at both 25% and 50% of compound (1-1) loading, for each polymer. Solid dispersions were prepared by a solvent evaporation method, using spray-drying followed by secondary drying in a low-temperature convection oven. The performance of each solid dispersion was assessed via a non-sink dissolution performance test which measured both the total amount of drug and the amount of free drug present in solution over time. Non-sink dissolution was chosen because it best represents the in vivo situation for low soluble compounds. This test included a "gastric transfer" of dispersion from gastric pH (0.1N NaCl, pH 1.0) to intestinal pH (FaFSSIF, pH 6.5) approximately 30 to 40 minutes after the introduction of dispersion to the test medium, simulating in vivo conditions. [FaFSSIF is Fasted State Simulated Intestinal Fluid, comprised of 3 mM sodium taurocholate, 0.75 mM lecithin, 0.174 g NaOH pellets, 1.977 g $NaH_2PO_4.H_2O$, 3.093 g NaCl, and purified water qs 500 mL.] The amount of dissolved drug was quantified using a high-performance liquid chromatography (HPLC) method and an Agilent 1100 series HPLC. The dissolution profiles of the formulations (FIGS. 1A-1J) showed large increases in drug solubility in all dispersion candidates relative to the unformulated compound in the same media. Of the solid dispersions, the 25% compound (1-1) in PVP, 25% compound (1-1) in HPMCAS-M, and 50% compound (1-1) in HPMCAS-M dispersions provided enhanced oral absorption as compared to the unformulated compound, based on finding higher levels of free drug released at intestinal pH.

Example 2: In Vivo Screening of Solid Dispersions of Compound

The solid dispersions of compound (1-1), namely the 25% compound (1-1) in PVP, 25% compound (1-1) in HPMCAS-MG, and 50% compound (1-1) in HPMCAS-M dispersions, were prepared at larger scale for in vivo studies. Each formulation was assessed in the in vitro dissolution test described in Example 1. To ensure that these dispersions were both amorphous and homogeneous, each dispersion was assessed by powder x-ray diffraction (PXRD) and modulated differential scanning calorimetry (mDSC). The x-ray diffractometer was a Bruker D-2 Phaser. Additionally, to understand the effect of water on the glass transition temperature (Tg) for each dispersion, mDSC was performed on samples first equilibrated at a set relative humidity (i.e., 25%, 50%, and 75% RH) for at least 18 hours. Water can act as a plasticizer for solid dispersions and the hygroscopicity of the system due to the active compound or polymer can affect the amount of water uptake by these systems.

Figure 2A:
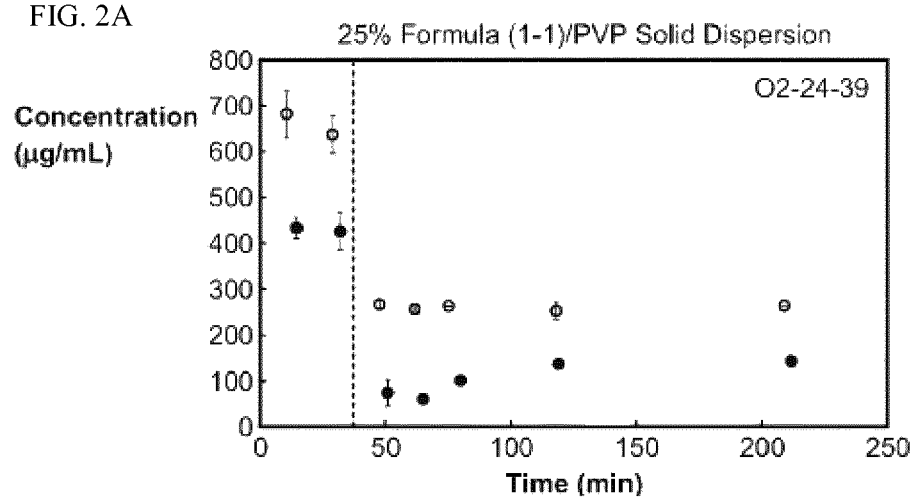
FIG. 2A illustrates results of in vivo screening of an exemplary formulation comprising a solid dispersion of 25% compound (1-1) and PVP.
Figure 2B:
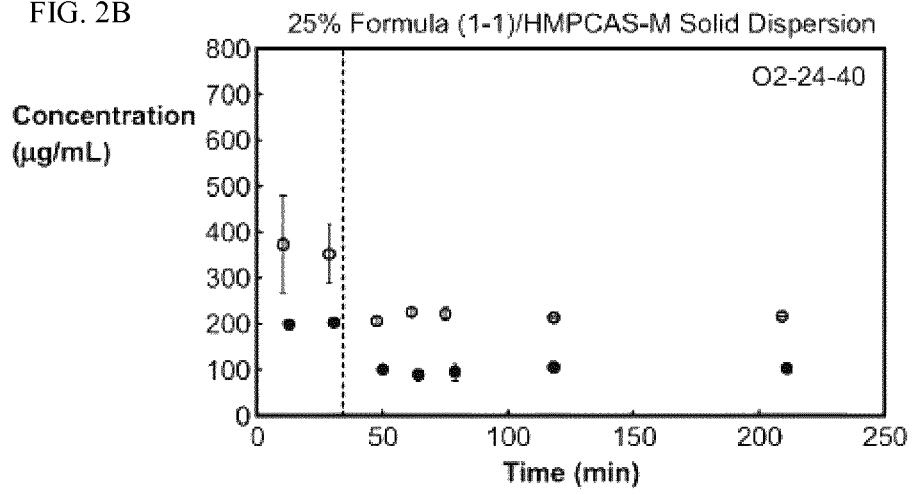
FIG. 2B illustrates results of an in vivo screening of an exemplary formulation comprising a solid dispersion of 25% compound (1-1) and HMPCAS-M.
Figure 2C:
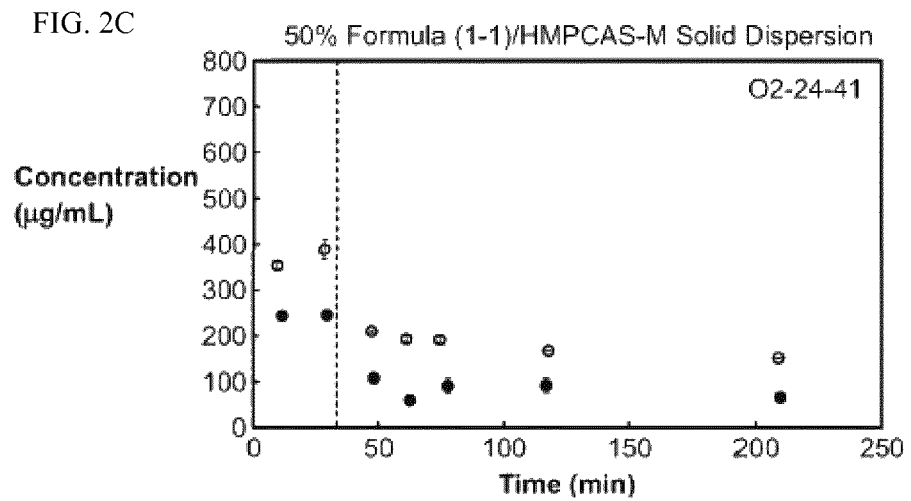
FIG. 2C illustrates results of an in vivo screening of an exemplary formulation comprising a solid dispersion of 50% compound (1-1) and HMPCAS-M.
Figure 3:
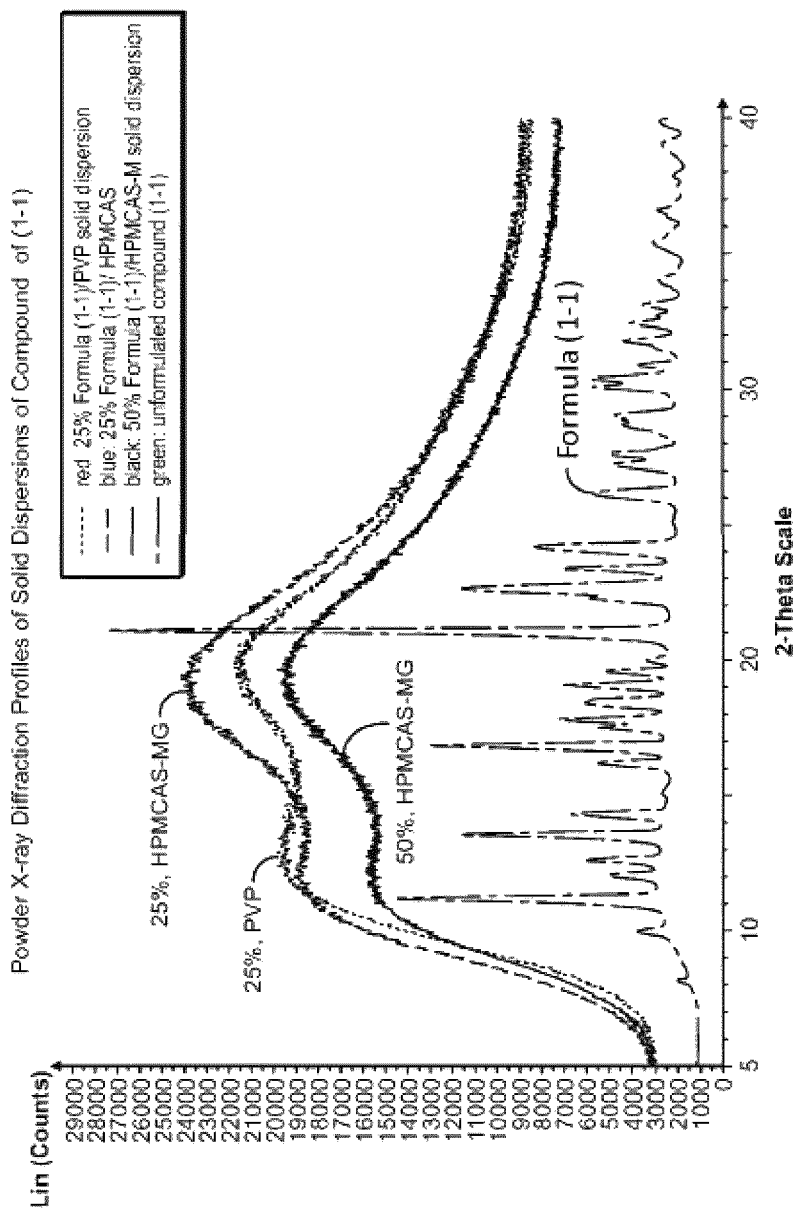
FIG. 3 illustrates powder X-ray diffraction profiles of solid dispersions of compound (1-1)
Figure 4A:
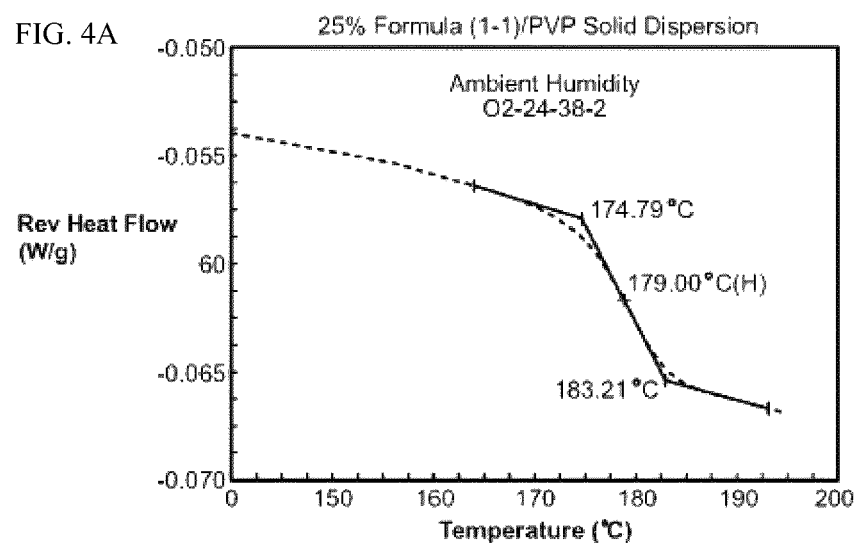
FIG. 4A illustrates modified differential scanning calorimetry trace for a solid dispersion of 25% compound (1-1) and PVP equilibrated under ambient conditions.
Figure 4B:
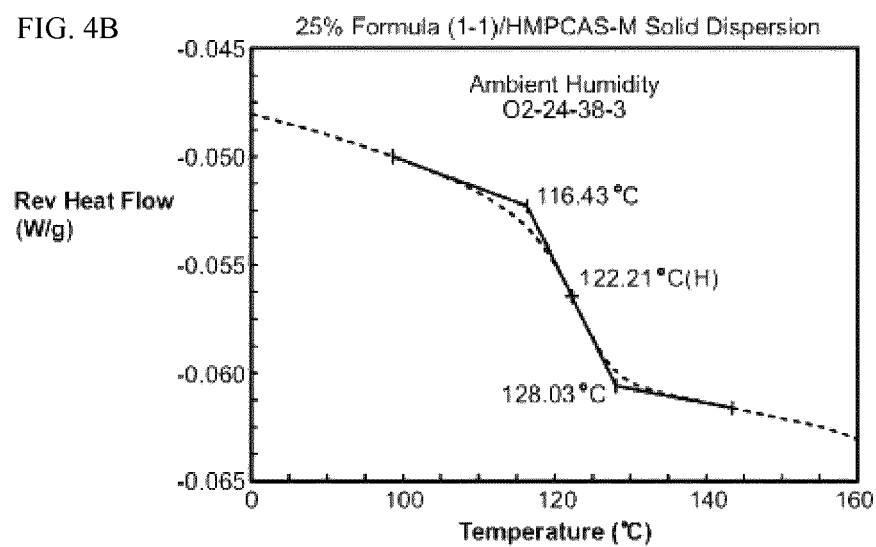
FIG. 4B illustrates modified differential scanning calorimetry trace for a solid dispersion of 25% compound (1-1) and HMPCAS-M equilibrated under ambient conditions.
Figure 4C:
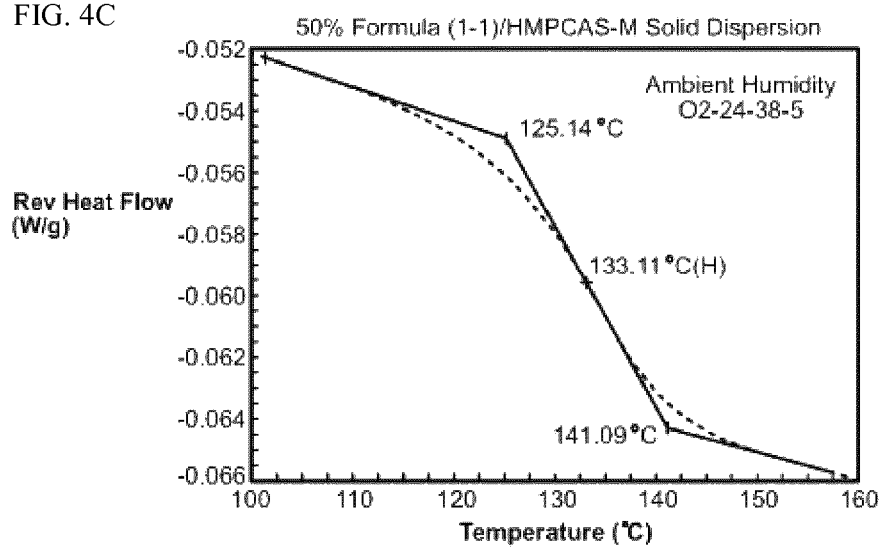
FIG. 4C illustrates modified differential scanning calorimetry trace for a solid dispersion of 50% compound (1-1) and HMPCAS-M equilibrated under ambient conditions.
Figure 5:
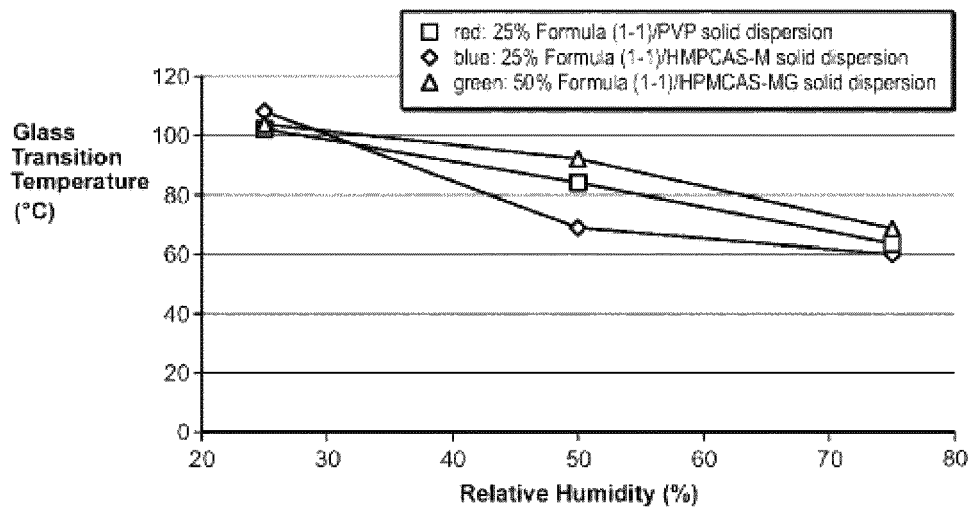
FIG. 5 illustrates plot of glass transition temperature (Tg) versus relative humidity (RH) for solid dispersions of 25% compound (1-1) and PVP or HMPCAS-M and 50% compound (1-1) and HPMCAS-MG.
Figure 6:
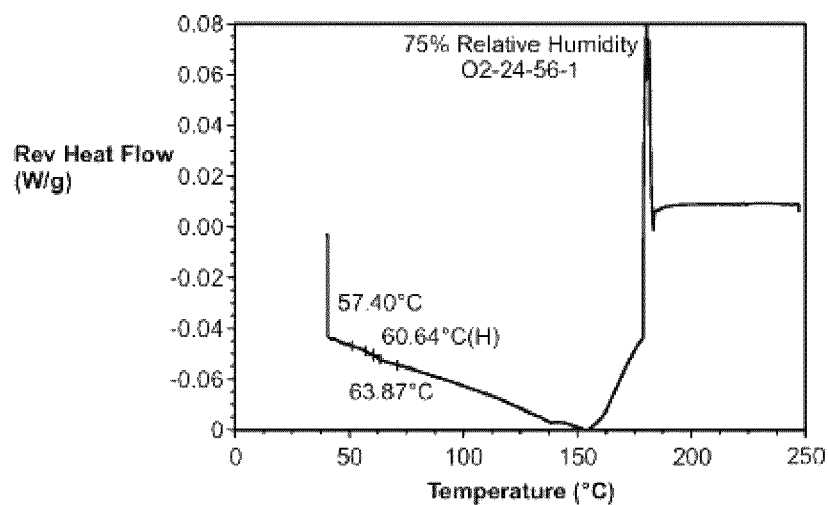
FIG. 6 illustrates modified differential scanning calorimetry trace for a solid dispersion of 25% compound (1-1) and PVP equilibrated under 75% relative humidity.

The non-sink dissolution results (FIGS. 2A-2C) were comparable to those found for the dispersions in Example 1. PXRD results (FIG. 3) showed no evidence of crystalline compound in any of the dispersions and mDSC results (FIGS. 4A-4C) showed a single glass transition temperature (Tg) for each dispersion, indicating that each dispersion was homogeneous. An inverse relationship between Tg and relative humidity was observed for each (FIG. 5). Notably, for the 25% compound (1-1) in PVP solid dispersion equilibrated at 75% RH, there appeared to be two Tgs, indicating that phase separation was occurring, and this dispersion also showed a melt event at 75% RH, suggesting that crystallization occurred during the RH equilibration (FIG. 6). This finding suggests that the 25% compound (1-1) in PVP dispersion may be less stable than the HPMCAS-M dispersions.

To assess the bioavailability of the three dispersions, groups of male beagle dogs (three per group) were given a 3 mg/kg dose of an aqueous suspension of solid dispersion of compound (1-1) administered by oral gavage or a 1 mg/kg dose of compound (1-1) dissolved in water:ethanol:polyethylene glycol (PEG) 400 (60:20:20) and administered as an intravenous bolus into the cephalic vein. Blood samples were collected from the jugular vein of each animal at 0 (pre-dose), 5, 15, and 30 minutes and 1, 2, 4, 8, 12, and 24 hours following intravenous administration and at 0 (pre-dose), 15 and 30 minutes and 1, 2, 4, 8, 12, and 24 hours following oral gavage administration. The amount of compound (1-1) present in each sample was detected using a qualified LC-MS/MS method with a lower limit of quantification of 0.5 ng/mL. The area under the plasma concentration-time curve (AUC) was determined by use of the linear trapezoidal rule up to the last measurable concentration without extrapolation of the terminal elimination phase to infinity. The elimination half-life ($t_{1/2}$) was calculated by least-squares regression analysis of the terminal linear part of the log concentration-time curve. The maximum plasma concentration ($C_{max}$) and the time to $C_{max}$ ($t_{max}$) were derived directly from the plasma concentration data. The oral bioavailability (F) was calculated by dividing the dose normalized AUC after oral administration by the dose normalized AUC after intravenous administration and reported as percentages (%). Results, summarized in Table 1 below, gave mean oral bioavailabilities of the 25% compound (1-1) in PVP, 25% compound (1-1) in HPMCAS-M, and 50% compound (1-1) in HPMCAS-M solid dispersions of 58%, 49%, and 74%, respectively.

Example 3: Preparation and Clinical Use of Capsules Containing a Solid Dispersion of Compound (1-1)

A gelatin capsule of 10 mg strength was prepared for initial clinical studies in patients with hematologic malignancies. Based on results of in vitro and in vivo testing of solid dispersions of compound (1-1), as described in Examples 1 and 2, a 50% compound (1-1) in HPMCAS-M solid dispersion was selected for capsule development. Capsule development was initiated targeting a fill weight of 190 mg in a size 3 hard gelatin capsule, as this configuration would potentially allow increasing the capsule strength by filling a larger size capsule while maintaining the pharmaceutical composition. Based on experience, four capsule formulations were designed with different amounts of disintegrant and with and without wetting agent. Since all four formulations showed similar disintegration test and dissolution test results, the simplest formulation (without wetting agent and minimum disintegrant) was selected for manufacturing. Manufacturing process development and scale-up studies were performed to confirm the spray drying process and post-drying times for the solid dispersion; blending parameters; roller compaction and milling of the blend to achieve target bulk density of approximately 0.60 g/cc; and capsule filling conditions.

Crystalline compound (1-1) and the polymer hypromellose acetate succinate (HPMCAS-M) were dissolved in acetone and spray-dried to produce solid dispersion intermediate (SDI) granules containing a 50% compound (1-1) loading. The SDI was shown by PXRD analysis to be amorphous and by mDSC analysis to be homogeneous (i.e., single Tg under ambient conditions). The 50% compound (1-1) in HPMCAS-M solid dispersion (1000 g) and excipients, including microcrystalline cellulose filler-binder (4428 g), croscarmellose sodium disintegrant (636 g), colloidal silicon dioxide dispersant/lubricant 156 g), magnesium stearate dispersant/lubricant (156 g), and lactose monohydrate filler (5364 g) were blended in stages in a V-blender. The blend was them compacted and granulated to obtain a

TABLE 1

Pharmacokinetic parameters of compound (1-1) after oral (po) and intravenous (iv) administrations to dogs (the values are averages from three dogs)

| Compound (1-1) formulation | Dose & Route | $C_{max}$ (ng/L) | $t_{max}$ (hr) | AUC (ng · min/mL) | $t_{1/2}$ (hr) | F (%) |
|---|---|---|---|---|---|---|
| Solution in water:ethanol:PEG400 (60:20:20) | 1 mg/kg IV | 769 | 0.083 | 53,312 | 1.5 | — |
| Aqueous suspension of 25% compound (1-1)/PVP solid dispersion | 3 mg/kg PO | 487 | 1.0 | 93,271 | 1.6 | 58 |
| Aqueous suspension of 25% compound (1-1)/HPMCAS-M solid dispersion | 3 mg/kg PO | 228 | 0.5 | 78,595 | 2.0 | 49 |
| Aqueous suspension of 50% compound (1-1)/HPMCAS-M solid dispersion | 3 mg/kg PO | 371 | 1.0 | 118,174 | 1.5 | 74 |

AUC: under the plasma concentration-time curve;
$C_{max}$: maximum plasma concentration;
F: bioavailability;
HPMCAS: hypromellose acetate sodium;
IV: intravenous;
PEG: polyethylene glycol;
PO; per os, oral;
PVP: polyvinylpyrrolidone;
$t_{max}$: time of $C_{max}$;
$t_{1/2}$: plasma elimination half-life bulk density of approximately 0.6 g/mL. The blend was dispensed into size 3 hard gelatin capsules (target fill weight: 190 mg) using an automated filling machine and finished capsules were polished using a capsule polisher machine.

Pharmacokinetic assessments were performed following oral dosing of 10 mg capsules containing the 50% compound (1-1) in HPMCAS solid dispersion and results were compared with pharmacokinetic assessments performed following oral dosing of administration of 4×10 mg capsules containing the Eudragit solid dispersion of compound (1-1) to healthy volunteers A comparison of the two pharmaceutical compositions is provided in Tables 2A and 2B below. The Eudragit formulation previously was described in Example 5 in US Patent Application 2009/0012064 A1, published Jan. 8, 2009. That application noted that the Eudragit solid dispersion formulation was made by dissolving and/or dispersing the thienotriazolodiazepine of formula (A) and coating excipients, including ammonio methacrylate copolymer type B (Eudragit RS), methacrylic acid copolymer type C (Eudragit L100-55), talc, and magnesium aluminosilicate, in a mixture of water and ethanol. This heterogeneous mixture then was applied to microcrystalline cellulose spheres (Nonpareil 101, Freund) using a centrifugal fluidizing bed granulator to produce granules that were dispensed into size 2 hydroxypropyl methylcellulose capsules.

In both clinical studies, blood levels of compound (1-1) were determined using validated LC-MS/MS methods and pharmacokinetic analyses were performed based on plasma concentrations of compound (1-1) measured at various time points over 24 hours after capsule administration. Results, summarized in Table 3 below, showed that the HPMCAS-M solid dispersion formulation had over 3-fold higher bioavailability in humans than the Eudragit solid dispersion formulation based on AUCs (924*4/1140, adjusting for difference in doses administered). Additionally, based on the observed $T_{max}$, the HPMCAS formulation is more rapidly absorbed than the Eudragit formulation ($T_{max}$ of 1 h vs 4-6 h). The marked improvement in systemic exposure with the HPMCAS-M solid dispersion formulation is unexpected.

TABLE 2A

Solid dispersion capsules of compound (1-1) for clinical use pharmaceutical composition containing 50% HPMCAS solid dispersion of compound (1-1): 10 mg strength, size 3 hard gelatin capsule

| | | Capsule Content | |
|---|---|---|---|
| Ingredient | Function | mg | Wt % |
| Compound of formula (II) | active agent | 10.0* | 5.56 |
| Hypromellose acetate succinate (HPMCAS-M) | carrier for solid dispersion | 10.0 | 5.56 |
| Lactose monohydrate | filler | 85.0 | 47.22 |
| Microcrystalline cellulose | filler-binder | 70.0 | 38.89 |
| Croscarmellose sodium | disintegrant | 10.0 | 5.56 |
| Colloidal silicon dioxide | dispersant/lubricant | 2.5 | 1.39 |
| Magnesium stearate | dispersant/lubricant | | |
| Total | | 190.0 | 100.0 |

TABLE 2B

Pharmaceutical composition containing Eudragit L100-55 solid dispersion of compound (1-1): 10 mg strength, size 2 hard gelatin capsule

| | | Capsule Content | |
|---|---|---|---|
| Ingredient | Function | mg | Wt % |
| Compound (1-1) | active agent | 10.0* | 3.8 |
| Core: | | | |
| Microcrystalline cellulose spheres (Nonpareil 101, Freund, Inc) | vehicle | 100.0 | 38.5 |
| Compound/polymer layer: | | | |
| Ammonio methacrylate copolymer, type B (NF. PhEur) (Eudragit RS, Evonik) | coating agent | 10.8 | 4.2 |
| Methacrylic acid copolymer, type C (NF)/Methacrylic acid-ethyl acrylate copolymer (1:1) type A (PhEur) (Eudragit L100-55, Evonik) | coating agent | 25.2 | 9.7 |
| Talc | coating agent | 88.2 | 33.9 |
| Magnesium aluminometasilicate (Neuslin, Fuji Chemical) | coating agent | 20.0 | 7.7 |
| Triethyl citrate | plasticizer | 5.0 | 1.9 |
| Silicon dioxide | fluidizing agent | 0.8 | 0.3 |
| | | 260.0 | 100.0 |

*as anhydrate

TABLE 3

Pharmacokinetic parameters following oral administration of solid dispersions of compound (1-1) to humans

| Compound (1-1) formulation | # Patients | Dose and Route | $C_{max}$ (ng/mL) | $T_{max}$ (hr) | $AUC_{0-24\,h}$ (ng · h/mL) |
|---|---|---|---|---|---|
| Eudragit solid dispersion formulation | 7 | 40 mg PO | 83 | 4 to 6 | 1140 |
| 50% HMPCAS-M solid dispersion formulation | 7 | 10 mg PO | 286 | 1 | 925 |

$AUC_{0-24\,h}$: area under the compound (1-1) plasma concentration vs. time curve over 24 hours
$C_{max}$: maximum concentration in plasma
hr: hour
HPMCAS: hypromellose acetate succinate
mL: milliliter
ng: nanogram
PO: per os, oral
$T_{max}$: time of $C_{max}$ Example 4. Oral Exposure in the Rat The oral bioavailability of three formulations of solid dispersions of compound (1-1) was determined in rats. The three dispersions chosen were the 25% dispersion of compound (1-1) in PVP, the 25% dispersion of compound (1-1) in HPMCAS-MG, and the 50% dispersion of compound (1-1) in HPMCAS-MG. The animals used in the study were Specific Pathogen Free (SPF) Hsd:Sprague Dawley rats obtained from the Central Animal Laboratory at the University of Turku, Finland. The rats were originally purchased from Harlan, The Netherlands. The rats were female and were ten weeks of age, and 12 rats were used in the study. The animals were housed in polycarbonate Makrolon II cages (three animals per cage), the animal room temperature was 21+/−3° C., the animal room relative humidity was 55+/−15%, and the animal room lighting was artificial and was cycled for 12 hour light and dark periods (with the dark period between 18:00 and 06:00 hours). Aspen chips (Tapvei Oy, Estonia) were used for bedding, and bedding was changed at least once per week. Food and water was provided prior to dosing the animals but was removed during the first two hours after dosing.

The oral dosing solutions containing the 25% dispersion of compound (1-1) in PVP, the 25% dispersion of compound (1-1) in HPMCAS-MG, and the 50% dispersion of compound (1-1) in HPMCAS-MG were prepared by adding a pre-calculated amount of sterile water for injection to containers holding the dispersion using appropriate quantities to obtain a concentration of 0.75 mg/mL of compound (1-1). The oral dosing solutions were subjected to vortex mixing for 20 seconds prior to each dose. The dosing solution for intravenous administration contained 0.25 mg/mL of compound (1-1) and was prepared by dissolving 5 mg of compound (1-1) in a mixture containing 4 mL of polyethylene glycol with an average molecular weight of 400 Da (PEG400), 4 mL of ethanol (96% purity), and 12 mL of sterile water for injection. The dosing solution containing the 25% dispersion of compound (1-1) in PVP was used within 30 minutes after the addition of water. The dosing solutions containing the 25% dispersion of compound (1-1) in HPMCAS-MG and the 50% dispersion of compound (1-1) in HPMCAS-MG were used within 60 minutes of after the addition of water. A dosing volume of 4 mL/kg was used to give dose levels of compound (1-1) of 1 mg/kg for intravenous administration and 3 mg/kg for oral administration. The dosing scheme is given in Table 4.

TABLE 4

Dosing scheme for rat oral exposure study.

| Rat | Weight | Dose (mL) | Test Item | Route |
|---|---|---|---|---|
| 1 | 236.5 | 0.95 | Compound (1-1) | intravenous |
| 2 | 221 | 0.88 | Compound (1-1) | intravenous |
| 3 | 237.5 | 0.95 | Compound (1-1) | intravenous |
| 4 | 255.5 | 1.02 | 25% dispersion of compound (1-1) in PVP | oral |
| 5 | 224.2 | 0.90 | 25% dispersion of compound (1-1) in PVP | oral |
| 6 | 219.2 | 0.88 | 25% dispersion of compound (1-1) in PVP | oral |
| 7 | 251.6 | 1.01 | 25% dispersion of compound (1-1) in HPMCAS-MG | oral |
| 8 | 240.4 | 0.96 | 25% dispersion of compound (1-1) in HPMCAS-MG | oral |
| 9 | 238 | 0.95 | 25% dispersion of compound (1-1) in HPMCAS-MG | oral |
| 10 | 226.6 | 0.91 | 50% dispersion of compound (1-1) in HPMCAS-MG | oral |
| 11 | 228.4 | 0.91 | 50% dispersion of compound (1-1) in HPMCAS-MG | oral |
| 12 | 228.5 | 0.91 | 50% dispersion of compound (1-1) in HPMCAS-MG | oral |

Blood samples of approximately 50 μL were collected into Eppendorf tubes containing 5 μL of ethylenediaminetetraacetic acid (EDTA) solution at time points of 0.25, 0.5, 1, 2, 4, 8, 12, and 24 hours after dosing, with each sample collected within a window of 5 minutes from the prescribed time point. From each sample, 20 μL of plasma was obtained and stored at dry ice temperatures for analysis. Analysis of each sample for the concentration of compound (1-1) was performed using a validated liquid chromatography tandem mass spectrometry (LC-MS/MS) method with a lower limit of quantitation of 0.5 ng/mL.

Pharmacokinetic parameters were calculated with the Phoenix WinNonlin software package (version 6.2.1, Pharsight Corp., CA, USA) with standard noncompartmental methods. The elimination phase half-life ($t_{1/2}$) was calculated by least-squares regression analysis of the terminal linear part of the log concentration-time curve. The area under the plasma concentration-time curve (AUC) was determined by use of the linear trapezoidal rule up to the last measurable concentration and thereafter by extrapolation of the terminal elimination phase to infinity. The mean residence time (MRT), representing the average amount of time a compound remains in a compartment or system, was calculated by extrapolating the drug concentration profile to infinity. The maximum plasma concentration ($C_{max}$) and the time to $C_{max}$ ($t_{max}$) were derived directly from the plasma concentration data. The tentative oral bioavailability (F) was calculated by dividing the dose normalised AUC after oral administration by the dose normalised AUC after intravenous administration, i.e. F=(AUC(oral)/Dose(oral))/(AUC (intravenous)/Dose(intravenous))] and is reported as percentage (%).

Figure 7:
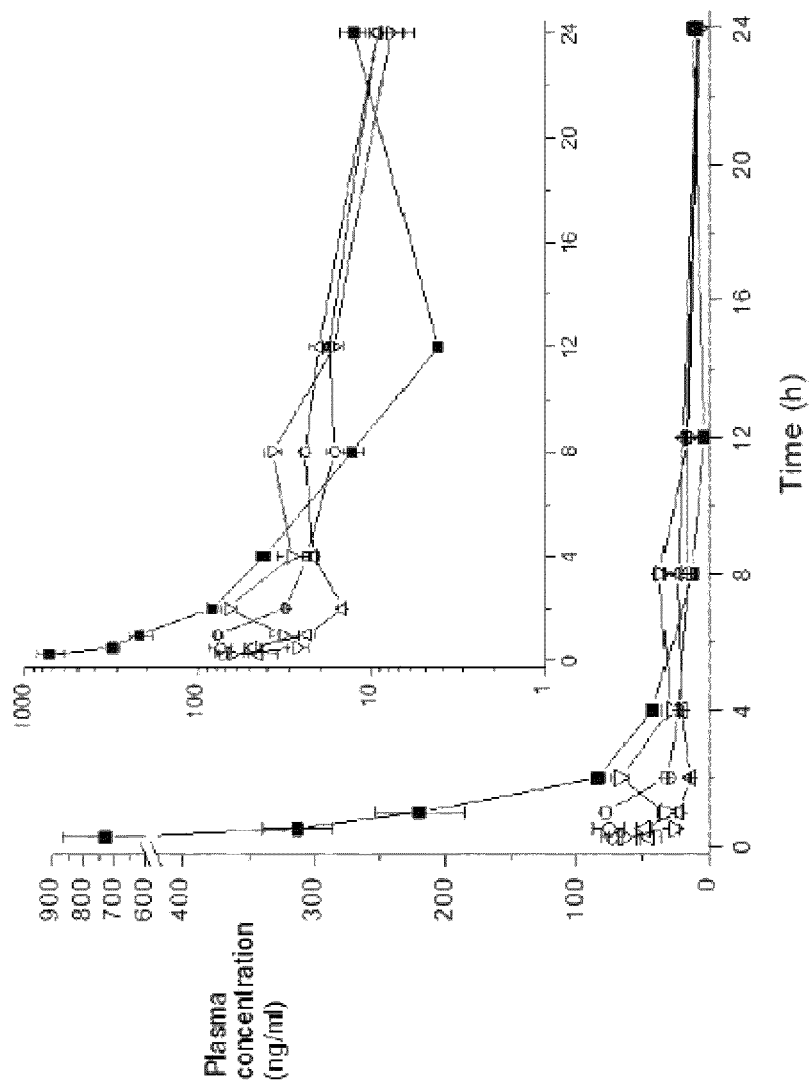
FIG. 7 illustrates plasma concentration versus time curves for Compound (1-1) after 1 mg/kg intravenous dosing (solid rectangles) and 3 mg/kg oral dosing as 25% Compound (1-1):PVP (open circles), 25% Compound (1-1):HPMCAS-MG (open triangles), and 50% Compound (1-1):HPMCAS-MG (open inverted triangles). The inset depicts the same data plotted on a semilogarithmic scale.
Figure 8:
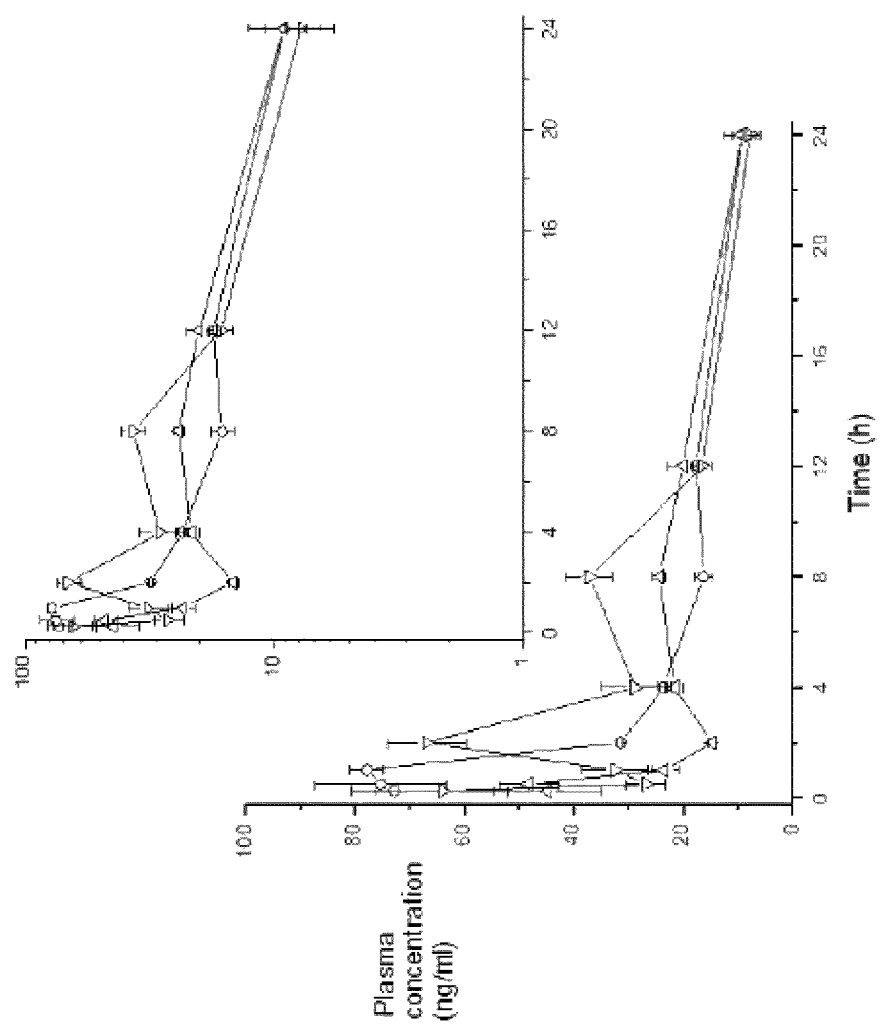
FIG. 8 illustrates plasma concentration versus time curves for Compound (1-1) after 3 mg/kg oral dosing as 25% Compound (1-1):PVP (open circles), 25% Compound (1-1):HPMCAS-MG (open triangles), and 50% Compound (1-1):HPMCAS-MG (open inverted triangles). The inset depicts the same data plotted on a semi-logarithmic scale.

The pharmacokinetic parameters are given in Table 5, and the plasma concentration versus time plots are shown in FIGS. 7 and 8.

TABLE 5

Pharmacokinetic parameters of compound (1-1) after oral and intravenous administrations. The values are an average from three animals.

| Compound | Parameter | 1 mg/kg intravenous | 3 mg/kg oral | F (%) |
|---|---|---|---|---|
| Compound (1-1) water:ethanol:PEG 400 (60:20:20) | AUC (min * ng/ml) | 74698 | | |
| | $C_{max}$ (ng/ml) | 730 | | |
| | $T_{max}$ (hr) | 0.25 | | |
| | $t_{1/2}$ (hr) 8.5 | 8.5 | | |
| | Cl/F (ml/min/kg) | 13.4 | | |
| | MRT (hr) | 7.4 | | |
| 25% dispersion of compound (1-1) in PVP | AUC (min * ng/ml) | | 39920 | 18 |
| | $C_{max}$ (ng/ml) | | 77.9 | |
| | $T_{max}$ (hr) | | 1 | |
| | $t_{1/2}$ (hr) 8.5 | | 13.8 | |
| | Cl/F (ml/min/kg) | | 75.2 | |
| | MRT (hr) | | 18.0 | |
| 25% dispersion of compound (1-1) in HPMCAS-MG | AUC (min * ng/ml) | | 35306 | 16 |
| | $C_{max}$ (ng/ml) | | 48.3 | |
| | $T_{max}$ (hr) | | 0.5 | |
| | $t_{1/2}$ (hr) 8.5 | | 11.0 | |
| | Cl/F (ml/min/kg) | | 85.0 | |
| | MRT (hr) | | 17.1 | |
| 50% dispersion of compound (1-1) in HPMCAS-MG | AUC (min * ng/ml) | | 40238 | 18 |
| | $C_{max}$ (ng/ml) | | 67.0 | |
| | $T_{max}$ (hr) | | 2 | |
| | $t_{1/2}$ (hr) 8.5 | | 9.5 | |
| | Cl/F (ml/min/kg) | | 74.6 | |
| | MRT (hr) | | 12.8 | |

Example 5. Preparation of Spray Dried Dispersions

Spray dried dispersions of compound (1-1) were prepared using five selected polymers: HPMCAS-MG (Shin Etsu Chemical Co., Ltd.), HPMCP-HP55 (Shin Etsu Chemical Co., Ltd.), PVP (ISP, a division of Ashland, Inc.), PVP-VA (BASF Corp.), and Eudragit L100-55 (Evonik Industries AG). All spray dried solutions were prepared at 25% and 50% by weight with each polymer. All solutions were prepared in acetone, with the exception of the PVP solutions, which were prepared in ethanol. For each solution, 1.0 g of solids (polymer and compound (1-1)) were prepared in 10 g of solvent. The solutions were spray dried using a Büchi B-290, PE-024 spray dryer with a 1.5 mm nozzle and a Büchi B-295, P-002 condenser. The spray dryer nozzle pressure was set to 80 psi, the target outlet temperature was set to 40° C., the chiller temperature was set to −20° C., the pump speed was set to 100%, and the aspirator setting was 100%. After spray drying, the solid dispersions were collected and dried overnight in a low temperature convection oven to remove residual solvents.

Example 6. Stability with Humidity and Temperature

TABLE 6

Figure 9:
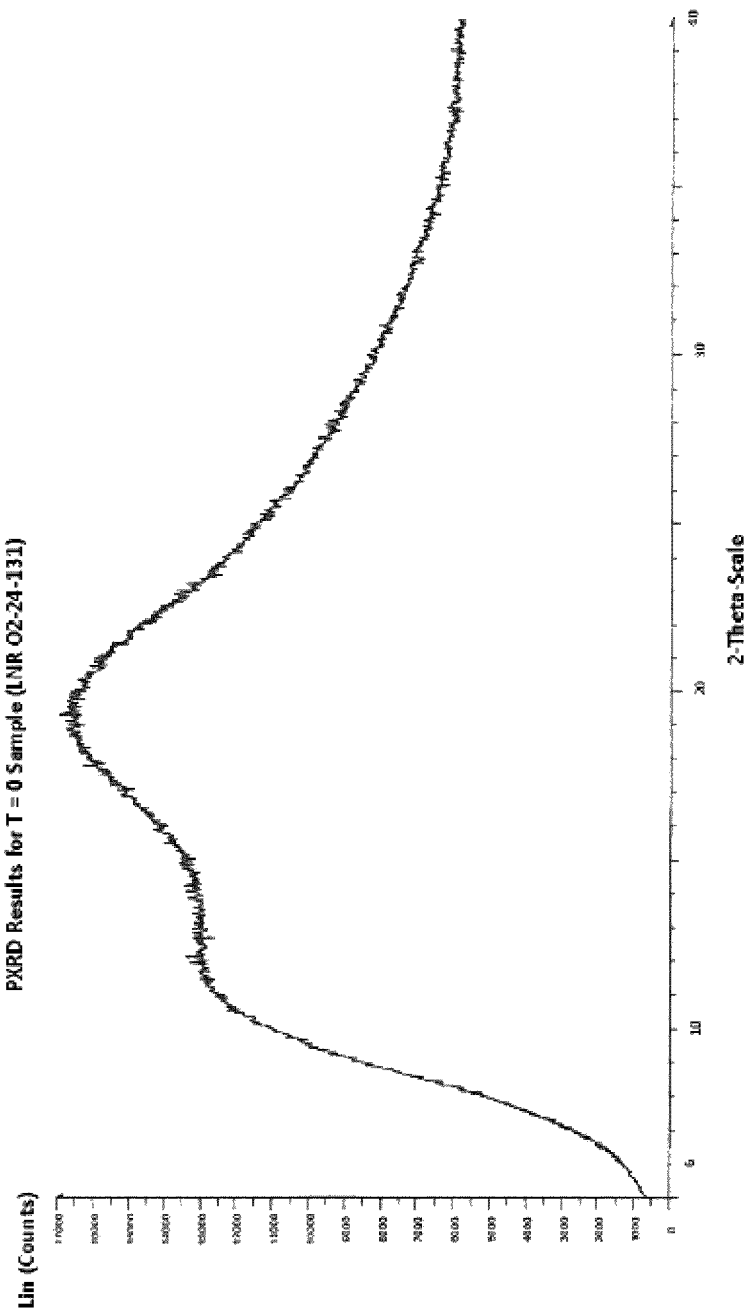
FIG. 9 illustrates a powder X-ray diffraction profile of solid dispersions of compound (1-1) in HPMCAS-MG at time zero of a stability test.
Figure 10:
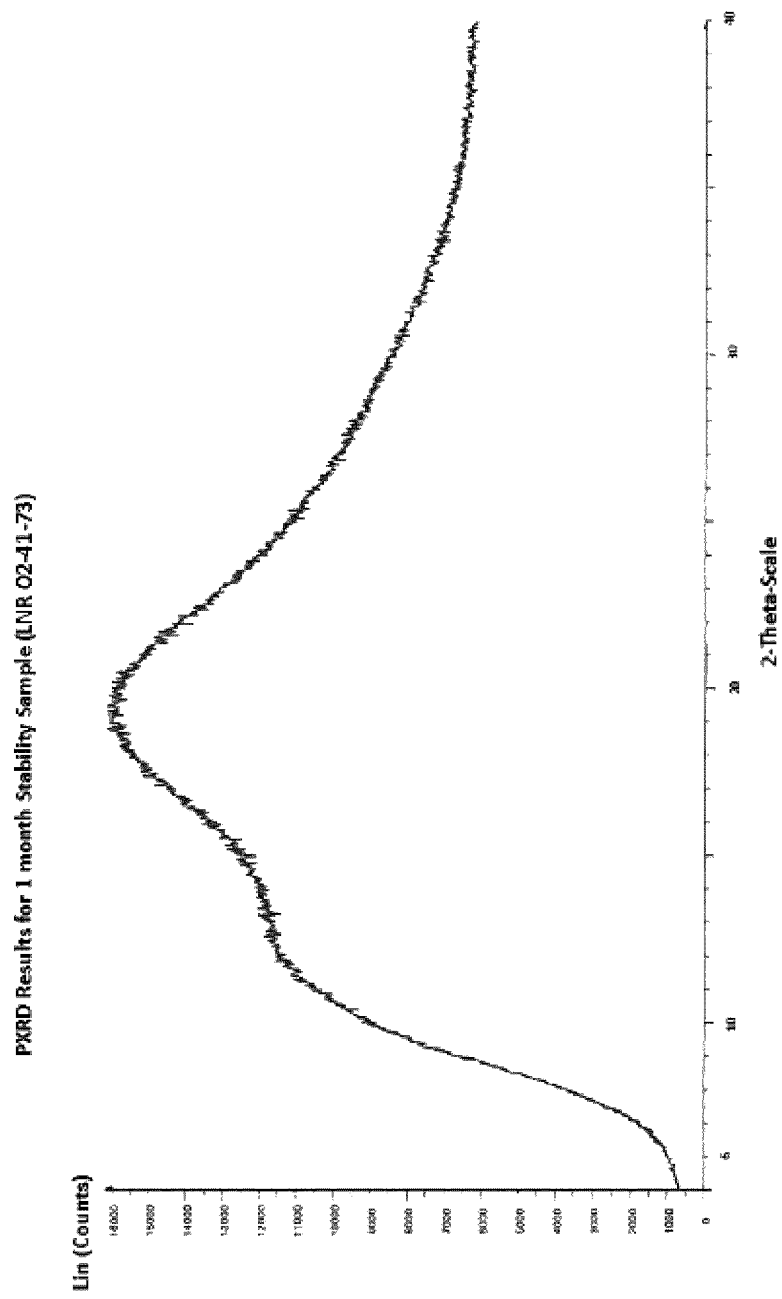
FIG. 10 illustrates a powder X-ray diffraction profile of solid dispersions of compound (1-1) in HPMCAS-MG after 1 month at 40° C. and 75% relative humidity.
Figure 11:
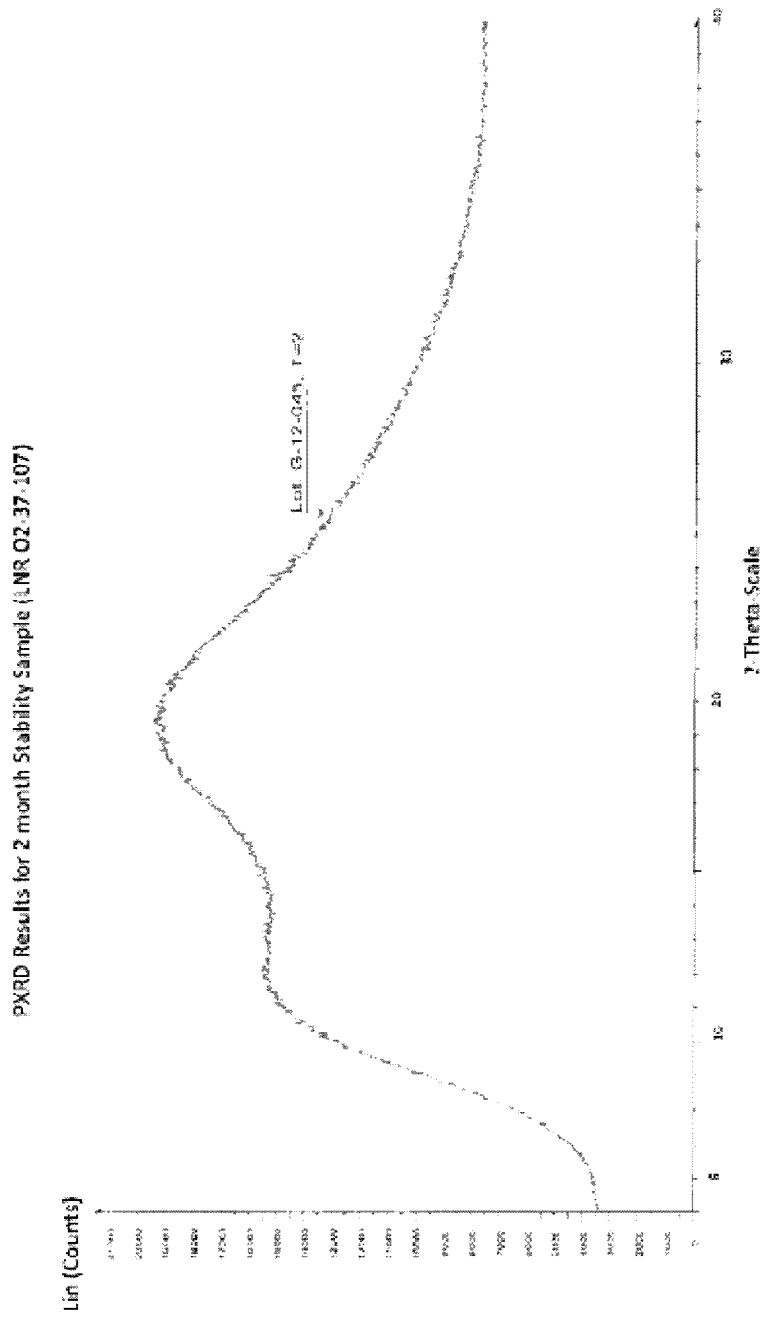
FIG. 11 illustrates a powder X-ray diffraction profile of solid dispersions of compound (1-1) in HPMCAS-MG after 2 months at 40° C. and 75% relative humidity.
Figure 12:
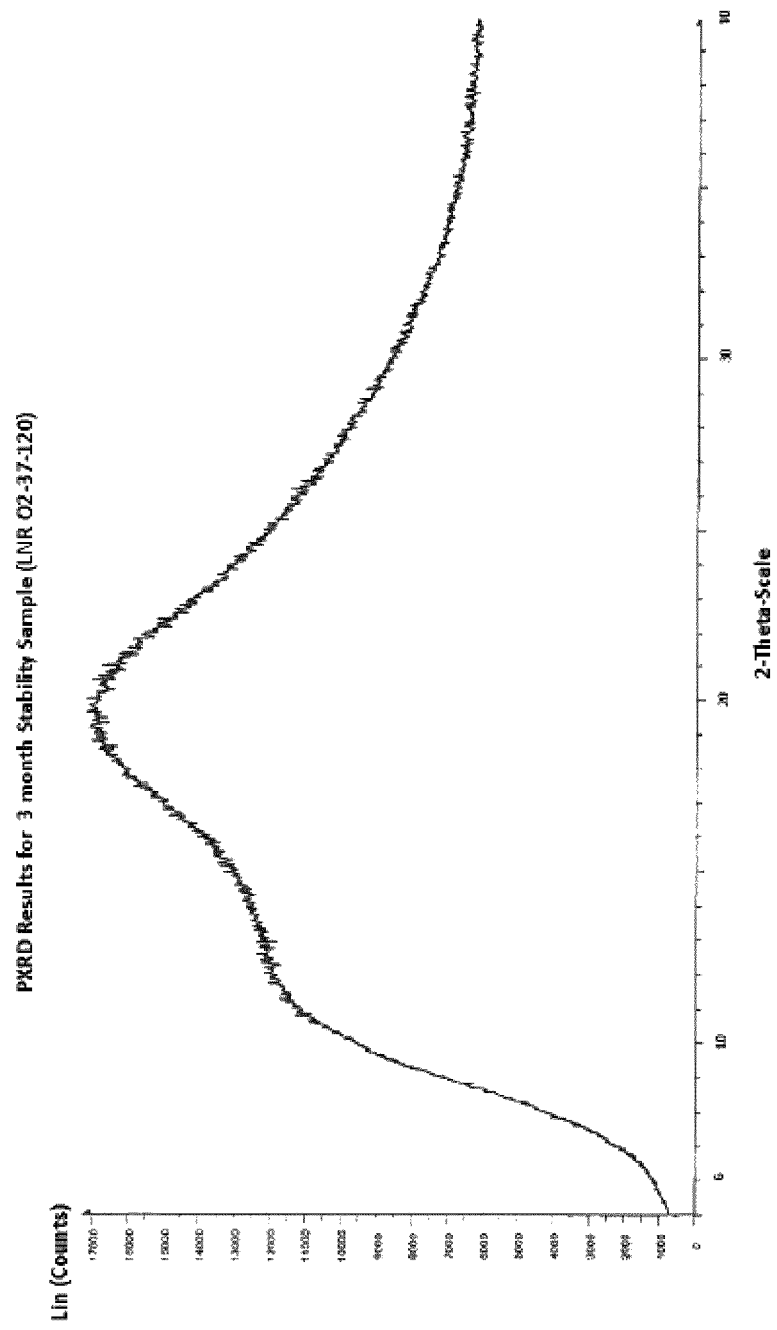
FIG. 12 illustrates a powder X-ray diffraction profile of solid dispersions of compound (1-1) in HPMCAS-MG after 3 months at 40° C. and 75% relative humidity.

| Test | Procedure | Acceptance Criteria | T = 0 (Initial) | T = 1 month (storage at 40° C./75% RH) | T = 2 month (storage at 40° C./75% RH) | T = 3 month (storage at 40° C./75% RH) |
| --- | --- | --- | --- | --- | --- | --- |
| Appearance | AM-0002 | White to off-white powder | Test Date/Ref: 6 Aug. 2012/02-41-2 White Powder | Test Date/Ref: 24 Sep. 2012/02-41-59 White Powder | Test Date/Ref: 24 Oct. 2012/02-37-106 White Powder | Test Date/Ref: 17 Dec. 2012/02-37-119 White Powder |
| Potency (HPLC) | AM-0028 | 45.0 – 55.0 wt % | Test Date/Ref: 25 Jul. 2012/02-37-21 50.0 | Test Date/Ref: 25 Sep. 2012/02-4Hl0 49.4 | Test Date/Ref: 24 Oct. 2012/02-37-105 49.8 | Test Date/Ref: 29 Nov. 2012/02-34-107 49.2 |
| Individual Related Substances (HPLC) | AM-0029 | Report results | Test Date/Ref: 25 Jul. 2012/02•34-49 RRT     % Area No reportable related substances | Test Date/Ref: 26 Sep. 2012/02-41-64 RRT     % Area No reportable related substances | Test Date/Ref: 24 Oct. 2012/02-37-105 RRT     % Area 0.68     0.06 0.77     0.06 | Test Date/Ref: 29 Nov. 2012/02-34-107 RRT     % Area 0.68     0.07 0.77     0.09 |
| Total Related Substances (HPLC) | AM•0029 | Report results | Test Date/Ref: 25 Jul. 2012/02-34-49 No reportable related substances | Test Date/Ref: 26 Sep. 2012/02-41-64 No reportable related substances | Test Date/Ref: 24 Oct. 2012/02-37-105 0.12% | Test Date/Ref: 29 Nov. 2012/02-34-107 0.16% |
| Water Content (KF) | AM-0030 USP <921> | Report results (wt %) | Test Date/Ref: 2 Aug. 2012/02-41-1 1.52 | Test Date/Ref: 27 Sep. 2012/02-37-99 2.53 | Test Date/Ref: 25 Oct. 2012102-37-110 2.70 | Test Date/Ref: 29 Nov. 2012/02•37-116 3.43 |
| X-Ray Powder Diffraction (XRPD) | USP <941> | Consistent with an amorphous form | Test Date/Ref: 24 Jul. 2012/02•24-131 Consistent with an amorphous form See FIG. 9 | Test Date/Ref: 1 Oct. 2012/02-41-73 Consistent with an amorphous form See FIG. 10 | Test Date/Ref: 24 Oct. 2012/02-37-107 Consistent with an amorphous form See FIG. 11 | Test Date/Ref: 17 Dec. 2012/02-37-120 Consistent with an amorphous form See FIG. 12 |
| Modulated Differential Scanning Calorimetry (mDSC) | USP <891> (n = 2 replicates) | Report individual and average glass transtion temperatures ($T_g$, ° C.) | Test Date/Ref: 24 Jul. 2012/02-24-130 Replicate 1 = 134.30° C., Replicate 2 = 134.23° C., Replicate 3 = 135.28° C., Average = 134.60° C. | Test Date/Ref: 26 Sep. 2012/02-37-98 Replicate 1 = 134.65° C., Replicate 2 = 134.43° C., Average = 134.54° C. | Test Date/Ref: 24 Oct. 2012/02-37-108 Replicate 1 = 135.35° C., Replicate 2 = 134.93° C., Average = 135.14° C. | Test Date/Ref: 17 Dec. 2012/02-37-121 Replicate 1 = 134.36° C. Replicate 2 = 137.16° C. Average = 135.76° C. |

Spray dried dispersions of compound (1-1) in HPMCAS-MG were assessed for stability by exposure to moisture at elevated temperature. The glass transition temperature (Tg) as a function of relative humidity was determined at 75% relative humidity, 40° C. for 1, 2 and 3 months. The spray dried dispersion was stored in an LDPE bag inside a HDPE bottle to simulate bulk product packaging. The results are summarized in Table 6. At time zero, the Tg was 134° C., at 1 month the Tg was 134° C., at 2 months the Tg was 135° C. and at 3 months the Tg was 134° C. and only a single inflection point was observed for each measurement. X-ray diffraction patterns were also obtained for each sample. FIG. 9 illustrates a powder X-ray diffraction profile of solid dispersions of compound (1-1) in HPMCAS-MG at time zero of a stability test. FIGS. 10, 11, and 12 illustrate a powder X-ray diffraction profile of solid dispersions of compound (1-1) in HPMCAS-MG after 1-, 2-, and 3-months, respectively, at 40° C. and 75% relative humidity. The patterns did not show any diffraction lines associated with compound (1-1).

Example 7: Mechanistic of Action of Compound (1-1) and its Activity in Combination with Other Anti-Cancer Compounds Methods.
Cell lines: 22 diffuse large B-cell lymphoma (DLBCL), 4 mantle cell lymphomas, 3 multiple myelomas, 3 splenic marginal zone lymphoma and 1 prolymphocytic leukemia. Antiproliferative activity of compound (1-1) (OncoEthix SA, Switzerland) was assessed by MTT and its cytotoxic activity by Annexin V staining and gene expression profiling (GEP) with Illumina HumanHT-12 Expression BeadChips. Data mining was done with LIMMA, GSEA, Metacore. Synergy was assessed in cells (2-5 cell lines) exposed for 72 h to increasing doses of compound (1-1) alone or in combination with increasing doses of other agents. MTT assays were performed and Chou-Talalay combination index (CI) calculated.

Results.
Compound (1-1) (500 nM, 72 h) showed cytostatic activity in 29/33 (88%) cell lines and apoptosis in 3/22 (14%). Mutations in genes coding for MYD88 and components of BCR (P=0.027), and ABC signaling phenotypes (P=0.008) were significantly associated with apoptosis induction. We performed GEP on 2 cell lines (SU-DHL-6, SU-DHL-2), treated with DMSO or compound (1-1) (500 nM) for 1, 2, 4, 8 or 12 hours. Most upregulated genes were histones. MYC target genes were highly significantly enriched among all compound (1-1) regulated transcripts and MYC was the most frequently downregulated gene. Compound (1-1) also downregulated MYD88, IRAK1, TLR6, IL6, STAT3, and TNFRSF17, members of the NFKB, TLR and JAK/STAT pathways. NFKB target genes (IRF4, TNF AIP3 and BIRC3) were also downregulated (PCR). Immunoblotting and immunohistochemistry showed a reduction of transcriptionally active pSTAT3 in 2 ABC cell lines, and a reduction in nuclear localization of p50 (NFKB 1), indicating an inhibitory effect of compound (1-1) on the canonical NFKB pathway. Finally, IL10 and IL4 production was reduced after 24 hours compound (1-1) treatment.

Synergy was observed with everolimus (median CI=0.1; range 0.1-0.2), ibrutinib in ABC-DLBCL (CI=0.04; 0.02-0.1), idelalisib (CAL101) (CI=0.5; 0.04-2.4), vorinostat (CI=0.5; 0.3-0.6), rituximab (CI=0.5; 0.4-0.5), decitabine (CI=0.6; 0.6-0.7), lenalidomide (CI=0.7; 0.6-0.7), and all-trans retinoic acid (CI=0.4; 0.1-1.6). Additive effects were observed for combinations with romidepsin (CI=1.08; 1-1.22), bendamustine (CI=0.92; 0.83-1.1), and doxorubicin (CI=0.83; 0.7-0.96).

Example 8: Expression of MicroRNAs Involved in the Pathogenesis of DLBCL

Methods.

Total RNA was extracted from 2 DLBCL cell lines, the germinal center B-cell (GCB) type DOHH2 and from the activated B-cell-like (ABC)-type SU-DHL-2, following treatment with compound (1-1) (500 nM) or DMSO for 4 h or 8 h. RNA samples were labeled with cyanine-3 dye using the Agilent microRNA Complete Labeling System & Hyb Kit and hybridized to the Agilent Human microRNA microarray v.3. Raw expression values were obtained with Agilent Feature Extraction Software, log-transformed and normalized by the quantile method. Data were filtered to exclude relatively invariant features and those below the detection threshold. Limma (Linear Models for Microarray data analysis) was employed using R/Bioconductor and the filtered dataset. Baseline miRNA profiling was obtained in 22 DLBCL cell lines with the Nanostring nCounter Human v2 miRNA Expression Assay kit. Baseline gene expression profiling (GEP) was obtained in the 22 cell lines with the Illumina HumanHT-12 v4 Expression BeadChip. Selected miRNA changes were validated by real-time PCR. The miRWalk database (Dweep et al, 2011) was used to retrieve the validated miRNA targets. Gene Set Enrichment Analysis (GSEA) software was used to assess enrichment of miRNA targets in the GEP datasets.

Results.

miRNA profiling of the GCB and ABC DLBCL cell lines exposed to compound (1-1) identified four downregulated miRNAs and eight which were upregulated. Among them, the oncomirs miR-92a-1-5p (log 2 FC, −2.01; P=0.004) and miR-21-3p (log 2 FC, −0.37; P=0.0045) were downregulated, while the tumor suppressor miR-96-5p (log 2 FC, 0.39; P=0.041) was upregulated. Interestingly, changes of these miRNAs matched GEP variations of validated target genes (e.g., miR-92a-1-5p: CDKN1A, log 2 FC, 0.81, CDKN2A, log 2 FC, 0.81; miR-96-5p: MYC, log 2 FC, −0.57, MYD88, log 2 FC, −0.35). We then evaluated if these three miRNAs play a role in compound (1-1)-sensitivity by obtaining baseline miRNA and GEP profiling data in 22 DLBCL cell lines. Compared to 8 cell lines with lower sensitivity to compound (1-1) (IC50>500 nM), the 14 sensitive cell lines (IC50<500 nM) presented lower miR-96-5p expression levels (log ratio, 2.12; P=0.026) and their GEPs were significantly enriched for validated miR-96-5p targets (normalized enrichment score, 1.4; P=0.026), suggesting miR-96-5p levels may predict response to compound (1-1).

Conclusions.

Changes in the expression levels of biologically relevant miRNAs may contribute to the response to compound (1-1). miR-92a-1-5p, the oncomir which was most strongly downregulated by compound (1-1), is a member of the MYC target MIR17HG (mir-17-92 cluster), involved in the pathogenesis and chemo-resistance of lymphomas, mainly contributing to PI3K./AKT/mTOR pathway activation. Since the cell cycle transcriptional regulator E2F1 is targeted by mir-17-92, compound (1-1) may contribute to cell cycle arrest and to the E2F1 target gene downregulation reported with BRD inhibitors in DLBCL cell lines. miR-21-3p, also downregulated by compound (1-1), is a well-known oncomir, and forced miR-21-3p expression in transgenic mice results in the development of leukemias and lymphomas. miR-96-5p, upregulated by compound (1-1), targets oncogenes such as RAS or MYC, and low expression has been reported in mantle cell lymphoma. Interestingly, low miR-96-5p baseline levels were associated with higher sensitivity to compound (1-1), an observation meriting validation in other tumor models and evaluation in clinical studies.

Example 9: Compound (1-1) Affects the Expression of MicroRNAs Involved in the Pathogenesis of Diffuse Large B-Cell Lymphoma Total RNA was extracted from 2 diffuse large B-Cell lymphoma (DLBCL) cell lines, the germinal center B-cell (GCB) type DOHH2 and activated B-cell-like (ABC)-type SU-DHL-2, following treatment with 500 nM compound (1-1) or DMSO for 4 h or 8 h. RNA samples were labeled with cyanine-3 dye using the Agilent microRNA Complete Labeling System & Hyb Kit and hybridized to the Agilent Human microRNA microarray v.3. Raw expression values were obtained with Agilent Feature Extraction Software, log-transformed and normalized by the quantile method. Data were filtered to exclude relatively invariant features and those below the detection threshold. Limma was employed using R/Bioconductor and the filtered dataset. Baseline microRNA (abbreviated miRNA) profiling was obtained from 30 B-cell lymphoma cell lines, including 22 DLBCL with the Nanostring nCounter Human v2 miRNA Expression Assay kit. Baseline gene expression profiling (GEP) was obtained with the Illumina HumanHT-12 v4 Expression BeadChip. Selected miRNA changes were validated by real-time PCR. Validated miRNA targets were retrieved using the miRWalk database (Dweep et al, 2011). Gene Set Enrichment Analysis (GSEA) was used to assess enrichment of miRNA targets in the GEP datasets. miRNA profiling of the germinal center B-cell (GCB) and activated B-cell-like (ABC) DLBCL cell lines exposed to compound (1-1) identified four downregulated miRNAs and eight which were upregulated. Among them, the oncomirs miR-92a-1-5p (log 2 FC, −2.01; P=0.004) and miR-21-3p (log 2 FC, −0.37; P=0.0045) were downregulated, while the tumor suppressor miR-96-5p (log 2 FC, 0.39; P=0.041) was upregulated (FIGS. 13A-13C). Changes in these miRNAs matched GEP variations of validated target genes (e.g., miR-92a-1-5p: CDKN1A, log 2 FC, 0.81, CDKN2A, log 2 FC, 0.81; miR-96-5p: MYC, log 2 FC, −0.57, MYD88, log 2 FC, −0.35).

Figure 14A:
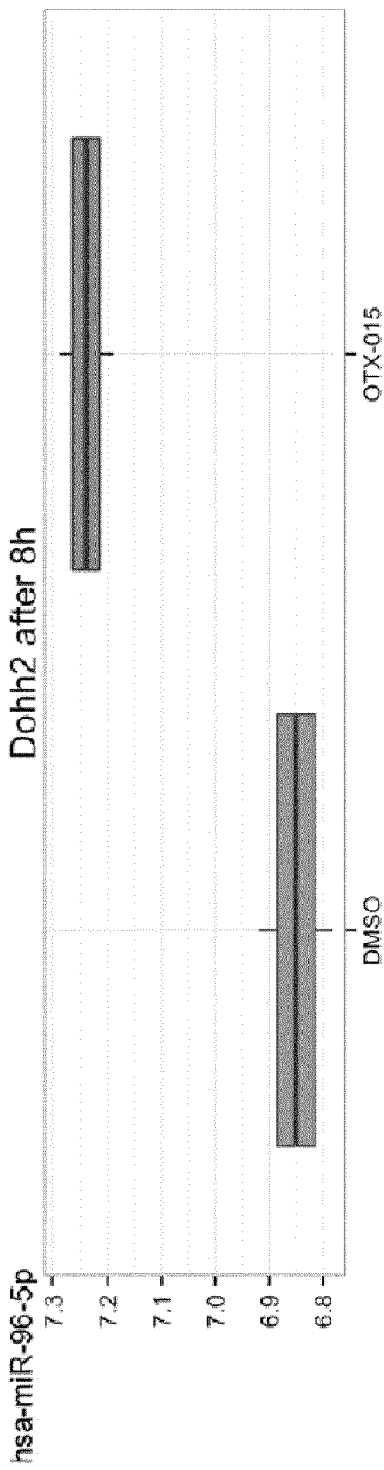
FIGS. 14A-14C show GSEA plots illustrating the enrichment of validated miR-96-5p 25 targets in 14 DLBCL cell lines with higher sensitivity to compound (1-1) when compared with eight DLBCL cell lines with lower sensitivity to compound (1-1). "NES" indicates normalized enrichment score.
Figure 14B:
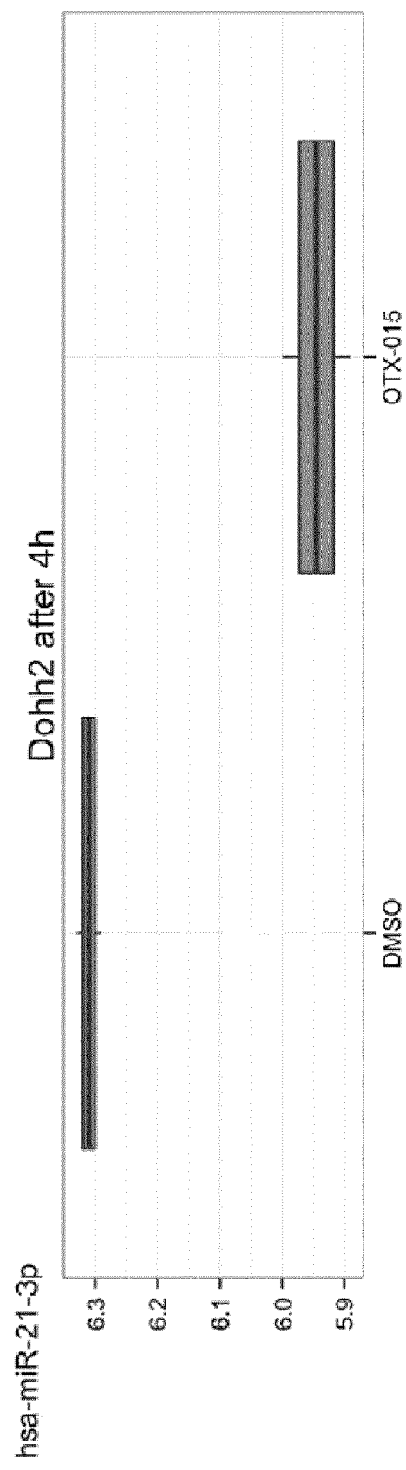
Figure 14C:
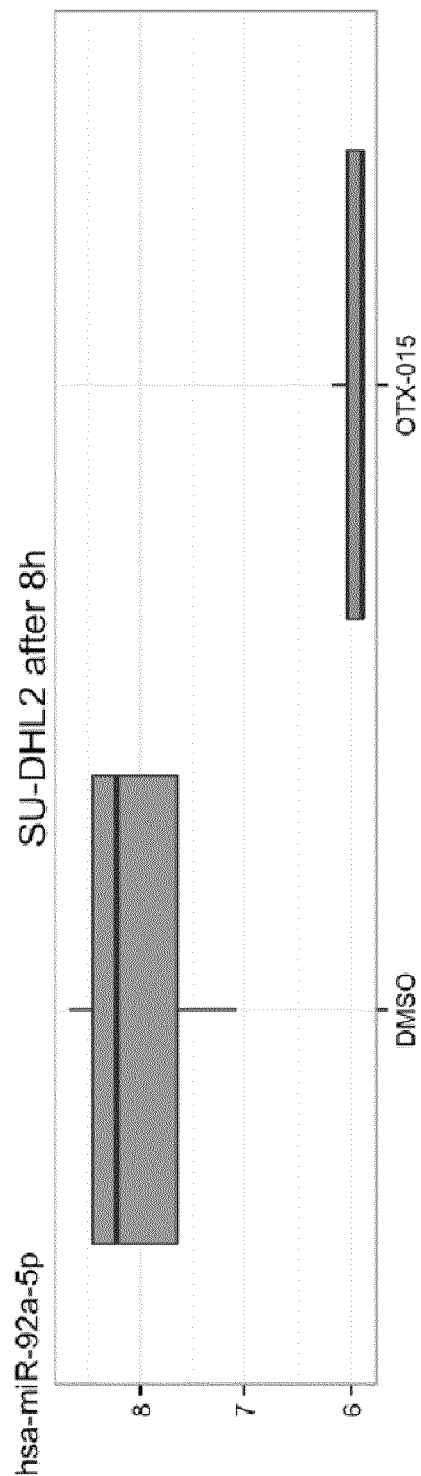

The role these three miRNAs play in compound (1-1)-sensitivity was evaluated by obtaining baseline miRNA and GEP profiling data in a large panel of B-cell lymphoma cell lines. Levels of miR-96-5p were lower in the sensitive cell lines (IC50<500 nM) compared to those with higher resistance to compound (1-1) (IC50>500 nM) both in the whole group and within DLBCL only. Sensitive cell lines GEPs were significantly enriched for validated miR-96-5p targets (normalized enrichment score, 1.4; P=0.04) (FIGS. 14A-14C).

As illustrated in FIGS. 13A-13 and FIGS. 14A-14C, changes in the expression levels of biologically relevant miRNAs contribute to response to compound (1-1). miR-92a-1-5p, the oncomir most strongly downregulated by compound (1-1), is a member of the MYC target MIR17HG (mir-17-92 cluster), involved in the pathogenesis and chemo-resistance of lymphomas, mainly contributing to PI3K/AKT/mTOR pathway activation. miR-21-3p, also downregulated by compound (1-1), is a well known oncomir, and forced miR-21-3p expression in transgenic mice results in the development of leukemias and lymphomas. miR-96-5p, upregulated by compound (1-1), targets oncogenes such as RAS or MYC, and low expression has been reported in mantle cell lymphoma. Furthermore, low miR-96-5p baseline levels were associated with higher sensitivity to compound (1-1).

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

I claim:

1. A method of treating diffuse large B-cell lymphoma (DLBCL) in a mammal comprising:
    obtaining cancer cells from a patient;
    determining a gene expression profile for the cancer cells; and
    administering to the patient a pharmaceutically acceptable amount of a compound which is (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide dihydrate, or (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide, or a pharmaceutically acceptable salt thereof, wherein the gene expression profile of the patient's cancer cells is positive for at least one gene associated with sensitivity to the compound.

2. The method according claim 1, wherein the at least one gene is selected from the group consisting of members of the NFKB, TLR and JAK/STAT pathways.

3. The method according to claim 2, wherein the members of the NKKB, TLR, and JAK/STAT pathways are selected from the group consisting of MYD88, IRAK1, TLR6, IL6, STAT3, and TNFRSF17.

* * * * *